(12) United States Patent
Ikemoto et al.

(10) Patent No.: US 6,743,924 B2
(45) Date of Patent: Jun. 1, 2004

(54) METHOD FOR PRODUCING 1-SUBSTITUTED-1,2,3-TRIAZOLE DERIVATIVE

(75) Inventors: Tomomi Ikemoto, Takarazuka (JP); Tatsuya Ito, Kashiba (JP); Kiminori Tomimatsu, Minoh (JP); Yasuhiro Sawai, Ikoma (JP); Hirohiko Nishiyama, Takatsuki (JP); Yasushi Isogami, Toyonaka (JP)

(73) Assignee: Takeda Chemical Industries, Ltd., Osaka (JP)

( * ) Notice: Subject to any disclaimer, the term of this patent is extended or adjusted under 35 U.S.C. 154(b) by 89 days.

(21) Appl. No.: 10/019,264

(22) PCT Filed: Jul. 16, 2001

(86) PCT No.: PCT/JP01/06145

§ 371 (c)(1),
(2), (4) Date: Apr. 19, 2002

(87) PCT Pub. No.: WO02/06249

PCT Pub. Date: Jan. 24, 2002

(65) Prior Publication Data

US 2003/0069419 A1 Apr. 10, 2003

(30) Foreign Application Priority Data

| Jul. 19, 2000 | (JP) | .................................. | 2000-218814 |
| Jul. 19, 2000 | (JP) | .................................. | 2000-218834 |
| Sep. 20, 2000 | (JP) | .................................. | 2000-284925 |
| May 29, 2001 | (JP) | .................................. | 2001-160464 |

(51) Int. Cl.$^7$ ............................................. C07D 249/04

(52) U.S. Cl. ..................................................... 548/255

(58) Field of Search .......................... 548/255

(56) References Cited

FOREIGN PATENT DOCUMENTS

| JP | 5-170763 | 7/1993 |
| JP | 8-53425 | 2/1996 |
| WO | 98-03505 | 1/1998 |

OTHER PUBLICATIONS

S. Cheng et al., "Synthesis and Cytotoxicity of 4–Aminobutyrophenone Hydrochlorides and Their Substituted Pyrimidinylhydrazones", J. Med. Chem. 9, pp. 945–949 (1966).

Primary Examiner—Joseph K. McKane
Assistant Examiner—Golam M M Shameem
(74) Attorney, Agent, or Firm—Wenderoth, Lind & Ponack, L.L.P.

(57) ABSTRACT

A method for producing a compound of the formula:

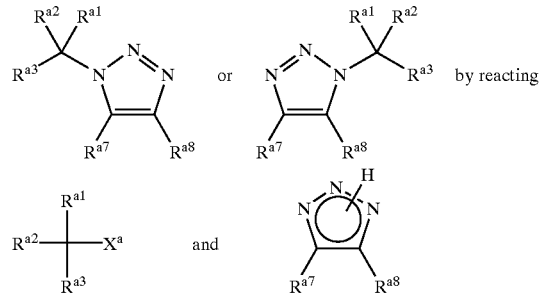

by reacting (1) in a secondary or tertiary alcohol in the presence of a base, or (2) in the absence of a base is provided. According to this method, a 1-substituted-1,2,3-triazole compound having a tyrosine kinase inhibitory action can be produced efficiently in a high yield at an industrial large scale by a convenient method

11 Claims, 2 Drawing Sheets

METHOD FOR PRODUCING 1-SUBSTITUTED-1,2,3-TRIAZOLE DERIVATIVE

This application is a 371 of PCT/JP01/06145 filed Jul. 16, 2001.

TECHNICAL FIELD

The present invention relates to production methods of intermediates for 1-substituted-1,2,3-triazole compounds having an inhibitory action on growth factor receptor tyrosine kinases (especially HER2) useful as pharmaceutical agents.

BACKGROUND ART

As a production method of an intermediate for a 1-substituted-1,2,3-triazole compound having a tyrosine kinase inhibitory action, for example, there is mentioned a method comprising condensing compound (1) of the following formula and compound (2) of the following formula in the presence of a base in a solvent inert to the reaction (e.g., aromatic hydrocarbons such as benzene, toluene, xylene etc., ethers such as tetrahydrofuran, dioxane etc., ketones such as acetone, 2-butanone etc., halogenated hydrocarbons such as chloroform, dichloromethane etc., N,N-dimethylformamide, dimethyl sulfoxide, and a mixed solvent of these) to give the objective compound (3) (JP-A-11-60571, WO 98/03505):

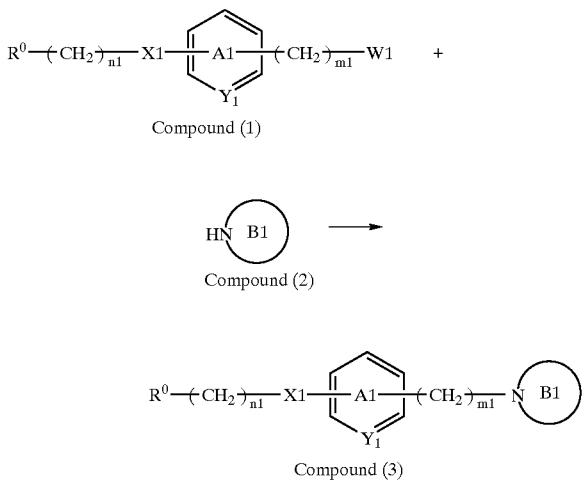

Compound (1)

Compound (2)

Compound (3)

wherein $W_1$ is a leaving group, $R^0$ is an optionally substituted aromatic heterocyclic group, X1 is an oxygen atom, an optionally oxidized sulfur atom, —C(=O)— or —CH(OH)—, $Y_1$ is CH or N, m1 is an integer of 0 to 10, n1 is an integer of 1 to 5, the cyclic group

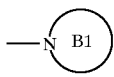

is an optionally substituted aromatic azole group and the ring A1 may be further substituted.

In addition, as a production method of a 1-alkyl-1,2,3-triazole compound, for example, there is mentioned a method comprising reacting the compound (b2) of the following formula and the compound (b3) of the following formula in the presence or absence of a base (JP-A-5-170763):

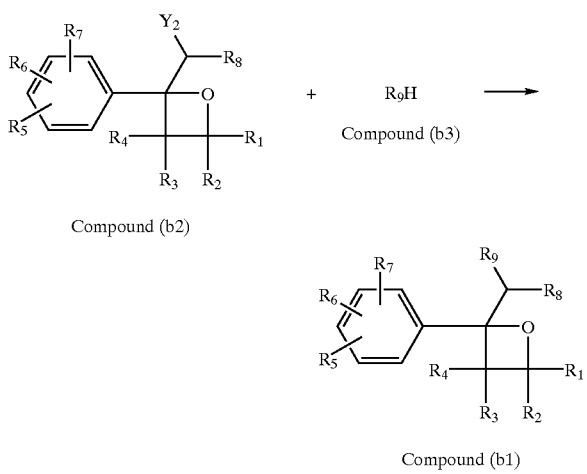

Compound (b2)

+ R9H

Compound (b3)

Compound (b1)

wherein $R_1$, $R_2$, $R_3$, $R_4$ and $R_8$ are the same or different and each is a hydrogen atom or a lower alkyl group, $R_2$ and $R_3$ in combination may form, together with the carbon atoms to which they are bonded, a cyclopentane ring or a cyclohexane ring, $R_5$, $R_6$ and $R_7$ are the same or different and each is a hydrogen atom, a halogen atom, a lower alkyl group optionally substituted by halogen atom(s) or a lower alkoxy group optionally substituted by halogen atom(s), $Y_2$ is a halogen atom, a lower alkyl sulfonyloxy group or an aryl sulfonyloxy group, and $R_9$ is a 5 or 6-membered heterocyclic group having 1 to 3 nitrogen atom(s), and wherein a 1H-1,2,4-triazole group is excluded and the heterocyclic group is optionally substituted by 1 to 3, the same or different halogen atom(s), lower alkyl group(s) or lower alkoxy group(s).

The aforementioned conventional production methods pose problems in that they show low reaction selectivity, and therefore, a low yield. A method using a silver salt of 1H-1,2,3-triazole shows fine selectivity but requires expensive starting materials. Therefore, there is a demand for an industrially advantageous production method of an intermediate for a 1-substituted-1,2,3-triazole compound having an inhibitory action on growth factor receptor tyrosine kinases (especially HER2).

As a production method for obtaining a 1,2,3-triazole compound useful as a starting material of pharmaceutical agents or an intermediate for printing, image processing agents, by the use of a hydrazone derivative, there is known, for example, a method comprising reacting compound (c1) of the following formula and compound (c2) under neutral or basic conditions to give compound (3) (JP-A-8-53425):

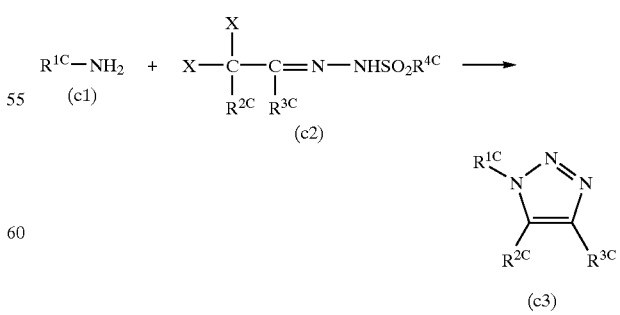

In the above formulas, $R^{1c}$ is a lower alkyl group optionally substituted by halogen atom(s), a phenyl group wherein benzene ring is optionally substituted by at least one substituent selected from halogen atom, lower alkyl group and lower alkoxy group, a benzyl group wherein benzene ring is optionally substituted by at least one substituent selected from halogen atom, lower alkyl group and lower alkoxy group, a lower alkylamino group wherein alkyl group is optionally substituted by halogen atom, a phenylamino group wherein benzene ring is optionally substituted by at least one substituent selected from halogen atom, lower alkyl group and lower alkoxy group, an ammonium group that forms a salt with an inorganic acid or a carboxyl group that forms a salt with ammonia; X is a halogen atom; $R^{2c}$ and $R^{3c}$ are each a hydrogen atom or a lower alkyl group optionally substituted by halogen atom(s); and $R^{4c}$ is a lower alkyl group optionally substituted by halogen atom(s) or a phenyl group wherein benzene ring is optionally substituted by at least one substituent selected from halogen atom, lower alkyl group and lower alkoxy group.

As a production method of an amine compound such as the above-mentioned compound (c1), there is known a method comprising reacting phthalimide butyryl chloride and chlorobenzene in the presence of anhydrous aluminum chloride, and treating the obtained 4-chloro-4-phthalimide butyrophenone with acetic acid and hydrochloric acid to give 4-chloro-4-aminobutyrophenone hydrochloride [Journal of Medicinal Chemistry (J. Med. Chem.), vol. 9, pp. 945–949 (1966)].

The conventional production method for obtaining the aforementioned compound (c3) showed lower yield from the compound (c1). A conventional production method for obtaining an amine compound, such as compound (c1), poses a problem in that it requires many steps. Therefore, there is a demand for an industrially advantageous production method of an intermediate for a 1-substituted-1,2,3-triazole compound having an inhibitory action on growth factor receptor tyrosine kinase (especially, HER2).

DISCLOSURE OF THE INVENTION

The present inventors have studied various production methods of 1-substituted-1,2,3-triazole derivatives, and first found that a reaction in a secondary or tertiary alcohol in the presence of a base or a reaction in the absence of a base unexpectedly results in the selective production of the objective 1-substituted-1,2,3-triazole derivative in a high yield, and that this production method is fully satisfactory on an industrial scale, based on which they intensively investigated and completed the present invention.

They have also found that a reaction of an alkylamine compound and a hydrazone derivative, followed by a treatment with a base, unexpectedly results in the selective production of the objective 1-substituted-1,2,3-triazole derivative in a high yield, and that this production method is fully satisfactory on an industrial scale, based on which they intensively investigated and completed the present invention.

Further, the present inventors have found that a production method via a protected 4-hydroxymethyloxazole compound as an intermediate unexpectedly results in the production of the objective product in a high yield, and that this production method is fully satisfactory on an industrial scale, based on which they intensively investigated and completed the present invention.

Accordingly, the present invention provides the following.

1. A method for producing a compound of the formula:

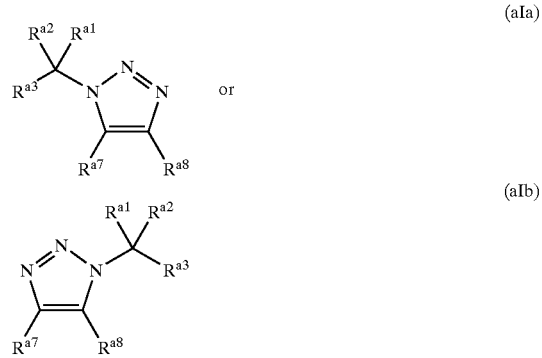

wherein $R^{a1}$ and $R^{a2}$ are each a hydrogen atom, a substituted hydroxy, a substituted thiol, a substituted amino, an optionally substituted hydrocarbon group, an optionally substituted heterocyclic group or an acyl;

$R^{a3}$ is a group of the formula:

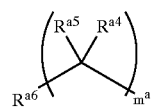

wherein $R^{a4}$ and $R^{a5}$ are each a hydrogen atom, an optionally substituted hydroxy, an optionally substituted thiol, an optionally substituted amino, an optionally substituted hydrocarbon group, an optionally substituted heterocyclic group or an acyl, or $R^{a4}$ and $R^{a5}$ in combination form oxo, $R^{a6}$ is an optionally substituted aromatic group, and $m^a$ is an integer of 0 to 10; or two or three from $R^{a1}$, $R^{a2}$ and $R^{a3}$ form an optionally substituted ring, together with the adjacent carbon atom; and $R^{a7}$ and $R^{a8}$ are each a hydrogen atom, a halogen, an optionally substituted hydroxy, an optionally substituted thiol, an optionally substituted amino, an optionally substituted hydrocarbon group, an optionally substituted heterocyclic group or an acyl, which method comprises reacting a compound of the formula:

wherein $X^a$ is a leaving group and other symbols are as defined above, or a salt thereof [hereinafter to be also referred briefly to as compound (aII)] and a compound of the formula:

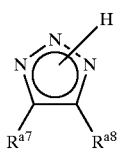

(aIII)

wherein each symbol is as defined above, or a salt thereof,
(1) in a secondary or tertiary alcohol in the presence of a base, or
(2) in the absence of a base.

2. The production method of the aforementioned 1, which comprises reaction in a secondary or tertiary alcohol in the presence of a base.

3. The production method of the aforementioned 1, which comprises reaction in a tertiary alcohol in the presence of a base.

4. The production method of 1 above, wherein $R^{a1}$ is a hydrogen atom.

5. The production method of 1 above, wherein $R^{a1}$ and $R^{a2}$ are each a hydrogen atom.

6. The production method of 1 above, wherein $R^{a3}$ is a group of the formula:

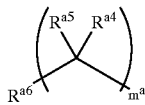

wherein each symbol is as defined in the aforementioned 1.

7. The production method of 6 above, wherein $R^{a4}$ and $R^{a5}$ are each a hydrogen atom.

8. The production method of 6 above, wherein $R^{a6}$ is an optionally substituted phenyl.

9. The production method of 6 above, wherein $m^a$ is 3.

10. The production method of 1 above, wherein $R^{a7}$ and $R^{a8}$ are each a hydrogen atom.

11. A salt of a compound of the formula:

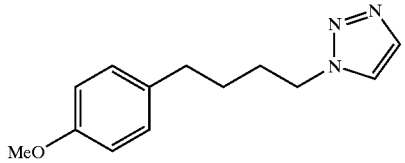

12. A compound of the formula:

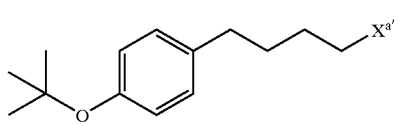

(aIIa)

wherein $X^{a'}$ is a halogen atom, $OSO_2R^a$ or $OCOR^a$ wherein $R^a$ is an optionally substituted hydrocarbon group [hereinafter to be referred to as compound (aIIa)].

13. A method for producing compound (aIIa), which comprises reacting a compound of the formula:

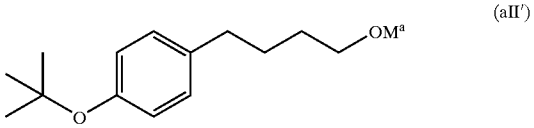

(aII')

wherein $M^a$ is a hydrogen atom, an alkali metal atom or an alkaline earth metal atom [hereinafter to be referred to as compound (aII')], and 1) thionyl halide [hereinafter to be referred to as compound (aa)], 2) oxalyl halide [hereinafter to be referred to as compound (ab)], 3) a compound of the formula:

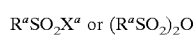

wherein $R^a$ is an optionally substituted hydrocarbon group and $X^a$ is a leaving group [hereinafter to be referred to as compound (ac)] or 4) a compound of the formula:

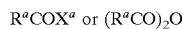

wherein $R^a$ and $X^a$ are as defined above [hereinafter to be referred to as compound (ad)] under basic conditions.

14. A compound of the formula:

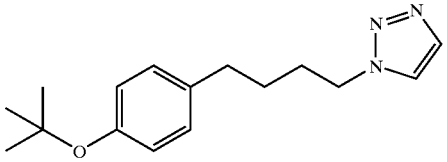

or a salt thereof [hereinafter to be also referred to as compound (aIe)].

15. The production method of the aforementioned 1 wherein $R^{a1}$, $R^{a2}$, $R^{a7}$ and $R^{a8}$ are each a hydrogen atom and $R^{a3}$ is 3-[4-(t-butoxyphenyl)]propyl.

16. A method for producing a compound of the formula:

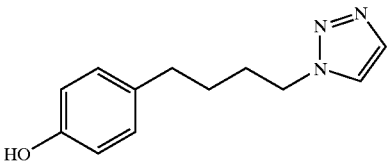

which comprises reacting a compound of the formula:

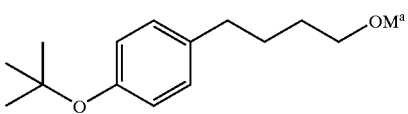

wherein $M^a$ is a hydrogen atom, an alkaline metal atom or an alkaline earth metal atom, and 1) thionyl halide, 2) oxalyl halide, 3) a compound of the formula:

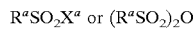

wherein $R^a$ is an optionally substituted hydrocarbon group and $X^a$ is a leaving group or 4) a compound of the formula:

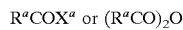

wherein $R^a$ and $X^a$ are as defined above, under basic conditions to give a compound of the formula:

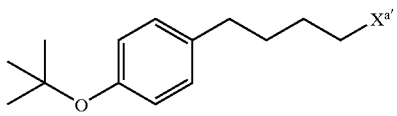

wherein $X^{a'}$ is a halogen atom, $OSO_2R^a$ or $OCOR^a$ wherein $R^a$ is as defined above, and reacting this compound with a compound of the formula:

or a salt thereof, (1) in the presence of a base in a secondary or tertiary alcohol, or (2) in the absence of a base to give a compound of the formula:

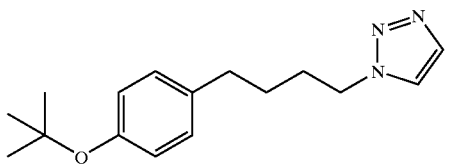

and deprotecting this compound.

17. A method for producing a compound of the formula:

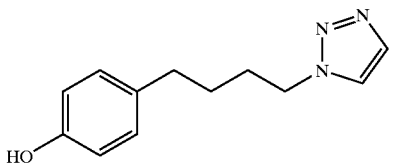

which comprises deprotecting a compound of the formula:

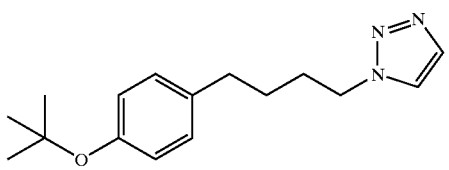

18. A method for producing a compound of the formula:

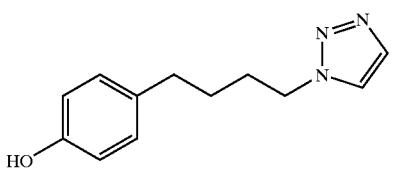

which comprises deprotecting a compound of the formula:

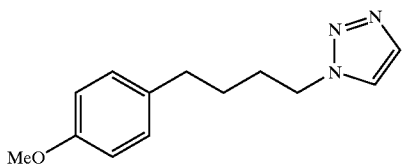

19. A method for producing a compound of the formula:

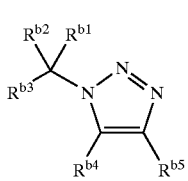

(bI)

wherein $R^{b1}$, $R^{b2}$ and $R^{b3}$ are each a hydrogen atom, an optionally substituted hydroxy, an optionally substituted thiol, an optionally substituted amino, an optionally substituted hydrocarbon group, an optionally substituted heterocyclic group or an acyl, or two or three from $R^{b1}$, $R^{b2}$ and $Rb^3$ form, together with the adjacent carbon atom, an optionally substituted ring, and $R^{b4}$ and $R^{b5}$ are each a hydrogen atom, an optionally substituted hydroxy, an optionally substituted thiol, an optionally substituted amino, an optionally substituted hydrocarbon group, an optionally substituted heterocyclic group or an acyl, and $R^{b6}$ is an optionally substituted alkyl or an optionally substituted phenyl, or a salt thereof [hereinafter to be also referred to as compound (bI)], which comprises reacting a compound of the formula:

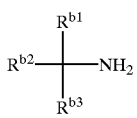

(bII)

wherein each symbol is as defined above, or a salt thereof [hereinafter to be also referred to as compound (bII)] and a compound of the formula:

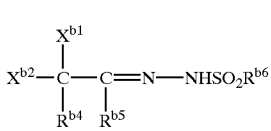

(bIII)

wherein $X^{b1}$ and $Xb^2$ are each a halogen, and $R^{b4}$, $R^{b5}$ and $R^{b6}$ are as defined above, or a salt thereof, [hereinafter also to be referred to as compound (bIII)] and treating the reaction mixture with a base.

20. The production method of 19 above, wherein $R^{b1}$ is a hydrogen atom.

21. The production method of 19 above, wherein $R^{b1}$ and $R^{b2}$ are each a hydrogen atom.

22. The production method of the aforementioned 19, wherein $R^{b3}$ is a group of the formula:

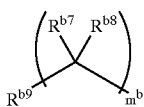

wherein $R^{b7}$ and $R^{b8}$ are each a hydrogen atom, an optionally substituted hydroxy, an optionally substituted thiol, an optionally substituted amino, an optionally substituted hydrocarbon group, an optionally substituted heterocyclic group or an acyl, or $R^{b7}$ and $R^{b8}$ in combination form oxo, $R^{b9}$ is an optionally substituted aromatic group, and mb is an integer of 0 to 10.

23. The production method of 22 above wherein $R^{b7}$ and $R^{b8}$ are each a hydrogen atom, $R^{b9}$ is an optionally substituted phenyl, and $m^b$ is 3.

24. The production method of 23 above wherein $R^{b1}$ and $R^{b2}$ are each a hydrogen atom.

25. The production method of 19 above wherein $R^{b4}$ and $R^{b5}$ are each a hydrogen atom.

26. The production method of 19 above wherein $R^{b6}$ is a phenyl substituted by alkyl.

27. A method for producing a compound of the formula:

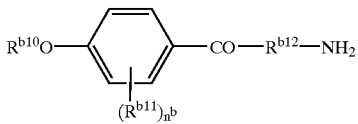

(bVI)

wherein, $R^{b10}$ is an optionally substituted amino, an optionally substituted hydrocarbon group, an optionally substituted heterocyclic group or an acyl, $R^{b11}$ is a substituent, $n^b$ is an integer of 0 to 4, and $R^{b12}$ is an optionally substituted alkylene, an optionally substituted alkenylene or an optionally substituted alkynylene, or a salt thereof, which comprises reacting a compound of the formula:

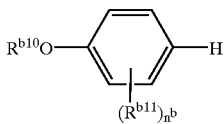

(bIV)

wherein each symbol is as defined above, or a salt thereof [hereinafter to be also referred to as compound (bIV)] and a compound of the formula:

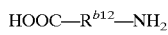

HOOC—$R^{b12}$—NH$_2$  (bV)

wherein $R^{b12}$ is as defined above, a salt thereof or a reactive derivative thereof [hereinafter to be also referred to as compound (bV)].

28. A method for producing a compound of the formula:

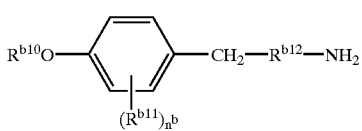

(bVII)

wherein each symbol is as defined above, or a salt thereof [hereinafter to be also referred to as compound (bVII)], which comprises reacting compound (bIV) and compound (bV), and reducing the obtained compound (bVI) or a salt thereof.

29. A method for producing a compound of the formula:

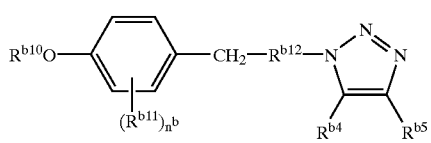

(bVIII)

wherein each symbol is as defined above, or a salt thereof [hereinafter to be also referred to as compound (bVIII)], which comprises reacting compound (bIV) and compound (bV), reducing the obtained compound (bVI) or a salt thereof, reacting the obtained compound (bVII) and compound (bIII), and treating the reaction mixture with a base.

30. The production method of 29 above, wherein $R^{b4}$ and $R^{b5}$ are each a hydrogen atom, $R^{b10}$ is a $C_{1-3}$ alkyl, $R^{b12}$ is a trimethylene and $n^b$ is 0.

31. A trifluoromethanesulfonate of a compound of the formula:

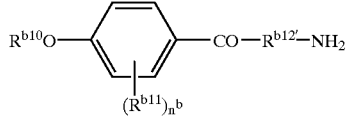

wherein $R^{b12'}$ is trimethylene and other symbols are as defined in the aforementioned 27.

32. A method for producing a compound of the formula:

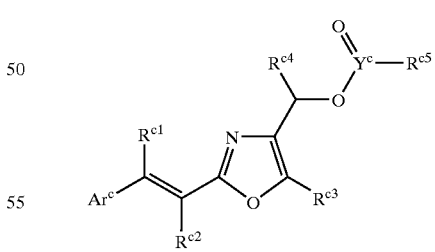

(cIV)

wherein $Ar^c$ is an optionally substituted aromatic group, $R^{c1}$ and $R^{c2}$ are each a hydrogen atom or a lower alkyl, $R^{c3}$ and $R^{c4}$ are each a hydrogen atom or a lower alkyl, $Y^c$ is C, S or SO and $R^{c5}$ is a hydrogen atom, a lower alkyl, an optionally substituted phenyl, an optionally substituted benzyloxy or an optionally substituted benzylamino, or a salt thereof [hereinafter to be also referred to as compound (cIV)], which comprises reacting a reaction mixture of a compound of the formula:

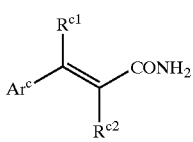
(cI)

wherein each symbol is as defined above, or a salt thereof [hereinafter to be also referred to as compound (cI)] and a compound of the formula:

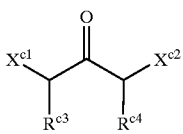
(cII)

wherein $X^{c1}$ and $X^{c2}$ are each a halogen, and other symbols are as defined above, or a salt thereof [hereinafter to be also referred to as compound (cII)] with a compound of the formula:

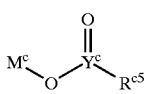
(cIII)

wherein $M^c$ is a hydrogen atom or a metal, and other symbols are as defined above, or a salt thereof [hereinafter to be also referred to as compound (cIII)].

33. The production method of 32 above, wherein $Ar^c$ is 4-trifluoromethylphenyl.

34. The production method of 32 above, wherein $R^{c1}$, $R^{c2}$, $R^{c3}$ and $R^{c4}$ are each a hydrogen atom and $R^{c5}$ is methyl.

36. A method for producing a compound of the formula:

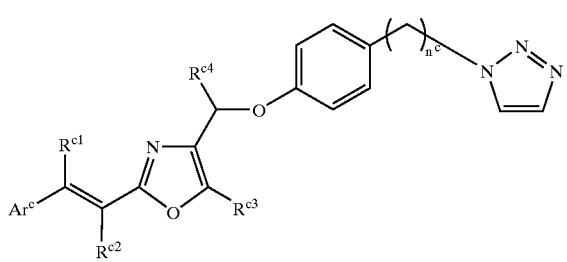
(cVII)

wherein each symbol is as defined above, or a salt thereof [hereinafter to be also referred to as compound (cVII)], which comprises subjecting compound (cIV) to hydrolysis or catalytic reduction, subjecting the obtained compound of the formula:

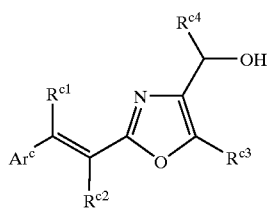
(cV)

wherein each symbol is as defined above, or a salt thereof [hereinafter to be also referred to as compound (cV)] to sulfonylation or halogenation, and reacting the compound with a compound of the formula:

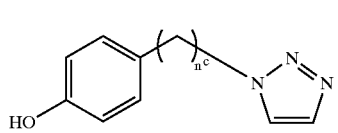
(cVI)

wherein $n^c$ is an integer of 1 to 10, or a salt thereof [hereinafter to be also referred to as compound (cVI)].

37. The production method of 36 above, wherein $Ar^c$ is 4-trifluoromethylphenyl.

38. The production method of 36 above, wherein $R^{c1}$, $R^{c2}$, $R^{c3}$ and $R^{c4}$ are each a hydrogen atom, $R^{c5}$ is methyl and $n^c$ is 4.

39. A method for producing compound (cVII) or a salt thereof, which comprises reacting a reaction mixture of compound (cI) and compound (cII) with compound (cIII), subjecting the resulting compound to hydrolysis or catalytic reduction, subjecting the obtained compound (cV) to sulfonylation or halogenation, and reacting the compound with compound (cVI).

40. The production method of 39 above, wherein $Ar^c$ is 4-trifluoromethylphenyl.

41. The production method of 39 above, wherein $R^{c1}$, $R^{c2}$, $R^{c3}$ and $R^{c4}$ are each a hydrogen atom, $R^{c5}$ is methyl and $n^c$ is 4.

42. A method for producing a compound of the formula:

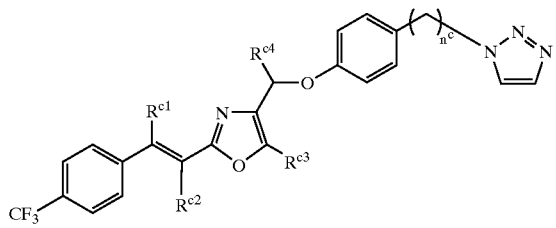
(cVIIa)

wherein each symbol is defined above, or a salt thereof, which comprises subjecting a reaction mixture of a compound of the formula:

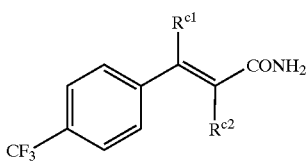

(cIa)

wherein each symbol is as defined in the aforementioned 32 or a salt thereof and compound (cII) or a salt thereof to hydrolysis, subjecting the obtained compound of the formula:

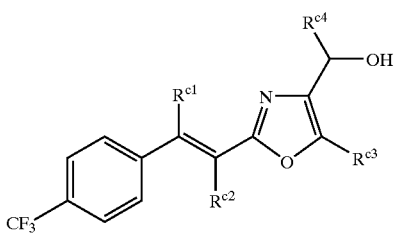

(cVa)

wherein each symbol is as defined above or a salt thereof to sulfonylation or halogenation, and reacting the resulting compound with compound (cVI) or a salt thereof.

43. A method for producing compound (cVIIa) or a salt thereof, which comprises reacting a reaction mixture of compound (cIa) or a salt thereof and compound (cII) or a salt thereof with compound (cVI) or a salt thereof.

44. A compound of the formula:

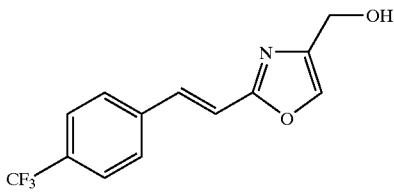

45. A method for producing compound (cVIIa) or a salt thereof, which comprises subjecting the compound (cVa) or a salt thereof to sulfonylation or halogenation, and reacting the resulting compound with compound (cVI) or a salt thereof.

46. 1-[4-[4-[[2-[(E)-2-[4-(Trifluoromethyl)phenyl]ethenyl]-1,3-oxazol-4-yl]methoxy]phenyl]butyl]-1H-1,2,3-triazole.

47. The crystal of the aforementioned 46, having characteristic peaks at diffraction angles of about 6.98, 14.02, 17.56, 21.10 and 24.70 degrees in powder X-ray diffraction.

48. A pharmaceutical composition comprising the crystal of the aforementioned 46.

DETAILED DESCRIPTION OF THE INVENTION

Figure 1:
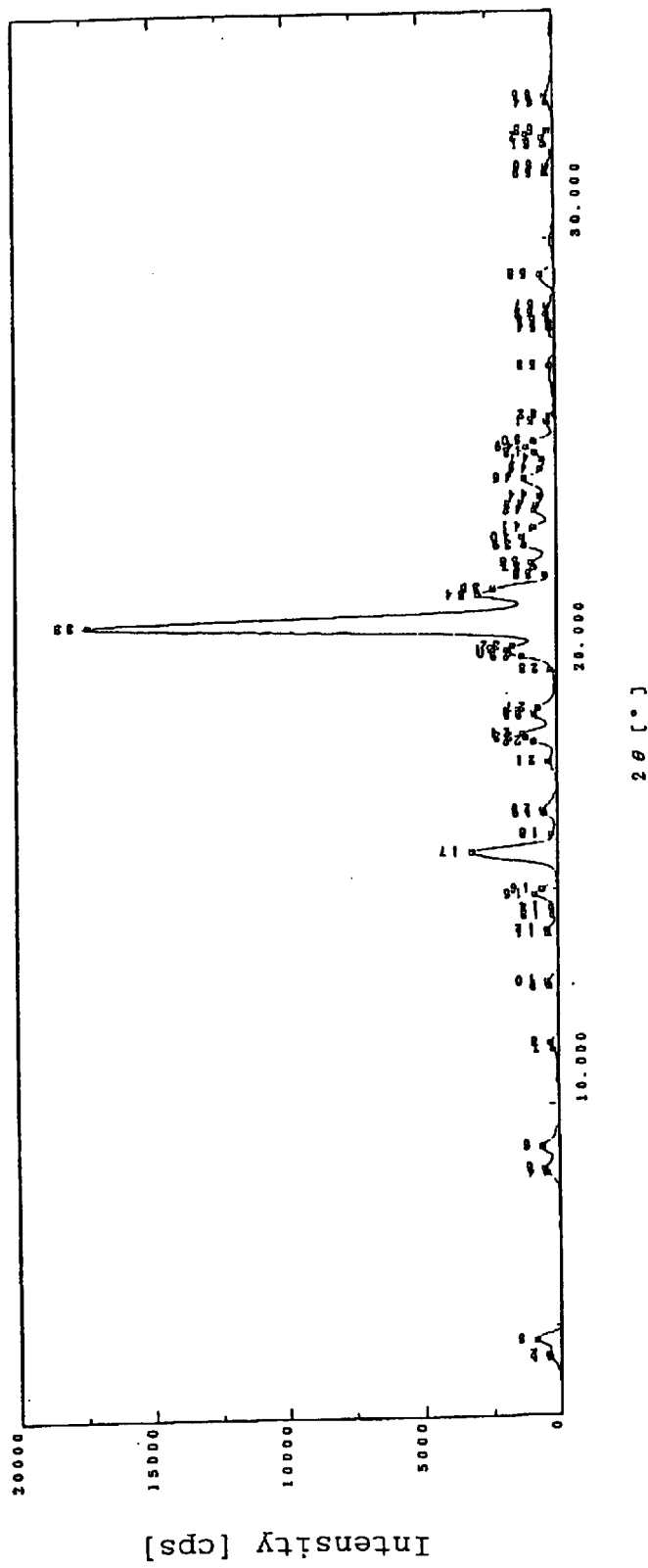
FIG. 1 is a powder X-ray diffraction chart of the compound obtained in Reference Example 22.

In this specification, the "hydrocarbon group" of the "an optionally substituted hydrocarbon group" is exemplified by chain or cyclic hydrocarbon group (e.g., alkyl, alkenyl, alkynyl, cycloalkyl, aryl, aralkyl etc.) and the like, with preference given to chain or cyclic hydrocarbon group having 1 to 16 carbon atoms.

Examples of the "alkyl" preferably include, for example, $C_{1-6}$ alkyl (e.g., methyl, ethyl, propyl, isopropyl, butyl, isobutyl, sec-butyl, tert-butyl, pentyl, hexyl etc.) and the like.

Examples of the "alkenyl" preferably include, for example, $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl etc.) and the like.

Examples of the "alkynyl" preferably include, for example, $C_{2-6}$ alkynyl (e.g., ethynyl, propargyl, 1-butynyl, 2-butynyl, 3-butynyl, 1-hexynyl etc.) and the like.

Examples of the "cycloalkyl" preferably include, for example, $C_{3-6}$ cycloalkyl (e.g., cyclopropyl, cyclobutyl, cyclopentyl, cyclohexyl etc.) and the like.

Examples of the "aryl" preferably include, for example, $C_{6-14}$ aryl (e.g., phenyl, 1-naphthyl, 2-naphthyl, 2-biphenylyl, 3-biphenylyl, 4-biphenylyl, 2-anthryl etc.) and the like.

Examples of the "aralkyl" preferably include, for example, $C_{7-16}$ aralkyl (e.g., benzyl, phenethyl, diphenylmethyl, 1-naphthylmethyl, 2-naphthylmethyl; 2,2-diphenylethyl, 3-phenylpropyl, 4-phenylbutyl, 5-phenylpentyl etc.) and the like.

The "substituent" of said "optionally substituted hydrocarbon group or aromatic group" is exemplified by halogen atom (e.g., fluorine, chlorine, bromine, iodine etc.), $C_{1-3}$ alkylenedioxy (e.g., methylenedioxy, ethylenedioxy etc.), nitro, cyano, optionally halogenated $C_{1-6}$ alkyl, optionally halogenated $C_{2-6}$ alkenyl, optionally halogenated $C_{2-6}$ alkynyl, optionally halogenated $C_{3-6}$ cycloalkyl, optionally substituted $C_{6-14}$ aryl, optionally halogenated $C_{1-6}$ alkoxy, $C_{1-6}$ alkoxy-carbonyl-$C_{1-6}$ alkoxy (e.g., ethoxycarbonylmethyloxy etc.), hydroxy, $C_{6-14}$ aryloxy (e.g., phenyloxy, 1-naphthyloxy, 2-naphthyloxy etc.), $C_{7-16}$ aralkyloxy (e.g., benzyloxy, phenethyloxy etc.), mercapto, optionally halogenated $C_{1-6}$ alkylthio, $C_{6-14}$ arylthio (e.g., phenylthio, 1-naphthylthio, 2-naphthylthio etc.), $C_{7-16}$ aralkylthio (e.g., benzylthio, phenethylthio etc.), amino, mono-$C_{1-6}$ alkylamino (e.g., methylamino, ethylamino etc.), mono-$C_{6-14}$ arylamino (e.g., phenylamino, 1-naphthylamino, 2-naphthylamino etc.), di-$C_{1-6}$ alkylamino (e.g., dimethylamino, diethylamino, ethylmethylamino etc.), di-$C_{6-14}$ arylamino (e.g., diphenylamino etc.), formyl, carboxy, $C_{1-6}$ alkyl-carbonyl (e.g., acetyl, propionyl etc.), $C_{3-6}$ cycloalkyl-carbonyl (e.g., cyclopropylcarbonyl, cyclopentylcarbonyl, cyclohexylcarbonyl etc.), $C_{1-6}$ alkoxy-carbonyl (e.g., methoxycarbonyl, ethoxycarbonyl, propoxycarbonyl, tert-butoxycarbonyl etc.), $C_{6-14}$ arylcarbonyl (e.g., benzoyl, 1-naphthoyl, 2-naphthoyl etc.), $C_{7-16}$ aralkyl-carbonyl (e.g., phenylacetyl, 3-phenylpropionyl etc.), $C_{6-14}$ aryloxy-carbonyl (e.g., phenoxycarbonyl etc.), $C_{7-16}$ aralkyloxy-carbonyl (e.g., benzyloxycarbonyl, phenethyloxycarbonyl etc.), 5 or 6-membered heterocyclic carbonyl (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl etc.), carbamoyl, mono-$C_{1-6}$ alkyl-carbamoyl (e.g., methylcarbamoyl, ethylcarbamoyl etc.), di-$C_{1-6}$ alkyl-carbamoyl (e.g., dimethylcarbamoyl, diethylcarbamoyl, ethylmethylcarbamoyl etc.), $C_{6-14}$ arylcarbamoyl (e.g., phenylcarbamoyl, 1-naphthylcarbamoyl, 2-naphthylcarbamoyl etc.), 5 or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl etc.), $C_{1-6}$ alkylsulfonyl (e.g., methylsulfonyl, ethylsulfonyl etc.), $C_{6-14}$ arylsulfonyl (e.g., phenylsulfonyl, 1-naphthylsulfonyl, 2-naphthylsulfonyl etc.), formylamino, $C_{1-6}$ alkylcarbonylamino (e.g., acetylamino etc.), $C_{6-14}$ aryl-carbonylamino (e.g., benzoylamino, naphthoylamino etc.), $C_{1-6}$ alkoxycarbonylamino (e.g., methoxycarbonylamino, ethoxycarbonylamino, propoxycarbonylamino, butoxycarbonylamino etc.), $C_{1-6}$ alkylsulfonylamino (e.g., methylsulfonylamino, methylsulfonylamino etc.), $C_{6-14}$ arylsulfonylamino (e.g., phenylsulfonylamino, 2-naphthylsulfonylamino, 1-naphthylsulfonylamino etc.), $C_{1-6}$ alkyl-carbonyloxy (e.g., acetoxy, propionyloxy etc.), $C_{6-14}$ aryl-carbonyloxy (e.g., benzoyloxy, naphthylcarbonyloxy etc.), $C_{1-6}$ alkoxy-carbonyloxy (e.g., methoxycarbonyloxy, ethoxycarbonyloxy, propoxycarbonyloxy, butoxycarbonyloxy etc.), mono-$C_{1-6}$ alkyl-carbamoyloxy (e.g., methylcarbamoyloxy, methylcarbamoyloxy etc.), di-$C_{1-6}$ alkyl-carbamoyloxy (e.g., dimethylcarbamoyloxy, diethylcarbamoyloxy etc.), $C_{6-14}$ aryl-carbamoyloxy (e.g., phenylcarbamoyloxy, naphthylcarbamoyloxy etc.), nicotinoyloxy, 5 to 7-membered saturated cyclic amino (e.g., pyrrolidin-1-yl, piperidino, piperazin-1-yl, morpholino, thiomorpholino, tetrahydroazepin-1-yl etc.), 5 to 10-membered aromatic heterocyclic group (e,g., 2-thienyl, 3-thienyl, 2-furyl, 3-furyl, 2-oxazolyl, 4-oxazolyl, 5-oxazolyl, 1,2,4-triazolyl, 1,2,3-triazolyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 2-pyrazinyl, 2-pyrimidinyl, 4-pyrimidinyl, 3-pyrrolyl, 1-imidazolyl, 2-imidazolyl, 4-imidazolyl, 5-imidazolyl, 3-pyridazinyl, 3-isothiazolyl, 3-isooxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.) and the like.

The "hydrocarbon group" may have 1 to 5, preferably 1 to 3, for example, the above-mentioned substituents at substitutable position(s). When the number of the substituents is two or more, the respective substituents may be the same or different.

The aforementioned "optionally halogenated $C_{1-6}$ alkyl" is exemplified by $C_{1-6}$ alkyl optionally having 1 to 5, preferably 1 to 3, halogen atom(s) (e.g., fluorine, chlorine, bromine, iodine etc.), such as methyl, ethyl, propyl, isopropyl, butyl, isobutyl, sec-butyl, tert-butyl, pentyl and hexyl, and the like. Specifically, for example, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like are mentioned.

As the aforementioned "optionally halogenated $C_{2-6}$ alkenyl", for example, $C_{2-6}$ alkenyl optionally having 1 to 5, preferably 1 to 3, halogen atom(s) (e.g., fluorine, chlorine, bromine, iodine etc.) is mentioned, such as vinyl, propenyl, isopropenyl, 2-buten-1-yl, 4-penten-1-yl and 5-hexen-1-yl, and the like.

As the aforementioned "optionally halogenated $C_{2-6}$ alkynyl", for example, $C_{2-6}$ alkynyl optionally having 1 to 5, preferably 1 to 3, halogen atom(s) (e.g., fluorine, chlorine, bromine, iodine etc.) is mentioned, such as 2-butyn-1-yl, 4-pentyn-1-yl and 5-hexyn-1-yl), and the like.

As the aforementioned "optionally halogenated $C_{3-6}$ cycloalkyl", for example, $C_{3-6}$ cycloalkyl optionally having 1 to 5, preferably 1 to 3, halogen atom(s) (e.g., fluorine, chlorine, bromine, iodine etc.) is mentioned, such as (cyclopropyl, cyclobutyl, cyclopentyl and cyclohexyl, and the like. Specifically, for example, cyclopropyl, cyclobutyl, cyclopentyl, cyclohexyl, 4,4-dichlorocyclohexyl, 2,2,3,3-tetrafluorocyclopentyl, 4-chlorocyclohexyl are mentioned.

As the "$C_{6-14}$ aryl" of the aforementioned "optionally substituted $C_{6-14}$ aryl", for example, phenyl, 1-naphthyl, 2-naphthyl, 2-biphenylyl, 3-biphenylyl, 4-biphenylyl, 2-anthryl and the like are mentioned.

As the "substituent" of the aforementioned "optionally substituted $C_{6-14}$ aryl", for example, 1 to 5 from halogen, hydroxy, optionally halogenated $C_{1-6}$ alkyl, optionally halogenated $C_{1-6}$ alkoxy and the like can be mentioned.

As the aforementioned "optionally halogenated $C_{1-6}$ alkoxy", for example, $C_{1-6}$ alkoxy optionally having 1 to 5, preferably 1 to 3, halogen atom(s) (e.g., fluorine, chlorine, bromine, iodine etc.) is mentioned, such as methoxy, ethoxy, propoxy, isopropoxy, butoxy, isobutoxy, sec-butoxy, pentyloxy and hexyloxy, and the like. Specifically, for example, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, tert-butoxy, pentyloxy, hexyloxy and the like are mentioned.

Examples of the aforementioned "optionally halogenated $C_{1-6}$ alkylthio" include $C_{1-6}$ alkylthio optionally having 1 to 5, preferably 1 to 3, halogen atom(s) (e.g., fluorine, chlorine, bromine, iodine etc.) such as methylthio, ethylthio, propylthio, isopropylthio, butylthio, sec-butylthio and tert-butylthio, and the like. Specifically, methylthio, difluoromethylthio, trifluoromethylthio, ethylthio, propylthio, isopropylthio, butylthio, 4,4,4-trifluorobutylthio, pentylthio, hexylthio and the like are mentioned.

In the present specification, the "heterocyclic group" of the "optionally substituted heterocyclic group" is exemplified by a monovalent group and the like obtained by removing optional one hydrogen atom from 5 to 14-membered (monocyclic, bicyclic or tricyclic) heterocycle, preferably (i) 5 to 14-membered (preferably 5 to 10-membered) aromatic heterocycle, (ii) 5 to 10-membered non-aromatic heterocycle and (iii) 7 to 10-membered crosslinked heterocycle, having, besides carbon atom, 1 or 2 kind(s) of 1 to 4 hetero atom(s) selected from nitrogen atom, sulfur atom and oxygen atom.

Examples of the above-mentioned "5 to 14-membered (preferably 5 to 10-membered) aromatic heterocycle" include aromatic heterocycles such as thiophene, oxazole, triazole, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolizidine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isooxazole, furazan, phenoxazine and the like, and a ring formed by condensation of these rings (preferably monocycle) with 1 to several (preferably 1 or 2) aromatic ring(s) (e.g., benzene ring etc.) and the like.

Examples of the above-mentioned "5 to 10-membered non-aromatic heterocycle" include pyrrolidine, imidazoline, pyrazolidine, pyrazoline, piperidine, piperazine, morpholine, thiomorpholine, dioxazole, oxadiazoline, thiadiazoline, triazoline, thiadiazole, dithiazole and the like.

Examples of the above-mentioned "7 to 10-membered crosslinked heterocycle" include quinuclidine, 7-azabicyclo[2.2.1]heptane and the like.

The "heterocyclic group" is preferably 5 to 14-membered (preferably 5 to 10-membered) (monocyclic or bicyclic) heterocyclic group having, besides carbon atom, 1 or 2 kind(s) of preferably 1 to 4 hetero atom(s) selected from nitrogen atom, sulfur atom and oxygen atom. Specific examples include aromatic heterocyclic group such as 2-thienyl, 3-thienyl, 2-furyl, 3-furyl, 2-oxazolyl, 4-oxazolyl, 5-oxazolyl, 1,2,4-triazolyl, 1,2,3-triazolyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 2-pyrazinyl, 2-pyrimidinyl, 4-pyrimidinyl, 3-pyrrolyl, 1-imidazolyl, 2-imidazolyl, 4-imidazolyl, 5-imidazolyl, 3-pyridazinyl, 3-isothiazolyl, 3-isooxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like, nonaromatic heterocyclic group such as 1-pyrrolizinyl, 2-pyrrolizinyl, 3-pyrrolizinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino and the like, and the like.

Of these, 5 or 6-membered heterocyclic group having, besides carbon atom, 1 to 3 hetero atom(s) selected from nitrogen atom, sulfur atom and oxygen atom is more preferable. Specifically, 2-thienyl, 3-thienyl, 2-pyridyl, 3-pyridyl, 4-pyridyl, 2-furyl, 3-furyl, pyrazinyl, 2-pyrimidinyl, 3-pyrrolyl, 3-pyridazinyl, 3-isothiazolyl, 3-isooxazolyl, 1-pyrrolizinyl, 2-pyrrolizinyl, 3-pyrrolizinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino and the like are mentioned.

Examples of the "substituent" of the "optionally substituted heterocyclic group" are similar to the "substituent" of the aforementioned "optionally substituted hydrocarbon group" and the like.

The "heterocyclic group" may have 1 to 5, preferably 1 to 3, for example, the above-mentioned substituents at substitutable position(s). When the number of the substituents is two or more, the respective substituents may be the same or different.

In the present specification, the "acyl" is exemplified by acyl of the formula: —(C=O)—aR, —(C=O)—OaR, —(C=O)—NaRbR, —(C=S)—NHaR or —SO$_2$—cR wherein aR is hydrogen atom, optionally substituted hydrocarbon group or optionally substituted heterocyclic group, bR is hydrogen atom or $C_{1-6}$ alkyl, cR is optionally substituted hydrocarbon group or optionally substituted heterocyclic group, and the like.

The "$C_{1-6}$ alkyl" expressed by $R^{a10}$ and $R^{b14}$ is exemplified by methyl, ethyl, propyl, isopropyl, butyl, isobutyl, sec-butyl, tert-butyl, pentyl, hexyl and the like.

In the present specification, the "optionally substituted amino" is exemplified by (1) amino optionally having 1 or 2 substituent(s) and (2) optionally substituted cyclic amino.

The "substituent" of the "amino optionally having 1 or 2 substituent(s)" of the above-mentioned (1) is exemplified by optionally substituted hydrocarbon group, optionally substituted heterocyclic group, acyl and the like.

When the number of the "substituent(s)" of the above-mentioned "amino optionally having 1 or 2 substituent(s)" is two, the respective substituents may be the same or different.

The "cyclic amino" of the "optionally substituted cyclic amino" of the above-mentioned (2) is exemplified by 5 to 7-membered non-aromatic cyclic amino having, besides one nitrogen atom and carbon atom, 1 or 2 kind(s) of 1 to 4 hetero atom(s) selected from nitrogen atom, sulfur atom and oxygen atom. Specific examples thereof include pyrrolidin-1-yl, piperidino, piperazin-1-yl, morpholino, thiomorpholino, tetrahydroazepin-1-yl, imidazolidin-1-yl, 2,3-dihydro-1H-imidazol-1-yl, tetrahydro-1(2H)-pyrimidinyl, 3,6-dihydro-1(2H)-pyrimidinyl, 3,4-dihydro-1(2H)-pyrimidinyl and the like.

The "substituent" of the "optionally substituted cyclic amino" is exemplified by 1 to 3 from $C_{1-6}$ alkyl (e.g., methyl, ethyl, propyl, isopropyl, butyl, isobutyl, sec-butyl, tert-butyl, pentyl, hexyl etc.), $C_{6-14}$ aryl (e.g., phenyl, 1-naphthyl, 2-naphthyl, 2-biphenylyl, 3-biphenylyl, 4-biphenylyl, 2-anthryl etc.), $C_{1-6}$ alkylcarbonyl (e.g., acetyl, propionyl etc.), 5 to 10-membered aromatic heterocyclic group (e.g., 2-thienyl, 3-thienyl, 2-furyl, 3-furyl, 1,2,4-triazolyl, 1,2,3-triazolyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 2-pyrazinyl, 2-pyrimidinyl, 4-pyrimidinyl, 3-pyrrolyl, 1-imidazolyl, 2-imidazolyl, 4-imidazolyl, 5-imidazolyl, 3-pyridazinyl, 3-isothiazolyl, 3-isooxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.) and the like.

In the present specification, the "substituted amino" is exemplified by (1) amino having 1 or 2 substituent(s) and (2) substituted cyclic amino. As the "substituent" and "cyclic amino", the "substituent" and "cyclic amino" described in detail in the above-mentioned (1) and (2) are shown.

In the above-mentioned formula, "aromatic group" of the "optionally substituted aromatic group" represented by $Ar^c$ is exemplified by $C_{6-14}$ aryl, 5 to 14-membered aromatic heterocyclic group and the like.

As the "$C_{6-14}$ aryl", phenyl, naphthyl (e.g., 1-naphthyl, 2-naphthyl etc.), biphenylyl (e.g., 2-biphenylyl, 3-biphenylyl, 4-biphenylyl etc.), anthryl (e.g., 2-anthryl etc.) and the like are exemplified. Of these, phenyl is preferable.

The "5 to 14-membered aromatic heterocyclic group" is exemplified by 5 to 14-membered (preferably 5 to 10-membered) (monocyclic or bicyclic) aromatic heterocyclic group having, besides carbon atom, 1 or 2 kind(s) of preferably 1 to 4 hetero atom(s) selected from nitrogen atom, sulfur atom and oxygen atom. Specific examples include thienyl (e.g., 2-thienyl, 3-thienyl), furyl (e.g., 2-furyl, 3-furyl), pyridyl (e.g., 2-pyridyl, 3-pyridyl, 4-pyridyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazinyl, pyrimidinyl .(e.g., 2-pyrimidinyl, 4-pyrimidinyl), pyrrolyl (e.g., 3-pyrrolyl), imidazolyl (e.g., 2-imidazolyl), pyridazinyl (e.g., 3-pyridazinyl), isothiazolyl (e.g., 3-isothiazolyl), isooxazolyl (e.g., 3-isooxazolyl), indolyl (e.g., 1-indolyl, 2-indolyl, 3-indolyl), benzothiazolyl (e.g., 2-benzothiazolyl), benzothienyl (e.g., 2-benzo[b]thienyl, 3-benzo[b]thienyl), benzofuranyl (e.g., 2-benzo[b]furanyl, 3-benzo[b]furanyl) and the like.

The "substituent" of the aforementioned "optionally substituted $C_{6-14}$ aryl" is exemplified by 1 to 5 from halogen, hydroxy, optionally halogenated $C_{1-6}$ alkyl, optionally halogenated $C_{1-6}$ alkoxy and the like.

The "leaving group" represented by $X^a$ is exemplified by halogen (fluoro, chloro, bromo, iodo), alkylsulfonyloxy (e.g., $C_{1-6}$ alkylsulfonyloxy such as methylsulfonyloxy etc.), arylsulfonyloxy (e.g., $C_{6-14}$ arylsulfonyloxy optionally substituted by $C_{1-6}$ alkyl, such as p-toluenesulfonyloxy etc.) and the like.

The "substituent" of the "optionally substituted hydroxy" represented by $R^{a1}$ and $R^{a2}$, or $R^{b1}$, $R^{b2}$ and $R^{b3}$ is exemplified by those similar to the "substituent" of the aforementioned "optionally substituted hydrocarbon group" and the like.

The "substituent" of the "optionally substituted thiol" represented by $R^{a1}$ and $R^{a2}$, or $R^{b1}$, $R^{b2}$ and $R^{b3}$ is exemplified by those similar to the "substituent" of the aforementioned "optionally substituted hydrocarbon group" and the like.

The "substituent" of the "optionally substituted hydroxy" represented by $R^{a4}$, $R^{a5}$, $R^{a7}$ and $R^{a8}$ is exemplified by those similar to the "substituent" of the aforementioned "optionally substituted hydrocarbon group" and the like.

The "substituent" of the "optionally substituted thiol" represented by $R^{a4}$, $R^{a5}$ $R^{a7}$ and $R^{a8}$ is exemplified by those similar to the "substituent" of the aforementioned "optionally substituted hydrocarbon group" and the like.

The "aromatic group" of the "optionally substituted aromatic group" represented by $R^{a6}$ is exemplified by $C_{6-14}$ aryl, 5 to 14-membered heterocyclic group and the like.

Examples of the "$C_{6-14}$ aryl" include, phenyl, 1-naphthyl, 2-naphthyl, 2-anthryl and the like. Of these, phenyl is preferable.

The "5 to 14-membered heterocyclic group" is exemplified by 5 to 14-membered (preferably 5 to 10-membered) (monocyclic or bicyclic) heterocyclic group having, besides carbon atom, 1 or 2 kind(s) of preferably 1 to 4 hetero atom(s) selected from nitrogen atom, sulfur atom and oxygen atom. Specific examples include 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isooxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like.

The "substituent" of the "optionally substituted aromatic group" is exemplified by those similar to the "substituent" of the aforementioned "optionally substituted hydrocarbon group" and the like.

The "aromatic group" may have 1 to 5, preferably 1 to 3, for example, the above-mentioned substituents at substitutable position(s). When the number of the substituents is two or more, the respective substituents may be the same or different.

As the halogen represented by $R^{a7}$ and $R^{a8}$, for example, fluoro, chloro, bromo and iodo are mentioned.

As the halogen atom represented by $X^{a1}$, for example, chloro, bromo, iodo and the like are mentioned.

As the alkaline metal atom represented by $M^a$, for example, lithium, potassium, sodium and the like are mentioned, and as the alkaline earth metal, for example, calcium, magnesium and the like are mentioned.

When two of $R^{a1}$, $R^{a2}$ and $R^{a3}$ or two of $R^{b1}$, $R^{b2}$ and $R^{b3}$ form an optionally substituted ring together with the adjacent carbon atom, the compounds (aII) and (bII) are, for example, represented by the formula:

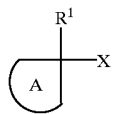

wherein A ring is an optionally substituted ring, $R^1$ is $R^{a1}$ or $R^{b1}$, and X is $X^a$ or —$NH_2$.

When three of $R^{a1}$, $R^{a2}$ and $R^{a3}$ or three of $R^{b1}$, $R^{b2}$ and $R^{b3}$ form an optionally substituted ring together with the adjacent carbon atom, the compounds (aII) and (bII) are represented by the formula:

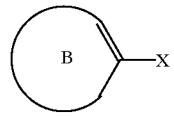

wherein B ring is an optionally substituted ring and other symbol is as defined above.

The "ring" of the "optionally substituted ring" formed by two or three of $R^{a1}$, $R^{a2}$ and $R^{a3}$ and two or three of $R^{b1}$, $R^{b2}$ and $R^{b3}$ is exemplified by 3 to 8-membered homocyclic ring or heterocyclic ring and the like.

As the "3 to 8-membered homocyclic ring", for example, $C_{3-8}$ cycloalkane such as cyclopropane, cyclobutane, cyclopentane, cyclohexane and the like, $C_{3-8}$ cycloalkene such as cyclopropene, cyclobutene, cyclopentene, cyclohexene and the like, $C_{3-8}$ cycloalkyne such as cycloheptyne, cyclooctyne and the like, benzene and the like are mentioned.

As the "3 to 8-membered heterocyclic", for example, 3 to 8-membered heterocyclic, such as aziridine, azetidine, morpholine, thiomorpholine, piperazine, piperidine, pyrrolidine, hexamethylenimine, hexamethylenimine, hexahydropyrimidine, pyridine, pyrimidine, oxazole, thiazole, quinoline, benzothiophene and the like are mentioned.

The "substituent" of the "optionally substituted ring" is exemplified by those similar to the "substituent" of the aforementioned "optionally substituted hydrocarbon group" and the like.

The "ring" may have 1 to 5, preferably 1 to 3, for example, the above-mentioned substituents at substitutable position(s). When the number of the substituents is two or more, the respective substituents may be the same or different.

The "halogen" represented by $X^{b1}$ and $X^{b2}$ is exemplified by fluoro, chloro, bromo and iodo.

The "substituent" of the "optionally substituted hydroxy" represented by $R^{b4}$, $R^{b5}$, $R^{b7}$ and $R^{b8}$ is exemplified by those similar to the "substituent" of the aforementioned "optionally substituted hydrocarbon group" and the like.

The "substituent" of the "optionally substituted thiol" represented by $R^{b4}$, $R^{b5}$, $R^{b7}$ and $R^{b8}$ is exemplified by those similar to the "substituent" of the aforementioned "optionally substituted hydrocarbon group" and the like.

The "alkyl" of the "optionally substituted alkyl" represented by $R^{b6}$ is exemplified by $C_{1-6}$ alkyl (e.g., methyl, ethyl, propyl, isopropyl, butyl, isobutyl, sec-butyl, tert-butyl, pentyl, hexyl etc.) and the like.

The "substituent" of the "optionally substituted alkyl" is exemplified by 1 to 5 from those similar to the "substituent" of the aforementioned "optionally substituted hydrocarbon group" and the like.

The "substituent" of the "optionally substituted phenyl" represented by $R^{b6}$ is exemplified by 1 to 5 from those similar to the "substituent" of the aforementioned "optionally substituted hydrocarbon group" and the like.

The "aromatic group" of the "optionally substituted aromatic group" represented by $R^{b9}$ is exemplified by $C_{6-14}$ aryl, 5 to 14-membered heterocyclic group and the like.

The "$C_{6-14}$ aryl" is exemplified by phenyl, 1-naphthyl, 2-naphthyl, 2-biphenylyl, 3-biphenylyl, 4-biphenylyl, 2-anthryl and the like. Of these, phenyl is preferable.

The "5 to 14-membered heterocyclic group" is exemplified by 5 to 14-membered (preferably 5 to 10-membered) (monocyclic or bicyclic) heterocyclic group having, besides carbon atom, 1 or 2 kind(s) of preferably 1 to 4 hetero atom(s) selected from nitrogen atom, sulfur atom and oxygen atom. Specific examples include 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isooxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like.

The "substituent" of the "optionally substituted aromatic group" is exemplified by those similar to the "substituent" of the aforementioned "optionally substituted hydrocarbon group" and the like.

The "aromatic group" may have 1 to 5, preferably 1 to 3, for example, the above-mentioned substituents at substitutable position(s). When the number of the substituents is two or more, the respective substituents may be the same or different.

The "substituent" represented by $R^{b11}$ is exemplified by those similar to the "substituent" of the aforementioned "optionally substituted hydrocarbon group" and the like.

The "alkylene" of the "optionally substituted alkylene" represented by $R^{b12}$ is exemplified by $C_{1-10}$ alkylene such as $-CH_2-$, $-(CH_2)_2-$, $-(CH_2)_3-$, $-(CH_2)_4-$, $-(CH_2)_5-$, $-(CH_2)_6-$, $-(CH_2)_7-$, $-(CH_2)_8-$ and the like.

The "substituent" of the "optionally substituted alkylene" is exemplified by 1 to 5, preferably 1 to 3, from those similar to the "substituent" of the aforementioned "optionally substituted hydrocarbon group" and the like. When the number of the substituents is two or more, the respective substituents may be the same or different.

The "alkenylene" of the "optionally substituted alkenylene" represented by $R^{b12}$ is exemplified by $C_{2-10}$ alkenylene such as $-CH=CH-$, $-CH_2-CH=CH-$, $-CH_2-CH=CH-CH_2-$, $-CH_2-CH_2-CH=CH-$, $-CH=CH-CH=CH-$, $-CH=CH-CH_2-CH_2-CH_2-$, $-CH=CH-CH=CH-CH_2-CH_2-$, $-CH=CH-CH=CH-CH=CH-$, $-CH=CH-CH_2-CH_2-CH_2-CH_2-CH_2-$, $-CH=CH-CH_2-CH_2-CH_2-CH_2-$, $-CH=CH-CH_2-CH_2-CH_2-$, $-CH=CH-CH_2-$, $-CH=CH-CH_2-CH_2-$, $-CH_2-CH_2-CH_2-CH_2-CH_2-$, $-CH=CH-$, $-CH=CH-CH_2-CH_2-CH_2-CH_2-$, $-CH=CH-$, $-CH=CH-CH=CH-CH_2-CH_2-$, $-CH=CH-$, $-CH=CH-CH=CH-CH=CH-$ and the like.

The "substituent" of the "optionally substituted alkenylene" is exemplified by 1 to 5, preferably 1 to 3, from those similar to the "substituent" of the aforementioned "optionally substituted hydrocarbon group" and the like. When the number of the substituents is two or more, the respective substituents may be the same or different.

The "alkynylene" of the "optionally substituted alkynylene" represented by $R^{b12}$ is exemplified by $C_{2-10}$ alkynylene such as $-C\equiv C-$, $-CH_2-C\equiv C-$, $-CH_2-C\equiv C-CH_2-CH_2-$ and the like.

The "substituent" of the "optionally substituted alkynylene" is exemplified by 1 to 5, preferably 1 to 3, from those similar to the "substituent" of the aforementioned "optionally substituted hydrocarbon group" and the like. When the number of the substituents is two or more, the respective substituents may be the same or different.

The "aromatic group" may have 1 to 5, preferably 1 to 3, for example, the above-mentioned substituents at substitutable position(s). When the number of the substituents is two or more, the respective substituents may be the same or different.

The "lower alkyl" represented by $R^{c1}$, $R^{c2}$, $R^{c3}$, $R^{c4}$ and $R^{c5}$ is explemplified by $C_{1-6}$ alkyl (e.g., methyl, ethyl, propyl, isopropyl, butyl, isobutyl, sec-butyl, tert-butyl, pentyl, hexyl etc.) and the like.

The "substituent" of the "optionally substituted phenyl", "optionally substituted benzyloxy" and "optionally substituted benzylamino", represented by $R^{c5}$ is exemplified by 1 to 5, preferably 1 to 3, from the "substituent" of the optionally substituted aromatic group represented by $Ar^c$ and the like. When the number of the substituents is two or more, the respective substituents may be the same or different.

The "halogen" represented by $X^{c1}$ and $X^{c2}$ is exemplified by fluorine, chlorine, bromine, iodine and the like.

The "metal" represented by $M^c$ is exemplified by alkali metal (e.g., lithium, sodium, potassium etc.), alkaline earth metal (e.g., magnesium, calcium etc.) and the like.

The reactive derivative of carboxylic acid is exemplified by acid halide (acetyl chloride, acetyl bromide etc.), acid anhydride (acetic anhydride etc.), and the like.

$R^{a1}$ is preferably hydrogen atom.

It is more preferable that $R^{a1}$ and $R^{a2}$ be hydrogen atoms.

$R^{a3}$ is preferably a group of the formula:

$$\left( \begin{array}{c} R^{a5} \;\; R^{a4} \\ \diagup\!\!\diagdown \\ R^{a6} \qquad m^a \end{array} \right)$$

wherein each symbol is as defined above.

More preferably, $R^{a4}$ and $R^{a5}$ are hydrogen atoms.

$R^{a6}$ is preferably phenyl optionally having substituent(s) (preferably $C_{1-6}$ alkoxy, particularly tert-butoxy).

$m^a$ is preferably 3 or 4.

$R^{a7}$ is preferably hydrogen atom.

$R^{a8}$ is preferably hydrogen atom.

$R^{b1}$ is preferably hydrogen atom.

It is more preferable that $R^{b1}$ and $R^{b2}$ be hydrogen atoms.

$R^{b3}$ is preferably a group of the formula:

$$\left( \begin{array}{c} R^{b7} \;\; R^{b8} \\ \diagup\!\!\diagdown \\ R^{b9} \qquad m^b \end{array} \right)$$

wherein each symbol is as defined above.

More preferably, $R^{b7}$ and $R^{b8}$ are hydrogen atoms.

$R^{b9}$ is preferably phenyl optionally having substituent(s) (preferably $C_{1-6}$ alkoxy).

$m^b$ is preferably 3.

$R^{b4}$ and $R^{b5}$ are preferably hydrogen atoms.

$R^{b6}$ is preferably phenyl optionally having substituent(s) (preferably alkyl).

$R^{b10}$ is preferably optionally substituted hydrocarbon group (preferably alkyl), more preferably $C_{1-3}$ alkyl.

$n^b$ is preferably 0.

$R^{b12}$ is preferably optionally substituted alkylene, more preferably trimethylene.

$Ar^c$ is preferably optionally substituted phenyl, more preferably 4-trifluoromethylphenyl.

$R^{c1}$ is preferably hydrogen atom.

$R^{c2}$ is preferably hydrogen atom.

$R^{c3}$ is preferably hydrogen atom.

$R^{c4}$ is preferably hydrogen atom.

$Y^c$ is preferably carbon atom.

$M^c$ is preferably alkali metal (e.g., lithium, sodium, potassium etc.).

$R^{c5}$ is preferably lower alkyl, more preferably methyl.

$n^c$ is preferably 4.

The compound (cIV) is a novel compound, which is specifically exemplified by 4-(acetoxymethyl)-2-[(E)-2-[4-(trifluoromethyl)phenyl]ethenyl]-1,3-oxazole and a salt thereof.

The salts of the compounds represented by the formulas (aIa), (aIb), (bI), (cI)-(cVII), (cIa), (cVa), (cVIIa) and the like in the specification are preferably pharmacologically acceptable salts, which are exemplified by salts with inorganic acids, salts with organic acids, salts with inorganic base, salts with organic base and the like.

Examples of the salts with inorganic acid include salts with hydrochloric acid, hydrobromic acid, nitric acid, sulfuric acid, phosphoric acid and the like.

Examples of the salts with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Examples of the salts with inorganic base include alkali metal salt such as sodium, potassium salt and the like; alkaline earth metal salt such as calcium salt, magnesium salt and the like; ammonium salt and the like.

Examples of the salts with organic base include salts with trimethylamine, triethylamine, pyridine, picoline, ethanolamine, diethanolamine, triethanolamine, dicyclohexylamine, N,N'-dibenzylethylenediamine and the like.

The production methods of compounds (aIa) and (aIb) useful as an intermediate for a 1-substituted-1,2,3-triazole compound having an inhibitory action on tyrosine kinases (especially HER2) are shown in the following.

When the compound (aII) and compound (aIII) are on the market, commercially available products thereof may be used as they are, or compound (aII) and compound (aIII) may be produced according to a method known per se, a method analogous thereto, and the like.

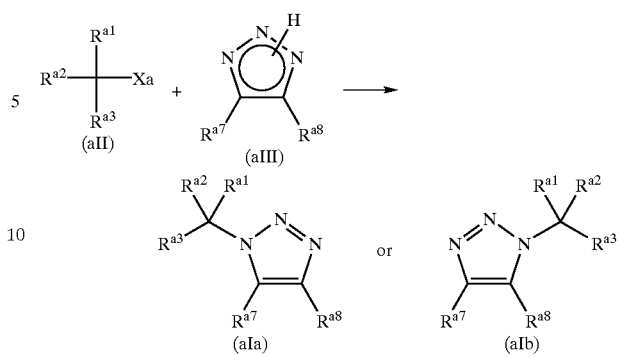

wherein each symbol is as defined above.

Reaction a1

The compound (aII) and compound (aIII) are reacted in secondary or tertiary alcohol in the presence of a base to give compound (aIa) or (aIb).

The amount of use of compound (aIII) is about 0.1–10 mol, preferably about 0.5–3.0 mol, per 1 mol of compound (aII).

The amount of use of the base is about 0.1–10 mol, preferably about 0.5–3.0 mol, per 1 mol of compound (aII).

Examples of the "base" include hydride of alkali metal or alkaline earth metal (e.g., lithium hydride, sodium hydride, potassium hydride, calcium hydride etc.), amide of alkali metal or alkaline earth metal (e.g., lithium amide, sodium amide, lithium diisopropylamade, lithium dicyclohexylamide, lithium hexamethyl disilazide, sodium hexamethyl disilazide, potassium hexamethyl disilazide etc.), hydroxide of alkali metal or alkaline earth metal (e.g., sodium hydroxide, potassium hydroxide, lithium hydroxide, calcium hydroxide etc.), metal hydrocarbon (e.g., butyllithium, tert-butyllithium etc.), lower alkoxide of alkali metal or alkaline earth metal (e.g., sodium methoxide, sodium ethoxide, potassium tert-butoxide etc.), carbonate of alkali metal or alkaline earth metal (e.g., sodium hydrogen carbonate, sodium carbonate, potassium carbonate etc.), organic bases [amines (e.g., triethylamine, diisopropylethylamine, N-methylmorpholine, dimethylaminopyridine, DBU (1,8-diazabicyclo[5.4.0] undec-7-ene), DBN (1,5-diazabicyclo[4.3.0]non-5-ene) etc.), organic base of basic heterocyclic compound (e.g., pyridine, imidazole, 2,6-lutidine etc.) etc.], and the like. Of these, hydroxide of alkali metal or alkaline earth metal is preferable.

Examples of the "secondary or tertiary alcohol" include secondary alcohol such as isopropyl alcohol, 2-butanol etc., tertiary alcohol such as tert-butanol, 2,-methyl-2-butanol etc., and the like. Of these, tertiary alcohol is preferable.

This reaction may be carried out in a solvent inert to the reaction, besides secondary or tertiary alcohol. Examples of the "inert solvent" include halogenated hydrocarbons (e.g., dichloromethane, chloroform, 1,2-dichloroethane, carbon tetrachloride etc.), aromatic hydrocarbons (e.g., benzene, toluene, xylene, chlorobenzene etc.), ethers (e.g., diethyl ether, diisopropy ether, tert-butylmethyl ether, diphenyl ether, tetrahydrofuran, dioxane, 1,2-dimethoxyethane, diglyme etc.), aliphatic hydrocarbons (e.g., hexane, pentane, cyclohexane etc.), amides (e.g., N,N-dimethylformamide, N,N-dimethylacetamide, 1-methyl-2-pyrrolidone, hexamethylphosphoric triamide etc.), sulfoxides (e.g., dimethyl sulfoxide etc.), primary alcohols (e.g., methanol, ethanol), nitrites (e.g., acetonitrile, propionitrile etc.), water, a mixture of two or more thereof and the like.

This reaction is carried out in the presence of an inorganic salt (e.g., halogenated alkali metal salt such as sodium iodide, sodium bromide, potassium iodide, potassium bromide etc.), where necessary.

The reaction temperature is generally from about 0° C. to 150° C., preferably from about 20° C. to 130° C. The reaction time is generally about 0.5 hour to 100 hours, preferably about 1 hour to 20 hours.

The compound (aIa) or (aIb) thus obtained can be isolated and purified from a reaction mixture by a known method, such as concentration, concentration under reduced pressure, solvent extraction, crystallization, recrystallization, phase transfer, chromatography and the like.

For example, a method comprising addition of an acid after the above-mentioned reaction, and isolation and purification to give a salt of compound (aIa) or (aIb) is preferably mentioned. Examples of the "acid" include mineral acids such as hydrochloric acid, hydrobromic acid, sulfuric acid etc., organic acids such as acetic acid, trifluoroacetic acid, tartaric acid, maleic acid, citric acid, methanesulfonic acid, p-toluenesulfonic acid etc., and the like. The amount of use of the "acid" is about 0.3–5.0 mol, preferably about 0.8–1.5 mol, per 1 mol of compound (aII).

Reaction a2

The compound (aII) and compound (aIII) are reacted in the absence of a base to give compound (aIa) or (aIb).

The amount of use of compound (aIII) is about 0.1–100 mol, preferably about 0.5–5 mol, per 1 mol of compound (aII).

This reaction is carried out in the presence of a solvent inert to the reaction. Examples of the "inert solvent" include halogenated hydrocarbons (e.g., dichloromethane, chloroform, 1,2-dichloroethane, carbon tetrachloride etc.), aromatic hydrocarbons (e.g., benzene, toluene, xylene, chlorobenzene etc.), ethers (e.g., diglyme, diethyl ether, diisopropy ether, tert-butylmethyl ether, diphenyl ether, tetrahydrofuran, dioxane, 1,2-dimethoxyethane etc.), aliphatic hydrocarbons (e.g., hexane, pentane, cyclohexane etc.), amides (e.g., N,N-dimethylformamide, N,N-dimethylacetamide, 1-methyl-2-pyrrolidone, hexamethylphosphoric triamide etc.), sulfoxides (e.g., dimethyl sulfoxide etc.), alcohols (e.g., methanol, ethanol, isopropyl alcohol, 2-butanol, tert-butanol, 2-methyl-2-butanol etc.), nitriles (e.g., acetonitrile, propionitrile etc.), water, a mixture of two or more thereof and the like. Of these, toluene, diglyme, N,N-dimethylformamide, dimethyl sulfoxide, 2-butanol, 2-methyl-2-butanol and the like are preferable.

Where necessary, this reaction is carried out in the presence of an inorganic salt (e.g., halogenated alkali metal salt such as sodium iodide, sodium bromide, potassium iodide, potassium bromide etc.).

The reaction temperature is generally from about 0° C. to 150° C., preferably from about 20° C. to 130° C. The reaction time is generally about 0.5 hour to 100 hours, preferably about 1 hour to 50 hours.

The compound (aIa) or (aIb) thus obtained can be isolated and purified from a reaction mixture by a known method, such as concentration, concentration under reduced pressure, solvent extraction, crystallization, recrystallization, phase transfer, chromatography and the like.

For example, a method comprising addition of an acid after the above-mentioned reaction, and isolation and purification to give a salt of compound (aIa) or (aIb) is preferably mentioned. Examples of the "acid" include mineral acids such as hydrochloric acid, hydrobromic acid, sulfuric acid etc., organic acids such as acetic acid, trifluoroacetic acid, tartaric acid, maleic acid, citric acid, methanesulfonic acid, p-toluenesulfonic acid etc., and the like. The amount of use of the "acid" is about 0.3–5.0 mol, preferably about 0.8–1.5 mol, per 1 mol of compound (aII).

Of the compounds (aIa) and (aIb), a salt of the compound of the formula

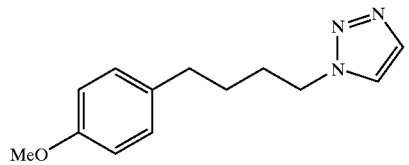

is novel. Examples of the "salt" include those similar to the salt of a compound of the above-mentioned formula (aIa). Of those, acid addition salts such as hydrochloride, methanesulfonic acid salt and the like are preferable.

Of the compounds (aIa) and (aIb), a compound of the formula (aIe) and a salt thereof are novel. Examples of the salt include those similar to the salt of a compound of the above-mentioned formula (aIa).

By deprotection of compound (aIe), a compound of the formula:

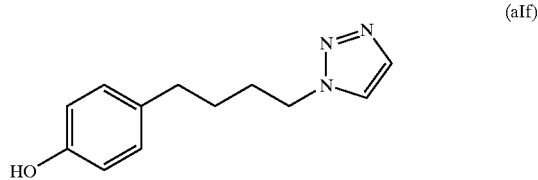

(aIf)

and a salt thereof can be produced. Examples of the salt include those similar to the salt of a compound of the above-mentioned formula (aIa). This deprotection can be carried out under mild conditions from among the general means of deprotecting protected hydroxy group, and is industrially advantageous. For example, compound (aIe) is reacted in the presence of an acid to remove t-butyl, which is a hydroxy protecting group according to a conventional method for deprotection. Examples of the "acid" include organic acids such as acetic acid, trifluoroacetic acid, trichloroacetic acid, tartaric acid, maleic acid, citric acid, methanesulfonic acid, toluenesulfonic acid and the like, and mineral acids such as sulfuric acid, hydrochloric acid, hydrobromic acid, chloric acid, perchloric acid, bromic acid, perbromic acid, iodic acid, periodic acid and the like. The solvent may be or may not be used. The acid may be or may not be diluted. When it is to be diluted, it is preferably diluted to 0.01 N–5 N. The reaction temperature is generally from 0° C. to 100° C., preferably from 20° C. to 70° C. The reaction time is generally about 0.1 hour to 5 hours, preferably about 0.1 hour to 2 hours.

The compound (aIe) can be produced by reacting, from among the compounds (aII), a compound [compound (aIIa)] wherein $R^{a1}$ and $R^{a2}$ are both hydrogen atoms and $R^{a3}$ is 3-[4-(tert-butoxyphenyl)]-propyl and triazole.

The compound (aIIa) can be produced by, for example, reacting compound (aII') and compound (aa), (ab), (ac) or (ad) under basic conditions. That is, by reacting compound (aII') and compound (aa) or (ab), a compound wherein $X^{a'}$ is halogen can be produced from among the compounds (aIIa), and by reacting compound (aII') and compound (ac), a compound wherein $X^{a'}$ is $OSO_2R^a$ can be produced from among the compounds (aIIa), and by reacting compound (aII') and compound (ad), a compound wherein $X^{a'}$ is $OCOR^a$ can be produced from among the compounds (aIIa). These reactions are all carried out under basic conditions. When a compound wherein $M^a$ is alkaline metal atom or alkaline earth metal atom is used as compound (aII'), a base does not need to be added, because they are basic, but when a compound wherein $M^a$ is hydrogen atom is used as compound (aII'), a base is generally added to the reaction mixture. Examples of the preferable "base" include tertiary amines such as trimethylamine, triethylamine, 1,8-diazabicyclo[5.4.0]-7-undecene etc., heterocyclic aromatic organic bases such as pyridine, picoline etc. and the like.

When compound (aII') and compound (aa) or (ab) are reacted, the reaction generally proceeds in a solvent inert to the reaction under basic conditions. Alternatively, the "base" may be used as a solvent. Examples of the "solvent" include halogenated hydrocarbons such as dichloromethane, dichloroethane and the like, aromatic hydrocarbons such as benzene, toluene, xylene and the like, ethers such as diethyl ether, diisopropy ether, tert-butylmethyl ether, tetrahydrofuran and the like, nitrites such as acetonitrile, propionitrile, isopropionitrile and the like, and esters such as ethyl acetate, isopropyl acetate and the like. The reaction temperature is generally from 0° C. to 100° C., preferably 10° C. to 70° C.

The compound (aII') and compound (ac) or (ad) can be reacted according to a conventional method, which proceeds in an organic solvent generally inert to the reaction under basic conditions. Alternatively, the "base" may be used as a solvent. Examples of the "organic solvent inert to the reaction" include halogenated hydrocarbons such as dichloromethane, dichloroethane and the like, aromatic hydrocarbons such as benzene, toluene, xylene and the like, ethers such as diethyl ether, diisopropy ether, tert-butylmethyl ether, tetrahydrofuran and the like, nitrites such as acetonitrile, propionitrile, isopropionitrile and the like, esters such as ethyl acetate, isopropyl acetate and the like, and the like. The reaction is generally carried out by cooling a solution containing compound (aII') to a temperature of not more than 10° C., adding dropwise compound (aa) thereto with stirring and reacting the mixture at 5–20° C. for 10 min–6 hours.

Of the compounds (aIIa), a compound wherein $X^{a'}$ is $OSO_2R^a$ or $OCOR^a$ is further reacted with halogen compound to produce a compound wherein $X^{a'}$ is halogen from among the compounds (aIIa).

By reacting halogen compound with sulfonyloxy compound [compound wherein $X^{a'}$ is $OSO_2R^a$ in the formula (aIIa)] produced by reacting the above-mentioned (aII') and compound (ac), a compound wherein $X^{a'}$ is halogen in the formula (aIIa) can be produced. Generally, the above-mentioned sulfonyloxy compound is reacted with halogen compound [e.g., alkali halide (e.g., sodium chloride, potassium chloride, sodium bromide, potassium bromide, sodium iodide, potassium iodide etc.), pyridinium halide (pyridinium chloride, pyridinium bromide, pyridinium iodide etc.), hydrogen halide (e.g., hydrochloric acid, hydrobromic acid, hydriodic acid etc.), hydrogen halide salt of tertiary amine (e.g., trimethylamine hydrochloride, trimethylamine hydrobromide, triethylamine hydrochloride, triethylamine hydrobromide etc.) and the like] in a solvent in the presence of a base [inorganic base (e.g., alkali metal such as sodium, potassium etc.; alkaline earth metal such as calcium, magnesium etc.; hydroxide such as ammonium etc.) or an organic base (e.g., trimethylamine, triethylamine, pyridine, picoline etc.)]. Alternatively, by reacting compound (aII') and a compound, wherein X is $OSO_2R^a$ from among the compounds (ac), and then reacting the resulting compound with halogen compound, compound (aIIa) wherein $X^{a'}$ is halogen can be also produced. The solvent only needs to be inert. Examples thereof include chain or cyclic ethers such as diethyl ether, diisopropy ether, tert-butylmethyl ether, tetrahydrofuran and the like, chain alcohols having 1 to 5 carbon atoms, such as methanol, ethanol, isopropyl alcohol and the like, ketones such as acetone, 2-butanone, 2-pentanone, 3-pentanone and the like, ethers such as diethyl ether, diisopropy ether, tert-butylmethyl ether, tetrahydrofuran and the like, nitrites such as acetonitrile, propionitrile, isopropionitrile and the like, esters such as ethyl acetate, isopropyl acetate and the like, amides such as N,N-dimethylacetamide, N,N-dimethylacetamide, N-methylpyrrolidone and the like, and the like. Alternatively, the "base" may be used alone as a solvent. The reaction temperature is from room temperature to the boiling point of the solvent, preferably from 25° C. to the boiling point of the solvent. The reaction can be generally terminated upon confirmation of decrease in the starting materials by a typical analytical method.

The compound (aIIa) obtained in this way is novel.

Of the compounds (aIa) and (aIb), for example, a compound of the formula

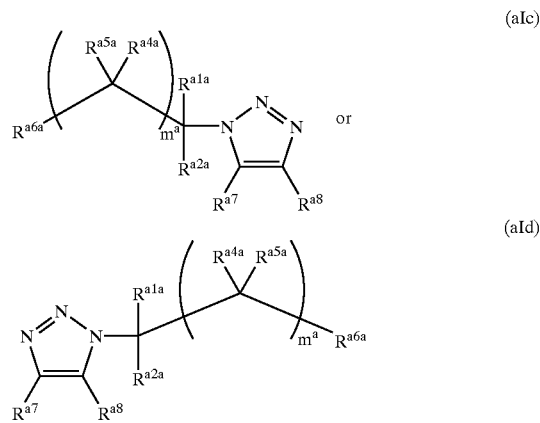

wherein $R^{a1a}$, $R^{a2a}$, $R^{a4a}$ and $R^{a5a}$ are each a hydrogen atom, $R^{a6a}$ is phenyl having (i) optionally substituted hydroxy or (ii) optionally substituted thiol as a substituent, and other symbols are as defined above, and a salt thereof can be converted to a 1-substituted-1,2,3-triazole compound useful as a pharmaceutical agent and the like, according to a method known per se, such as a method described in JP-A-11-60571 or a method analogous thereto.

The "optionally substituted hydroxy" of the "phenyl substituted by optionally substituted hydroxy" represented by $R^{a6a}$ is exemplified by those similar to the aforementioned "optionally substituted hydroxy" represented by $R^{a4}$ or $R^{a5}$.

The "optionally substituted thiol" of the "phenyl substituted by optionally substituted thiol" represented by $R^{a6a}$ is exemplified by those similar to the aforementioned "optionally substituted thiol" represented by $R^{a4}$, $R^{a5}$, $R^{a7}$ or $R^{a8}$.

For example, compound (aIc) or (aId) is subjected to deprotection known per se, where necessary, then reacted with a compound of the formula $$R^{a12}-(CH_2)_{qa}-W^a$$

wherein $R^{a12}$ is an optionally substituted aromatic heterocyclic group, qa is an integer of 1 to 5, and $W^a$ is a leaving group, or a salt thereof [hereinafter to be briefly referred to as compound (aIV)] to give a compound of the formula

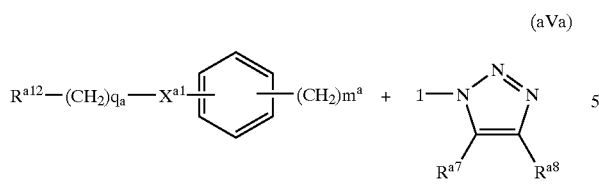

(aVa)

or

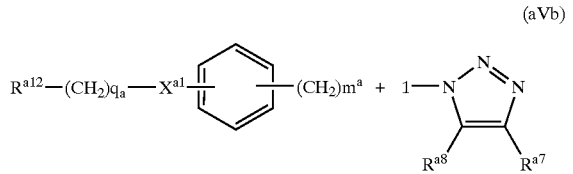

(aVb)

wherein $X^{a1}$ is an oxygen atom or a sulfur atom, and other symbols are as defined above, or a salt thereof.

When the compound (aIV) is on the market, a commercially available product thereof may be used as it is, or compound (aIV) may be produced according to a method known per se, a method analogous thereto, and the like.

The "leaving group" represented by $W^a$ is exemplified by those similar to the "leaving group" represented by $X^a$ and the like.

The "aromatic heterocyclic group" of the "optionally substituted aromatic heterocyclic group" represented by $R^{a12}$ is exemplified by 5 to 14-membered (preferably 5 to 10-membered) (monocyclic or bicyclic) heterocyclic group, having, besides carbon atom, 1 or 2 kind(s) of preferably 1 to 4 hetero atom(s) selected from nitrogen atom, sulfur atom and oxygen atom. Examples thereof include 2-thienyl, 3-thienyl, 2-furyl, 3-furyl, 2-oxazolyl, 4-oxazolyl, 5-oxazolyl, 1,2,4-triazolyl, 1,2,3-triazolyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 2-pyrazinyl, 2-pyrimidinyl, 4-pyrimidinyl, 3-pyrrolyl, 1-imidazolyl, 2-imidazolyl, 4-imidazolyl, 5-imidazolyl, 3-pyridazinyl, 3-isothiazolyl, 3-isooxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like. Preferred is oxazolyl such as 2-oxazolyl, 4-oxazolyl, 5-oxazolyl and the like.

The "substituent" of the "optionally substituted aromatic heterocyclic group" represented by $R^{a12}$ is exemplified by 1 to 5 from "optionally substituted hydroxy", "optionally substituted thiol", "optionally substituted amino", "optionally substituted hydrocarbon group", "optionally substituted heterocyclic group" and "acyl" represented by $R^{a4}$ and $R^{a5}$. Of these, optionally substituted hydrocarbon group is preferable and $C_{2-6}$ alkenylene substituted by optionally substituted $C_{6-14}$ aryl is more preferable.

Reaction b1

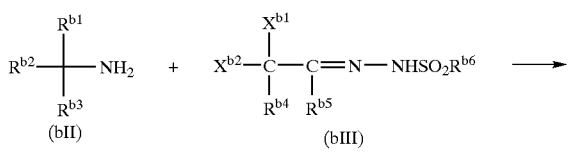

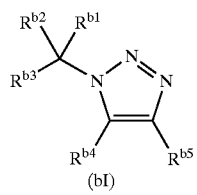

(bI)

wherein each symbol is as defined above.

The compound (bII) and compound (bIII) are reacted and the reaction mixture is treated with a base to give compound (bI).

When the compound (bII) is on the market, a commercially available product thereof may be used as it is, or compound (bII) may be produced according to a method known per se, a method analogous thereto, the method of Reaction B to be mentioned later and the like.

When the compound (bIII) is on the market, a commercially available product thereof may be used as it is, or compound (bIII) may be produced according to a method known per se, a method analogous thereto, and the like.

The amount of use of compound (bIII) is about 0.1–10 mol, preferably about 0.5–3.0 mol, per 1 mol of compound (bII).

The reaction of compound (bII) and compound (bIII) is preferably carried out in a solvent inert to the reaction. Examples of the "inert solvent" include halogenated hydrocarbons (e.g., dichloromethane, chloroform, 1,2-dichloroethane, carbon tetrachloride etc.), aromatic hydrocarbons (e.g., benzene, toluene, xylene, chlorobenzene etc.), ethers (e.g., diethyl ether, diisopropy ether, tert-butylmethyl ether, diphenyl ether, tetrahydrofuran, dioxane, 1,2-dimethoxyethane etc.), aliphatic hydrocarbons (e.g., hexane, pentane, cyclohexane etc.), alcohols (e.g., methanol, ethanol, isopropylalcohol, 2-butanol, tert-butanol, 2-methyl-2-butanol etc.), amides (e.g., N,N-dimethylformamide, N,N-dimethylacetamide, 1-methyl-2-pyrrolidone, hexamethylphosphoric triamide etc.), sulfoxides (e.g., dimethyl sulfoxide etc.), nitriles (e.g., acetonitrile, propionitrile etc.), water, a mixture of two or more thereof and the like. Of these, methanol is preferable.

The reaction temperature is generally from about 0° C. to 150° C., preferably from about 10 to 80° C. The reaction time is generally from about 0.2 hour to 20 hours, preferably from about 0.5 hour to 3 hours.

Then the reaction mixture is treated with a base to give compound (bI).

The treatment with a base generally includes mixing the reaction mixture with a base, or concentration of the reaction mixture followed by mixing of the concentrate with a base.

The amount of use of the base is about 0.1–500 mol, preferably about 1–200 mol, per 1 mol of compound (bII).

Examples of the "base" include hydride of alkali metal or alkaline earth metal (e.g., lithium hydride, sodium hydride, potassium hydride, calcium hydride etc.), amide of alkali metal or alkaline earth metal (e.g., lithium amide, sodium amide, lithium diisopropylamide, lithium dicyclohexylamide, lithium hexamethyl disilazide, sodium hexamethyl disilazide, potassium hexamethyl disilazide etc.), lower alkoxide of alkali metal or alkaline earth metal (e.g., sodium methoxide, sodium ethoxide, potassium tert-butoxide etc.), carbonate of alkali metal or alkaline earth metal (e.g., sodium carbonate, potassium carbonate etc.), hydrogencarbonate of alkali metal or alkaline earth metal (e.g., sodium hydrogen carbonate, potassium hydrogen carbonate etc.), hydroxide of alkali metal or alkaline earth metal (e.g., sodium hydroxide, potassium hydroxide, lithium hydroxide, calcium hydroxide), metal hydrocarbon (n-butyl lithium, tert-butyl lithium), organic bases [amines (e.g., triethylamine, diisopropylethylamine, N-methylmorpholine, dimethylaminopyridine, DBU (1,8-diazabicyclo [5.4.0] undec-7-ene), DBN (1,5-diazabicyclo[4.3.0]non-5-ene) etc.), organic base of basic heterocyclic compound (e.g., pyridine, imidazole, 2,6-lutidine etc.) etc.], and the like. Of these, hydrogencarbonate of alkali metal or alkaline earth metal is preferable. More preferred is sodium hydrogen carbonate.

The base may be used as it is or used after dissolving in an inert solvent. Examples of the "inert solvent" include the aforementioned "inert solvent".

The temperature for treatment with a base is generally about 0–70° C., preferably about 10–40° C. The reaction mixture may be left standing or stirred or immediately subjected to isolation and purification of compound (bI) after addition of a base. When the reaction mixture is stood or stirred, the time of standing or stirring is generally about 0.01–5 hour, preferably about 0.1–2 hours.

The compound (bI) thus obtained can be isolated and purified from a reaction mixture by a known method, such as concentration, concentration under reduced pressure, solvent extraction, crystallization, recrystallization, phase transfer, chromatography and the like.

Of the compounds (bI), for example, a compound of the formula

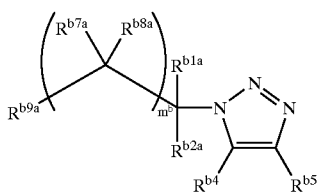

(bIa)

wherein $R^{b1a}$, $R^{b2a}$, $R^{b7a}$ and $R^{b8a}$ are each a hydrogen atom, $R^{b9a}$ is phenyl having (i) optionally substituted hydroxy or (ii) optionally substituted thiol as substituent(s), and other symbols are as defined above, and a salt thereof can be converted to a 1-substituted-1,2,3-triazole compound useful as a pharmaceutical agent and the like, according to a method known per se, such as a method described in JP-A-11-60571 or a method analogous thereto.

The "optionally substituted hydroxy" of the "phenyl substituted by optionally substituted hydroxy" represented by $R^{b9a}$ is exemplified by those similar to the aforementioned "optionally substituted hydroxy" represented by $R^{b4}$ or $R^{b5}$ and the like.

The "optionally substituted thiol" of the "phenyl substituted by optionally substituted thiol" represented by $R^{b9a}$ is exemplified by those similar to the aforementioned "optionally substituted thiol" represented by $R^{b4}$, $R^{b5}$, $R^{b8}$ and the like.

For example, compound (bIa) is subjected to deprotection known per se, where necessary, and reacted with a compound of the formula $$R^{b16}-(CH_2)_{qb}-W^b$$

wherein $R^{b16}$ is an optionally substituted aromatic heterocyclic group, qb is an integer of 1 to 5, and $W^b$ is a leaving group, or a salt thereof [hereinafter to be briefly referred to as compound (bIX)] to give a compound of the formula

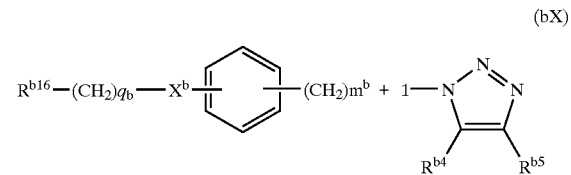

(bX)

wherein $X^b$ is an oxygen atom or sulfur atom, and other symbols are as defined above, or a salt thereof.

When the compound (bIX) is on the market, a commercially available product thereof may be used as it is, or compound (bIX) may be produced according to a method known per se, a method analogous thereto, and the like.

Examples of the "leaving group" represented by $W^b$ include halogen (fluoro, chloro, bromo, iodo), alkylsulfonyloxy (e.g., $C_{1-6}$ alkylsulfonyloxy such as methylsulfonyloxy etc.), arylsulfonyloxy (e.g., $C_{6-14}$ arylsulfonyloxy optionally substituted by $C_{1-6}$ alkyl, such as p-toluenesulfonyloxy etc.) and the like.

The "aromatic heterocyclic group" of the "optionally substituted aromatic heterocyclic group" represented by $R^{b16}$ is exemplified by 5 to 14-membered (preferably 5 to 10-membered) (monocyclic or bicyclic) heterocyclic group having, besides carbon atom, 1 or 2 kind(s) of preferably 1 to 4 hetero atom(s) selected from nitrogen atom, sulfur atom and oxygen atom and the like. Specific examples thereof include 2-thienyl, 3-thienyl, 2-furyl, 3-furyl, 2-oxazolyl, 4-oxazolyl, 5-oxazolyl, 1,2,4-triazolyl, 1,2,3-triazolyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 2-pyrazinyl, 2-pyrimidinyl, 4-pyrimidinyl, 3-pyrrolyl, 1-imidazolyl, 2-imidazolyl, 4-imidazolyl, 5-imidazolyl, 3-pyridazinyl, 3-isothiazolyl, 3-isooxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like. Preferred is oxazolyl such as 2-oxazolyl, 4-oxazolyl, 5-oxazolyl and the like.

The "substituent" of the "optionally substituted aromatic heterocyclic group" represented by $R^{b16}$ is exemplified by 1 to 5 from the aforementioned "optionally substituted hydroxy", "optionally substituted thiol", "optionally substituted amino", "optionally substituted hydrocarbon group", "optionally substituted heterocyclic group", "acyl" and the like represented by $R^{b4}$ or $R^{b5}$. Of these, optionally substituted hydrocarbon group is preferable, and $C_{2-6}$ alkenylene substituted by optionally substituted $C_{6-14}$ aryl is more preferable.

The amine compound such as compound (bII) can be also produced according to the method of the following Reaction b2.

Reaction b2

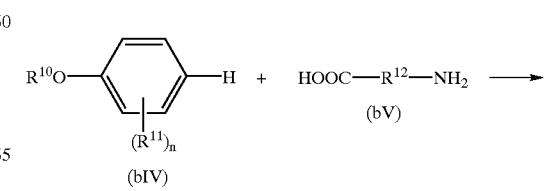

-continued $$R^{b10}O-\underset{(R^{b11})_{n^b}}{\underset{|}{\text{C}_6H_3}}-CO-R^{12}-NH_2 \longrightarrow$$

(bVI)

$$R^{b10}O-\underset{(R^{b11})_{n^b}}{\underset{|}{\text{C}_6H_3}}-CH_2-R^{b12}-NH_2$$

(bVII)

wherein each symbol is as defined above.

The compound (bIV) and compound (bV) are reacted to give compound (bVI), which is then subjected to reduction to give the objective amine compound [compound (bVII)].

In the reaction of compound (bIV) and compound (bV), the amount of use of compound (bV) is about 0.1–10 mol, preferably about 1–2 mol, per 1 mol of compound (bIV).

The reaction of compound (bIV) and compound (bV) is carried out in the presence of an acid on demand.

Examples of the "acid" include Lewis acid (e.g., anhydrous aluminum chloride, zinc chloride, tin chloride etc.), and strong acid (e.g., sulfuric acid, methanesulfonic acid, trifluoromethanesulfonic acid etc.).

The amount of use of the "acid" is about 0.1–100 mol, preferably about 1–10 mol, per 1 mol of compound (bIV).

The reaction of compound (bIV) and compound (bV) is carried out without solvent or in a solvent inert to the reaction. Examples of the "inert solvent" include halogenated hydrocarbons (e.g., dichloromethane, chloroform, 1,2-dichloroethane, carbon tetrachloride etc.), aromatic hydrocarbons (e.g., benzene, toluene, xylene, chlorobenzene etc.), ethers (e.g., diethyl ether, diisopropy ether, tert-butylmethyl ether, diphenyl ether, tetrahydrofuran, dioxane, 1,2-dimethoxyehtane etc.), aliphatic hydrocarbons (e.g., hexane, pentane, cyclohexane etc.), amides (e.g., N,N-dimethylformamide, N,N-dimethylacetamide, 1-methyl-2-pyrrolidone, hexamethylphosphoric triamide etc.), sulfoxides (e.g., dimethyl sulfoxide etc.), nitriles (e.g., acetonitrile, propionitrile etc.) and a mixture of two or more of these. Preferably, the reaction is carried out without solvent.

The reaction temperature is generally from about −100° C. to 200° C., preferably from about 0° C. to 100° C. The reaction time is generally about 0.1 hour to 50 hours, preferably about 0.5 hour to 10 hours.

The compound (bVI) thus obtained can be used in the next reaction as a reaction mixture or as a crude product. It is also possible to isolate the compound from the reaction mixture according to a conventional method and the compound can be easily purified by a separation means such as recrystallization, distillation, chromatography and the like.

Of the compounds (bVI), trifluoromethanesulfonic acid salt of the compound of the formula $$R^{b10}O-\underset{(R^{b11})_{n^b}}{\underset{|}{\text{C}_6H_3}}-CO-R^{b12}-NH_2$$

wherein $R^{b12}$ is trimethylene and other symbols are as defined above, is novel.

The compound (bVI) is reduced to give compound (bVII).

The reduction can be carried out according to catalytic reduction known per se. The compound (bVI) and a catalytic amount of a metal catalyst (e.g., Raney-nickel, platinum oxide, metal palladium, palladium-carbon etc.) are reacted in an inert solvent under hydrogen pressure of 0–100 atm, preferably 0–5 atm.

Examples of the "inert solvent" include halogenated hydrocarbons (e.g., dichloromethane, chloroform, 1,2-dichloroethane, carbon tetrachloride etc.), aromatic hydrocarbons (e.g., benzene, toluene, xylene, chlorobenzene etc.), ethers (e.g., diethyl ether, diisopropy ether, tert-butylmethyl ether, diphenyl ether, tetrahydrofuran, dioxane, 1,2-dimethoxyethane etc.), aliphatic hydrocarbons (e.g., hexane, pentane, cyclohexane etc.), alcohols (e.g., methanol, ethanol, isopropylalcohol, 2-butanol, tert-butanol, 2-methyl-2-butanol etc.), amides (e.g., N,N-dimethylformamide, N,N-dimethylacetamide, 1-methyl-2-pyrrolidone, hexamethylphosphoric triamide etc.), sulfoxides (e.g., dimethyl sulfoxide etc.), nitriles (e.g., acetonitrile, propionitrile etc.), organic acids (e.g., acetic acid etc.), water, a mixture of two or more thereof and the like. Of these, ethers, acetic acid and the like are preferable.

The reaction temperature is from 0° C. to 100° C., preferably from 20° C. to 70° C. The reaction time is generally about 0.5 hour to 100 hours, preferably about 1 hour to 50 hours.

The compound (bVII) thus obtained can be used in the next reaction as a reaction mixture or as a crude product. It is also possible to isolate the compound from the reaction mixture according to a conventional method and the compound can be easily purified by a separation means such as recrystallization, distillation, chromatography and the like.

The compound (bVII) can be converted to compound (bVIII) useful as an intermediate for a 1-substituted-1,2,3-triazole compound having a tyrosine kinase (especially, HER2) inhibitory action, by reacting the compound with compound (bIII).

Reaction b3

(bVII) + (bIII) ⟶

$$R^{b10}O-\underset{(R^{b11})_{n^b}}{\underset{|}{\text{C}_6H_3}}-CH_2-R^{b12}-\underset{R^{b4}\quad R^{b5}}{\underset{|}{\text{N}}}\begin{smallmatrix}N\\\parallel\\N\end{smallmatrix}$$

(bVIII)

wherein each symbol is as defined above.

The reaction of compound (bVII) and compound (bIII) can be carried out under the reaction conditions detailed in the aforementioned reaction b1.

The compound (bVIII) thus obtained can be isolated and purified from a reaction mixture by a known method, such as concentration, concentration under reduced pressure, solvent extraction, crystallization, recrystallization, phase transfer, chromatography and the like.

Of the compounds (bVIII), for example, a compound of the formula (bVIIIa)

$$R^{b10}O-\underset{(R^{b11})_{n^b}}{\underset{|}{\text{C}_6H_3}}-CH_2-R^{b12a}-\underset{R^{b4}\quad R^{b5}}{\underset{|}{\text{N}}}\begin{smallmatrix}N\\\parallel\\N\end{smallmatrix}$$

wherein $R^{b12a}$ is $C_{1-10}$ alkylene and other symbols are as defined above, or a salt thereof can be converted to a 1-substituted-1,2,3-triazole compound useful as a pharmaceutical agent and the like, according to a method known per se, such as a method described in JP-A-11-60571 or a method analogous thereto.

For example, compound (bVIIIa) is subjected to deprotection reaction known per se, and reacted with compound (bIX) to give a compound of the formula

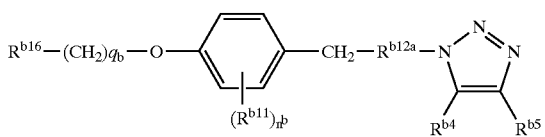

(bXI)

wherein each symbol is as defined above, or a salt thereof.

The production method of compound (cIV) useful as an intermediate for the production of an oxazole compound (cVII) having a tyrosine kinase (especially, HER2) inhibitory action is described in the following.

Reaction c1

A reaction mixture of compound (cI) and compound (cII) is reacted with compound (cIII) to give compound (cIV).

When the compound (cI) is on the market, a commercially available product thereof may be used as it is, or compound (cI) may be produced according to a method known per se, a method analogous thereto, and the like.

When the compound (cII) is on the market, a commercially available product thereof may be used as it is, or compound (cII) may be produced according to a method known per se, a method analogous thereto, and the like.

When the compound (cIII) is on the market, a commercially available product thereof may be used as it is, or compound (cIII) may be produced according to a method known per se, a method analogous thereto, and the like.

Preferably, the reaction of compound (cI) and compound (cII) is carried out in the presence of an acid or a base and, where desired, in a solvent inert to the reaction.

The amount of use of compound (cII) is about 0.1–10 equivalents, preferably about 1–3 equivalents, relative to compound (cI).

The amount of use of acid is about 0.01–10 equivalents, preferably about 0.01–3 equivalents, relative to compound (cI).

The amount of use of base is about 0.01–10 equivalents, preferably about 0.01–3 equivalents, relative to compound (cI).

Examples of the "acid" include hydrochloric acid, sulfuric acid, trifluoromethanesulfonic acid, trifluoroacetic acid and the like.

Examples of the "base" include carbonate of alkali metal or alkaline earth metal (e.g., sodium carbonate, potassium carbonate etc.), hydrogencarbonate of alkali metal or alkaline earth metal (e.g., sodium hydrogen carbonate, potassium hydrogen carbonate etc.), hydroxide of alkali metal or alkaline earth metal (e.g., sodium hydroxide, potassium hydroxide, lithium hydroxide, calcium hydroxide) and the like.

Examples of the "inert solvent" include aliphatic hydrocarbons (e.g., hexane, pentane, cyclohexane etc.), aromatic hydrocarbons (e.g., benzene, toluene, xylene, chlorobenzene etc.), ethers (e.g., diethyl ether, diisopropy ether, tert-butylmethyl ether, diphenyl ether, tetrahydrofuran, dioxane, 1,2-dimethoxyethane etc.), halogenated hydrocarbons (e.g., dichloromethane, chloroform, 1,2-dichloroethane, carbon tetrachloride etc.), esters (e.g., ethyl acetate etc.), ketones (e.g., acetone, methyl ethyl ketone etc.), nitrites (e.g., acetonitrile, propionitrile etc.), sulfoxides (e.g., dimethyl sulfoxide etc.), amides (e.g., N,N-dimethylformamide, N,N-dimethylacetamide, N-methylpyrrolidone, hexamethylphosphoric triamide etc.), alcohols (e.g., methanol, ethanol, isopropyl alcohol, 2-butanol, tert-butanol, 2-methyl-2-butanol etc.), water, a mixture of two or more thereof and the like. Of these, aromatic hydrocarbons such as toluene, xylene and the like are preferable.

The reaction temperature is generally from about 0° C. to 200° C., preferably from about 20° C. to 160° C. The reaction time is generally about 1 hour to 48 hours, preferably about 1 hour to 24 hours.

The reaction of compound (cIII) and a reaction mixture of compound (cI) and compound (cII) is preferably carried out in the presence of a base and(or) a phase transfer catalyst and in a solvent inert to the reaction, where desired.

The compound (cIII) may be an anhydride or hydrate.

The amount of use of compound (cIII) is about 0.1–10 equivalents, preferably about 1–8 equivalents, relative to compound (cI).

The amount of use of base is about 0.1–10 equivalents, preferably about 1–8 equivalents, relative to compound (cI).

The amount of use of the phase transfer catalyst is about 0.01–1 equivalent, preferably about 0.01–0.3 equivalent, relative to compound (cI).

Examples of the "base" include carbonate of alkali metal or alkaline earth metal (e.g., sodium carbonate, potassium carbonate etc.), hydrogencarbonate of alkali metal or alkaline earth metal (e.g., sodium hydrogen carbonate, potassium hydrogen carbonate etc.), hydroxide of alkali metal or alkaline earth metal (e.g., sodium hydroxide, potassium hydroxide, lithium hydroxide, calcium hydroxide) and the like.

Examples of the "phase transfer catalyst" include tetra(n-butyl)ammonium bromide, tetra(n-butyl)ammonium hydrogensulfate and the like.

Examples of the "inert solvent" include aliphatic hydrocarbons (e.g., hexane, pentane, cyclohexane etc.), aromatic hydrocarbons (e.g., benzene, toluene, xylene, chlorobenzene etc.), ethers (e.g., diethyl ether, diisopropy ether, tert-butylmethyl ether, diphenyl ether, tetrahydrofuran, dioxane, 1,2-dimethoxyethane etc.), halogenated hydrocarbons (e.g., dichloromethane, chloroform, 1,2-dichloroethane, carbon tetrachloride etc.), esters (e.g., ethyl acetate etc.), ketones (e.g., acetone, methyl ethyl ketone etc.), nitrites (e.g., acetonitrile, propionitrile etc.), sulfoxides (e.g., dimethyl sulfoxide etc.), amides (e.g., N,N-dimethylformamide, N,N-dimethylacetamide, N-methylpyrrolidone, hexamethylphosphoric triamide etc.), alcohols (e.g., methanol, ethanol, isopropyl alcohol, 2-butanol, tert-butanol, 2-methyl-2-butanol etc.), water, a mixture of two or more thereof and the like. Of these, dimethyl sulfoxide, N,N-dimethylformamide, N-methylpyrrolidone and the like are preferable.

The reaction temperature is generally from about 0° C. to 150° C., preferably from about 20° C. to 130° C. The reaction time is generally about 1 hour to 24 hours, preferably about 1 hour to 12 hours.

The compound (cIV) thus obtained can be isolated and purified from a reaction mixture by a known method, such as concentration, concentration under reduced pressure, solvent extraction, crystallization, recrystallization, phase transfer, chromatography and the like.

In the above-mentioned reaction, the reaction product from compound (cI) and compound (cII) can be isolated from the reaction mixture according to a conventional method, but preferably, the reaction product is subjected to the next step without isolation.

The compound (cIV) can be converted to compound (cVII) useful as a pharmaceutical agent and the like, for example, according to the following Reactions c2 and c3.

Reaction c2

The compound (cIV) is subjected to hydrolysis or catalytic reduction to give compound (cV).

For "hydrolysis", compound (cIV) and a base are reacted in an inert solvent.

The amount of use of base is about 0.1–10 equivalents, preferably 1–5 equivalents, relative to compound (cIV).

Examples of the "base" include carbonate of alkali metal or alkaline earth metal (e.g., sodium carbonate, potassium carbonate etc.), hydroxide of alkali metal or alkaline earth metal (e.g., sodium hydroxide, potassium hydroxide, lithium hydroxide, calcium hydroxide) and the like.

Examples of the "inert solvent" include aliphatic hydrocarbons (e.g., hexane, pentane, cyclohexane etc.), aromatic hydrocarbons (e.g., benzene, toluene, xylene, chlorobenzene etc.), ethers (e.g., diethyl ether, diisopropy ether, tert-butylmethyl ether, diphenyl ether, tetrahydrofuran, dioxane, 1,2-dimethoxyethane etc.), halogenated hydrocarbons (e.g., dichloromethane, chloroform, 1,2-dichloroethane, carbon tetrachloride etc.), esters (e.g., ethyl acetate etc.), ketones (e.g., acetone, methyl ethyl ketone etc.), nitriles (e.g., acetonitrile, propionitrile etc.), sulfoxides (e.g., dimethyl sulfoxide etc.), amides (e.g., N,N-dimethylformamide, N,N-dimethylacetamide, N-methylpyrrolidone, hexamethylphosphoric triamide etc.), alcohols (e.g., methanol, ethanol, isopropyl alcohol, 2-butanol, tert-butanol, 2-methyl-2-butanol etc.), water, a mixture of two or more thereof and the like. Preferred are methanol and dimethyl sulfoxide.

The reaction temperature is generally from about 0° C. to 150° C., preferably from about 20° C. to 130° C. The reaction time is generally about 1 hour to 24 hours, preferably about 1 hour to 12 hours.

For "hydrolysis", compound (cIV) and an acid are reacted in an inert solvent.

The amount of use of acid is about 0.1–10 equivalents, preferably 1–5 equivalents, relative to compound (cIV).

Examples of the "acid" include mineral acid such as hydrochloric acid, hydrobromic acid etc., and the like.

As the "inert solvent", for example, water and organic acid (e.g., acetic acid etc.) and the like can be mixed for use.

The reaction temperature is generally from about 0° C. to 150° C., preferably from about 20° C. to 130° C. The reaction time is generally about 1 hour to 48 hours, preferably about 1 hour to 24 hours.

For "catalytic reduction", compound (cIV) and a catalytic amount of a metal catalyst (e.g., Raney-nickel, platinum oxide, metal palladium, palladium-carbon etc., preferably , palladium-carbon) are reacted in an inert solvent under a hydrogen pressure of 1–100 atm at 0–100° C. for about 1–48 hours. Preferable reaction conditions are 1–10 atm hydrogen pressure, at about 20–100° C. for about 1–24 hours.

Where necessary, an acid (e.g., hydrochloric acid, phosphoric acid, perchloric acid, sulfuric acid) and the like may be added in a catalytic amount (equivalent or in excess).

Examples of the "inert solvent" include organic acids (e.g., acetic acid, propionic acid), alcohols (e.g., methanol, ethanol, isopropylalcohol, 2-butanol, tert-butanol, 2-methyl-2-butanol etc.), ethers (e.g., diethyl ether, diisopropy ether, tert-butylmethyl ether, diphenyl ether, tetrahydrofuran, dioxane, 1,2-dimethoxyethane etc.), aliphatic hydrocarbons (e.g., hexane, pentane, cyclohexane etc.), aromatic hydrocarbons (e.g., benzene, toluene, xylene, chlorobenzene etc.), water, a mixture of two or more thereof and the like.

The compound (cV) thus obtained can be isolated and purified from a reaction mixture by a known method, such as concentration, concentration under reduced pressure, solvent extraction, crystallization, recrystallization, phase transfer, chromatography and the like.

Reaction c3

The compound (cV) is subjected to sulfonylation or halogenation reaction and then reacted with compound (cVI) to give compound (cVII). Specifically, compound (cV) and a sulfonylating agent or halogenating agent are reacted in an inert solvent in the presence of a base, where desired.

When the compound (cVI) is on the market, a commercially available product thereof may be used as it is, or compound (cVI) may be produced according to a method known per se, a method analogous thereto, and the like.

The amount of use of sulfonylating agent is about 0.1–10 equivalents, preferably 1–3 equivalents, relative to compound (CV).

The amount of use of halogenating agent is about 0.1–10 equivalents, preferably 1–3 equivalents, relative to compound (cV).

The amount of use of base is about 0.1–10 equivalents, preferably 1–3 equivalents, relative to compound (cV).

Examples of the "sulfonylating agent", include $R^5$—$SO_2Cl$ such as methanesulfonyl chloride, p-toluenesulfonyl chloride etc., and the like.

Examples of the "halogenating agent" include thionyl chloride, oxalyl chloride and the like.

Examples of the "base" include carbonate of alkali metal or alkaline each metal (e.g., sodium carbonate, potassium carbonate etc.), hydroxide of alkali metal or alkaline each metal (e.g., sodium hydroxide, potassium hydroxide, lithium hydroxide, calcium hydroxide), organic base (e.g., diisopropylethylamine, triethylamine, pyridine etc.) and the like.

Examples of the "inert solvent" include aliphatic hydrocarbons (e.g., hexane, pentane, cyclohexane etc.), aromatic hydrocarbons (e.g., benzene, toluene, xylene, chlorobenzene etc.), ethers (e.g., diethyl ether, diisopropy ether, tert-butylmethyl ether, diphenyl ether, tetrahydrofuran, dioxane, 1,2-dimethoxyethane etc.), halogenated hydrocarbons (e.g., dichloromethane, chloroform, 1,2-dichloroethane, carbon tetrachloride etc.), esters (e.g., ethyl acetate etc.), ketones (e.g., acetone, methyl ethyl ketone etc.), nitrites (e.g., acetonitrile, propionitrile etc.), sulfoxides (e.g., dimethyl sulfoxide etc.), amides (e.g., N,N-dimethylformamide, N,N-dimethylacetamide, N-methylpyrrolidone, hexamethylphosphoric triamide etc.), alcohols (e.g., methanol, ethanol, isopropyl alcohol, 2-butanol, tert-butanol, 2-methyl-2-butanol etc.) and a mixture of two or more of these. Preferred are tetrahydrofuran, acetonitrile, acetone and the like.

The reaction temperature is generally from about −40° C. to 100° C., preferably from about −20° C. to 80° C. The reaction time is generally about 1 hour to 12 hours, preferably about 1 hour to 6 hours.

Then, the thus-obtained reaction mixture and compound (cVI) are reacted in an inert solvent in the presence of a base and(or) a phase transfer catalyst, where desired, to give compound (cVII).

When the compound (cVI) is on the mark t, a commercially available product thereof may be used as it is, or compound (cVI) may be produced according to a method known per se, a method analogous thereto, and the like.

The amount of use of compound (cVI) is about 0.1–10 equivalents, preferably about 1–3 equivalents, relative to compound (cV).

The amount of use of base is about 1–100 equivalents, preferably about 1–10 equivalents, relative to compound (cV).

The amount of use of the phase transfer catalyst is about 0.01–1 equivalent, preferably about 0.01–0.3 equivalent, relative to compound (cV).

Examples of the "base" include carbonate of alkali metal or alkaline earth metal (e.g., sodium carbonate, potassium carbonate etc.), hydroxide of alkali metal or alkaline earth metal (e.g., sodium hydroxide, potassium hydroxide, lithium hydroxide, calcium hydroxide) and the like.

Examples of the "phase transfer catalyst" include tetra(n-butyl)ammonium bromide, tetra(n-butyl)ammonium hydrogensulfate and the like.

Examples of the "inert solvent" include aliphatic hydrocarbons (e.g., hexane, pentane, cyclohexane etc.), aromatic hydrocarbons (e.g., benzene, toluene, xylene, chlorobenzene etc.), ethers (e.g., diethyl ether, diisopropy ether, tert-butylmethyl ether, diphenyl ether, tetrahydrofuran, dioxane, 1,2-dimethoxyethane etc.), halogenated hydrocarbons (e.g., dichloromethane, chloroform, 1,2-dichloroethane, carbon tetrachloride etc.), esters (e.g., ethyl acetate etc.), ketones (e.g., acetone, methyl ethyl ketone etc.), nitrites (e.g., acetonitrile, propionitrile etc.), sulfoxides (e.g., dimethyl sulfoxide etc.), amides (e.g., N,N-dimethylformamide, N,N-dimethylacetamide, N-methylpyrrolidone, hexamethylphosphoric triamide etc.), alcohols (e.g., methanol, ethanol, isopropyl alcohol, 2-butanol, tert-butanol, 2-methyl-2-butanol etc.), water, a mixture of two or more thereof and the like. Preferred are tetrahydrofuran, acetonitrile, acetone, water and the like.

The reaction temperature is generally from about 0° C. to 150° C., preferably from about 20° C. to 130° C. The reaction time is generally about 1 hour to 24 hours, preferably about 1 hour to 12 hours.

The compound (cVII) thus obtained can be isolated and purified from a reaction mixture by a known method, such as concentration, concentration under reduced pressure, solvent extraction, crystallization, recrystallization, phase transfer, chromatography and the like.

The compound (cVII) useful as a pharmaceutical agent and the like can be also produced according to the following Reactions c4–c5.

Reaction c4

A reaction mixture of compound (cI) and compound (cII) is reacted with compound (cIII), and then the obtained compound is subjected to hydrolysis to give compound (cV).

The conditions for "a reaction mixture of compound (cI) and compound (cII) is reacted with compound (cIII)" are the same as in Reaction c1.

The "hydrolysis" only needs to follow the reaction described in Reaction c2, and the amount of use of base is about 0.1–10 equivalents, preferably 1–5 equivalents, relative to compound (cI). The amount of use of acid is about 0.1–10 equivalents, preferably 1–5 equivalents, relative to compound (cI).

Reaction c5

The compound (cV) obtained in Reaction c4 is subjected to sulfonylation or halogenation and then reacted with compound (cVI) to give compound (cVII).

The reaction conditions are the same as in Reaction c3.

The compound (cVIIa) useful as a pharmaceutical agent and the like can be also produced according to the following Reaction c6 or Reaction c7.

Reaction c6

A reaction mixture of compound (cIa) and compound (cII) is subjected to hydrolysis and the obtained compound (cVa) is subjected to sulfonylation or halogenation and then reacted with compound (cVI) to give compound (cVIIa).

This reaction only needs to follow the above-mentioned Reactions c1–c3. As a usable "base", for example, carbonate of alkali metal or alkaline earth metal (e.g., sodium carbonate, potassium carbonate etc.) and the like are preferable.

Reaction c7

A reaction mixture of compound (cIa) and compound (cII) is reacted with compound (cVI) to give compound (cVIIa).

This reaction only needs to follow the above-mentioned Reactions c1–c3.

The compounds (aVa), (aVb), (bX), (bXI) and (cVII) [inclusive of compound (cVIIa)] are useful as pharmaceutical agents, agricultural chemicals and the like.

The compounds (aVa), (aVb), (bX), (bXI) and (cVII) have a tyrosine kinase inhibitory action and can be used for the prophylaxis or treatment of tyrosine kinase-dependent diseases in mammal. The tyrosine kinase-dependent diseases include diseases caused by enhanced cell proliferation due to abnormal tyrosine kinase enzyme activity. Furthermore, since compounds (aVa), (aVb), (bX), (bXI) and (cVII) specifically inhibit HER2 tyrosine kinase, they are useful as a therapeutic agent for inhibiting growth of cancer that expresses HER2, or as an agent for preventing metastasis of hormone dependent cancer to hormone non-dependent cancer. That is, compounds (aVa), (aVb) (bX), (bXI) and (cVII) can be used as safe agents for the prophylaxis or treatment of diseases caused by abnormal cell growth such as various cancers (particularly breast cancer, prostate cancer, pancreatic cancer, stomach cancer), atherosclerosis, angiogenesis (e.g., angiogenesis accompanying growth of solid tumor and sarcoma, angiogenesis associated with tumor metastasis, angiogenesis associated with diabetic retinopathy etc.), viral diseases (HIV infection etc.) and the like. The tyrosine kinase-dependent diseases further include abnormal tyrosine kinase enzyme activity-related cardiovascular diseases. Therefore, the compounds (aVa), (aVb), (bX), (bXI) and (cVII) can be also used as an agent for the prophylaxis or treatment of cardiovascular diseases such as restenosis.

The compounds (aVa), (aVb), (bX), (bXI) and (cVII) have a tyrosine kinase inhibitory action and can be used for the prophylaxis or treatment of tyrosine kinase-dependent diseases in mammal. The tyrosine kinase-dependent diseases include diseases caused by enhanced cell proliferation due to abnormal tyrosine kinase enzyme activity. Furthermore, since compounds (aVa), (aVb), (bX), (bXI) and (cVII) specifically inhibit HER2 tyrosine kinase, they are useful as a therapeutic agent for inhibiting growth of cancer that expresses HER2, or as an agent for preventing metastasis of hormone dependent cancer to hormone non-dependent cancer.

That is, compounds (aVa), (aVb), (bX), (bXI) and (cVII) can be used as safe agents for the prophylaxis or treatment of diseases caused by abnormal cell growth such as various cancers (particularly breast cancer, prostate cancer, pancreatic cancer, stomach cancer, lung cancer, colon cancer, rectal cancer, esophageal cancer, duodenal carcinoma, tongue cancer, pharyngeal cancer, brain tumor, neurinomatosis, non-small cell lung cancer, small cell lung carcinoma, liver cancer, kidney cancer, bile duct cancer, cancer of uterine body, cervical carcinoma, ovarian cancer, bladder cancer, skin cancer, angiomatosis, malignant lymphoma, malignant melanoma, thyroid cancer, bone tumor, angiofibroma, retinal sarcoma, penile cancer, childhood solid cancer, Kaposi's sarcoma, AIDS related Kaposi's sarcoma, cancer of maxillary sinus, fibrous histiocytoma, leiomyosarcoma, rhabdomyosarcoma, leukemia etc.), atherosclerosis, angiogenesis (e.g., angiogenesis accompanying growth of solid tumor and sarcoma, angiogenesis associated with tumor metastasis, angiogenesis associated with diabetic retinopathy etc.), viral diseases (HIV infection and the like.

The tyrosine kinase-dependent diseases further include abnormal tyrosine kinase enzyme activity-related cardiovascular diseases. Therefore, the compounds (aVa), (aVb), (bX), (bXI) and (cVII) can be also used as an agent for the prophylaxis or treatment of cardiovascular diseases such as restenosis.

The compounds (aVa), (aVb), (bX), (bXI) and (cVII) are useful as anticancer agents for the prophylaxis or treatment of cancer, particularly breast cancer, prostate cancer, pancreatic cancer, stomach cancer, lung cancer, colon cancer and large bowel cancer.

The compounds (aVa), (aVb), (bX), (bXI) and (cVII) show low toxicity and can be used as they are as pharmaceutical agents or as a pharmaceutical composition in admixture with a pharmacologically acceptable carrier known per se for mammal such as human, horse, cattle, dog, cat, rat, mouse, rabbit, pig, monkey and the like.

A pharmaceutical composition may contain, along with the compound (aVa), (aVb), (bX), (bXI) or (cVII), other active ingredient, such as hormone preparation, anticancer agents (e.g., chemotherapy agent, immunotherapy agent and pharmaceutical agent inhibiting the action of cell growth factor and receptor thereof etc.) and the like.

When the compound (aVa), (aVb), (bX), (bXI) or (cVII) is administered as a pharmaceutical agent to mammal such as human, the administration route is oral administration in the form of, for example, tablets, capsules (inclusive of soft capsule and microcapsule), powders, granules and the like, or parenteral administration in the form of injection, suppository, pellet and the like. By the "parenterally" is meant intravenous, intramuscular, subcutaneous, intraorgan, intranasal, intradermal, instillation, intracerebral, intrarectal, intravaginal and intraperitoneal administrations, administration into tumor, administration to the vicinity of tumor and direct administration to the focus. While the dose of the compound (aVa), (aVb), (bX), (bXI) or (cVII) varies depending on the administration route, symptoms and the like, when, for example, it is orally administered as an anticancer agent to a patient weighing 40 to 80 kg having, for example, breast cancer or prostate cancer, it is 0.5–100 mg/kg body weight, preferably 1–50 mg/kg body weight, more preferably 1–25 mg/kg body weight, which is administered once a day or in 2 or 3 doses a day.

The compound (aVa), (aVb), (bX), (bXI) or (cVII) is admixed with a pharmacologically acceptable carrier and administered orally or parenterally as a solid preparation such as tablet, capsule, granule, powder and the like or a liquid preparation such as syrup, injection and the like.

As the pharmacologically acceptable carrier usable for the production of the pharmaceutical composition, there are mentioned various conventional organic or inorganic carriers as a material for the preparation. Examples thereof include excipients, lubricants, binders and disintegrators for solid preparations, and solvents, solubilizing aids, suspending agents, isotonic agents, buffers and soothing agents for liquid preparations. Where necessary, conventional additives such as antiseptics, antioxidants, coloring agents, sweeteners and the like can be used.

As preferable examples of the excipient, there are mentioned, for example, lactose, sucrose, D-mannitol, starch, crystalline cellulose, light anhydrous silicic acid and the like.

As preferable examples of the lubricant, there are mentioned, for example, magnesium stearate, calcium stearate, talc, colloidal silica and the like.

As preferable examples of the binder, there are mentioned, for example, crystalline cellulose, sucrose, D-mannitol, dextrin, hydroxypropylcellulose, hydroxypropylmethylcellulose, polyvinylpyrrolidone and the like.

As preferable examples of the disintegrator, there are mentioned, for example, starch, carboxymethylcellulose, carboxymethylcellulose calcium, crosscarmellose, sodium carboxymethyl starch and the like.

As preferable examples of the solvent, there are mentioned, for example, injectable water, alcohol, propylene glycol, Macrogol, sesame oil, corn oil and the like.

As preferable examples of the solubilizing aid, there are mentioned, for example, polyethylene glycol, propylene glycol, D-mannitol, benzyl benzoate, ethanol, trisaminomethane, cholesterol, triethanolamine, sodium carbonate, sodium citrate and the like.

As preferable examples of the suspending agent, there are mentioned, for example, surfactants such as stearyl triethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like.

As preferable examples of the isotonicity agent, there are mentioned, for example, sodium chloride, glycerine, D-mannitol and the like.

As preferable examples of the buffer, there are mentioned, for example, buffers such as phosphate, acetate, carbonate, citrate and the like.

As preferable examples of the soothing agent, there are mentioned, for example, benzyl alcohol and the like.

As preferable examples of the antiseptic, there are mentioned, for example, p-oxybenzoates, chlorobutanol, benzyl alcohol, phenethyl alcohol, dehydroacetic acid, sorbic acid and the like.

As preferable examples of the antioxidant, there are mentioned, for example, sulfite, ascorbic acid and the like.

While the pharmaceutical composition varies depending on the dosage form, administration method, carrier and the like, it can be produced according to a conventional method by adding compound (aVa), (aVb), (bX), (bXI) or (cVII) generally in an amount of 0.1–95%(w/w) of the entire amount of the preparation.

In addition, by (1) administering an effective amount of compound (aVa), (aVb), (bX), (bXI) or (cVII), (2) (i) administering an effective amount of a different anticancer agent, (ii) administering an effective amount of a hormone preparation, or (iii) by combining 1 to 3 kinds from a group consisting of therapies without medicine, cancer can be more effectively prevented or treated. As the therapy without medicine, there are mentioned, for example, operation, radiation therapy, gene therapy, thermotherapy, cryotherapy, laser cauterization therapy and the like, and two or more of these can be combined.

For example, the compound of the present invention can be used in combination with other hormone preparations, anticancer agents (e.g., chemotherapy agent, immunotherapy agent and pharmaceutical agent inhibiting the action of cell growth factor and receptor thereof) and the like (hereinafter to be briefly referred to as combination drug).

While the compounds (aVa), (aVb), (bX), (bXI) or (cVII) shows a superior anticancer effect even when used as a single agent, when it is used in combination with one or more of the above-mentioned combination drugs (combined use of plural agents), the effect can be reinforced furthermore.

Examples of the "hormone preparation" include fosfestrol, diethylstilbestrol, chlorotrianiseline, medroxyprogesterone acetate, megesterol acetate, chlormadinone acetate, cyproterone acetate, danazol, allylestrenol, gestrinone, mepartricine, raloxifene, ormeloxifene, levormeloxifene, antiestrogen (e.g., tamoxifen citrate, toremifene citrate etc.), contraceptive pill, mepitiostane, testolactone, aminoglutethimide, LH—RH agonist (e.g., goserelin acetate, buserelin, leuprorelin etc.), droloxifene, epitiostanol, ethinylestradiol sulfonate, aromatase inhibitor (e.g., fadrozole hydrochloride, anastrozole, letrozole, exemestane, vorozole, formestane etc.), antiandrogen (e.g., flutamide, bicalutamide, nilutamide etc.), 5α-reductase inhibitor (e.g., finasteride, episteride etc.), adrenocortical hormone preparation (e.g., dexamethasone, prednisolone, betamethasone, triamcinolone etc.), androgen synthesis inhibitor (e.g., abiraterone etc. and lyase inhibitor), retinoid and an agent to delay metabolism of retinoid (e.g., liarozole etc.) and the like. Of these, LH—RH agonist (e.g., goserelin acetate, buserelin, leuprorelin etc.) is preferable.

Examples of the "chemotherapy agent" include alkylating agent, antimetabolite, carcinostatic antibiotics, plant alkaloid and the like.

Examples of the "alkylating agent" include nitrogen mustard, nitrogen mustard-n-oxide hydrochloride, chrorambucil, cyclophosphamide, ifosfamide, thiotepa, carboquone, improsulfan tosilate, busulfan, nimustine hydrochloride, mitobronitol, melphalan, dacarbazine, ranimustine, sodium estramustine phosphate, triethylene melamine, carmustine, lomustine, streptozocin, pipobroman, etoglucide, altretamin, ambamustine, dibrospidium hydrochloride, fotemustine, prednimustine, pumitepa, ribomustin, temozolomide, treosulfan, trophosphamide, zinostatin stimalamer, carboquone, adozelesin, cystemstin, bizelesin, platinym complex (carboplatin, cisplatin, miboplatin, nedaplatin, oxaliplatin etc.) and the like.

Examples of the "antimetabolite" include mercaptopurine, 6-mercaptopurine riboside, thioinosine, methotrexate, enocitabine, cytarabine, cytarabine ocphosphate, ancitabine hydrochloride, 5-FU pharmaceutical agents (e.g., fluorouracil, tegafur, UFT, doxifluridine, carmofur, galocitabine, emitefur etc.), aminopterin, calcium leucovorin, tabloid, butocin, calcium folinate, calcium levofolinate, cladribine, emitefur, fludarabine, gemcitabine, hydroxycarbamide, pentostatin, piritrexim, idoxuridine, mitoguazone, tiazofurin, ambamstine and the like.

Examples of the "carcinostatic antibiotics" include anthracyclin carcinostatic agents (doxorubicin hydrochloride, daunorubicin hydrochloride, aclarubicin hydrochloride, pirarubicin hydrochloride, epirubicin hydrochloride etc.), actinomycin D, actinomycin C., mitomycin C., chromomycin A3, bleomycin hydrochloride, bleomycin sulfate, peplomycin sulfate, neocarzinostatin, mithramycin, sarcomycin, carzinophilin, mitotane, zorubicin hydrochloride, mitoxantrone hydrochloride, idarubicin hydrochloride and the like.

Examples of the "plant alkaloid" include vinca alkaloid carcinostatic agents (vinblastine sulfate, vincristine sulfate, vindesine sulfate etc.), taxan anticancer agents (paclitaxel, docetaxel etc.), etoposide, etoposide phosphate, teniposide, vinorelbine and the like.

Examples of the "immunotherapeutic agent" (BRM) include picibanil, krestin, sizofiran, lentinan, ubenimex, interferon, interleukin, macrophage colony stimulating factor, granulocyte-colony stimulating factor, erythropoietin, lymphotoxin, BCG vaccine, Corynebacterium parvum, levamisole, polysaccharide K, procodazol and the like.

As the "cell growth factor" in the "pharmaceutical agent inhibiting action of the cell growth factor and its receptor", any substance can be used as long as it enhances proliferation of cells. In general, a factor which is a peptide having a molecular weight of not more than 20,000, and which can show effect upon binding with receptor at a low concentration is exemplified. Specific examples include (1) EGF (epidermal growth factor) or a substance having substantially the same activity therewith [e.g., EGF, heregulin (HER2 ligand) etc.], (2) insulin or a substance having substantially the same activity therewith [e.g., insulin, IGF (insulin-like growth factor)-1, IGF-2 etc.], (3) FGF (fibroblast growth factor) or a substance having substantially the same activity therewith [e.g., acidic FGF, basic FGF, KGF (keratinocyte growth factor), FGF-10 etc.], (4) other cell growth factors [e.g., CSF (colony stimulating factor), EPO (erythropoietin), IL-2(interleukin-2), NGF (nerve growth factor), PDGF (platelet-derived growth factor), TGFβ (transforming growth factor β), HGF (hepatocyte growth factor), VEGF (vascular endothelial growth factor) etc.] and the like.

The "receptor of the cell growth factor" may be any receptor as long as it has a binding ability with the above-mentioned cell growth factor. Specific examples include EGF receptor, heregulin receptor (HER2), insulin receptor, IGF receptor, FGF receptor-1, FGF receptor-2, HGF receptor (c-met), VEGF receptor, SCF receptor (c-kit), and the like.

Examples of the "pharmaceutical agent inhibiting action of the cell growth factor" include herceptin (HER2 antibody), GLEEVEC (c-met, c-kit, abl inhibitor), Iressa (EGF receptor inhibitor) and the like.

In addition to the aforementioned pharmaceutical agents, L-asparaginase, aceglatone, procarbazine hydrochloride, cobalt protoporphyrin complex, mercurial hematoporphyrin sodium, topoisomerase I inhibitor (e.g., irinotecan, topotecan etc.), topoisomerase II inhibitor (e.g., sobuzoxane etc.), differentiation inducing agent (e.g., retinoid, vitamine D etc.), angiogenesis inhibitor, α-blocker (e.g., tamsulosin hydrochloride etc.) and the like can be also used.

Of the above-mentioned combination drugs, LH—RH agonist (e.g., goserelin acetate, buserelin acetate, leuprorelin acetate etc.), herceptin (HER2 antibody) and the like are preferable.

For the combined use of compound (aVa), (aVb), (bX), (bXI) or (cVII) and combination drug, the time of administration of compound (aVa), (aVb), (bX), (bXI) or (cVII) and combination drug is not limited. The compound (aVa), (aVb), (bX), (bXI) or (cVII) and combination drug may be simultaneously administered to an administration object or administered in a staggered manner. The dose of the combination drug only needs to follow the dose clinically employed, and can be determined as appropriate depending on the administration object, administration route, disease, combination and the like.

The mode of administration of the compound (aVa), (aVb), (bX), (bXI) or (cVII) and combination drug(s) is not particularly limited, and may be any as long as the compound (aVa), (aVb), (bX), (bXI) or (cVII) and combination drug(s) are combined on administration. Such administration mode is exemplified by (1) administration of a single preparation obtained by simultaneously formulating the compound (aVa), (aVb), (bX), (bXI) or (cVII) and combination drug(s) into a preparation, (2) simultaneous administration by the same administration route of two kinds of preparations obtained by separately formulating the compound (aVa), (aVb), (bX), (bXI) or (cVII) and combination drug(s) into preparations, (3) staggered administration by the same administration route of two kinds of preparations obtained by separately formulating the compound (aVa), (aVb), (bX), (bXI) or (cVII) and combination drug(s) into preparations, (4) simultaneous administration by different administration routes of two kinds of preparations obtained by separately formulating the compound (aVa), (aVb), (bX), (bXI) or (cVII) and combination drug(s) into preparations, (5) staggered administration by different administration routes of two kinds of preparations obtained by separately formulating the compound (aVa), (aVb), (bX), (bXI) or (cVII) and combination drug(s) into preparations (e.g., administration in the order of compound (aVa), (aVb), (bX), (bXI) or (cVII)→combination drug, and administration in the reversed order) and the like. These modes of administrations are collectively referred to in the following as a combination agent of the present invention.

The combination agent of the present invention has low toxicity and can be administered safely by admixing the compound (aVa), (aVb), (bX), (bXI) or (cVII) and/or combination drug(s) with, for example, a pharmacologically acceptable carrier according to a method known per se to give a pharmaceutical composition, such as tablets (inclusive of sugar-coated tablets and film-coated tablets), powders, granules, capsules, (inclusive of soft capsules), liquids, injections, suppositories, sustained release agents and the like, for oral or parenteral (e.g., topical, rectal or intravenous administration) administration. An injection can be administered intravenously, intramuscularly, subcutaneously, into the organ, intranasally, intradermally, by instillation, intracerebrally, intrarectally, intravaginally, intraperitoneally, into tumor, to the vicinity of tumor or directly to the focus.

As the pharmacologically acceptable carrier usable for the production of the combination agent of the present invention, there are mentioned those usable for the aforementioned pharmaceutical composition.

The content ratio of the compound (aVa), (aVb), (bX), (bXI) or (cVII) and combination drug in the combination agent of the present invention can be appropriately determined depending on the administration object, administration route, disease and the like.

For example, the content of the compound (aVa), (aVb), (bX), (bXI) or (cVII) in the combination agent of the present invention is generally about 0.01–100 wt %, preferably about 0.1–50 wt %, more preferably about 0.5–20 wt %, based on the preparation in total, though they may change depending on the preparation form.

The content of the combination drug in the combination agent of the present invention is generally about 0.01–100 wt %, preferably about 0.1–50 wt %, more preferably about 0.5–20 wt %, based on the preparation in total, though may change depending on the preparation form.

The content of the additive in the combination agent of the present invention varies depending on the form of the preparation. It is generally about 1–99.99 wt %, preferably about 10–90 wt %, based on the preparation in total.

The same contents are employed when the compound (aVa), (aVb), (bX), (bXI) or (cVII) and combination drug(s) are formulated separately into preparations.

These preparations can be produced by a method known per se, which is generally employed for the preparation steps.

For example, the compound (aVa), (aVb), (bX), (bXI) or (cVII), or a combination drug can be prepared into an aqueous injection together with a dispersant (e.g., Tween 80 (ATLAS POWDER USA), HCO60 (NIKKO CHEMICALS), polyethylene glycol, carboxymethylcellulose, sodium arginate, hydroxypropylmethylcellulose, dextrin etc.), a stabilizer (e.g., ascorbic acid, sodium pyrosulfite etc.), a surfactant (e.g., polysorbate 80, Macrogol etc.), a solubilizer (e.g., glycerine, ethanol etc.), a buffering agent (e.g., phosphoric acid, alkali metal salt thereof, citric acid, alkali metal salt thereof etc.), an isotonicity agent (e.g., sodium chloride, potassium chloride, mannitol, sorbitol, glucose etc.), a pH adjusting agent (hydrochloric acid, sodium hydroxide etc.), a preservative (ethyl p-hydroxybenzoate, benzoic acid, methylparaben, propylparaben, benzyl alcohol etc.), a solubilizer (e.g., conc. glycerine, meglumine etc.), a solubilizing aid (e.g., propylene glycol, sucrose etc.), a soothing agent (e.g., glucose, benzyl alcohol etc.) and the like, or into an oil-based injection by dissolving, suspending or emulsifying in a vegetable oil (e.g., olive oil, sesame oil, cottonseed oil, corn oil etc.) or a solubilizing aid such as propylene glycol etc., and used as an injection.

An oral formulation can be produced by a method known per se by admixing the compound (aVa), (aVb), (bX), (bXI) or (cVII), or a combination drug with an excipient (e.g., lactose, sucrose, starch and the like), a disintegrant (e.g., starch, calcium carbonate and the like), a binder (e.g., starch, gum arabic, carboxymethyl cellulose, polyvinyl pyrrolidone, hydroxypropyl cellulose and the like) or a lubricant (e.g., talc, magnesium stearate, polyethylene glycol 6000 and the like) and compressing the mixture, optionally followed by a coating process known per se for the purpose of masking a taste, forming an enteric coat, or achieving a sustained release. Such coating may, for example, be hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethyl cellulose acetate succinate, Eudragid (ROHME, Germany, a copolymer of methacrylic acid and acrylic acid), a dye (e.g., colcothar, titanium oxide etc.) and the like. The preparation for oral administration may be either a rapid release preparation or a sustained release preparation.

A suppository can be produced by making the compound (aVa), (aVb), (bX), (bXI) or (cVII), or a combination drug into an oily or aqueous solid, semisolid or liquid composition. Examples of the oily base to be used for such a composition include glyceride of higher fatty acid (e.g., cacao butter, Witepsol (Dynamit Nobel, Germany etc.), medium fatty acid (e.g., migliol (Dynamit Nobel, Grmany etc.), vegetable oil (e.g., sesame oil, soybean oil, cottonseed oil etc.) and the like. Examples of the aqueous gel base include natural gums, cellulose derivative, vinyl polymer, acrylate polymer and the like Examples of the above-mentioned sustained release preparation include sustained release microcapsule and the like.

A sustained release microcapsule can be prepared by a method known per se. For example, a sustained release preparation shown in the following [2] is preferably formed and administered.

The compound (aVa), (aVb), (bX), (bXI) or (cVII) is preferably formed into a preparation for oral administration such as a solid preparation (e.g., powder, granule, tablet, capsule) and the like, or a preparation for rectal administration such as a suppository and the like. Particularly, a preparation for oral administration is preferable.

The combination drug can be prepared into the above-mentioned dosage form according to the kind of the drug.

In the following, [1] an injection of the compound (aVa), (aVb), (bX), (bXI) or (cVII), or a combination drug and preparation thereof, [2] a sustained release preparation or a rapid release preparation of the compound (aVa), (aVb), (bX), (bXI) or (cVII), or a combination drug and preparation thereof, and [3] a sublingual tablet, buccal or oral cavity rapid disintegrator of the compound (aVa), (aVb), (bX), (bXI) or (cVII), or a combination drug and preparation thereof are concretely explained.

[1] Injection and Preparation Thereof

An injection containing the compound (aVa), (aVb), (bX), (bXI) or (cVII), or a combination drug dissolved in water is preferable. The injection may contain benzoate and/or salicylate.

The injection is obtained by dissolving both the compound (aVa), (aVb), (bX), (bXI) or (cVII), or a combination drug and, where desired, benzoate and/or salicylate in water.

The salt of the above-mentioned benzoic acid and salicylic acid includes, for example, alkali metal salts such as sodium, potassium and the like, alkaline earth metal salts such as calcium, magnesium and the like, ammonium salt, meglumine salt, and organic acid salt such as trometamol and the like, and the like.

The concentration of the compound (aVa), (aVb), (bX), (bXI) or (cVII), or a combination drug in the injection is about 0.5–50 w/v %, preferably about 3–20 w/v %. The concentration of the benzoate and/or salicylate is preferably 0.5–50 w/v %, more preferably 3–20 w/v %.

This agent may contain additives generally used for injections, such as a stabilizer (e.g., ascorbic acid, sodium pyrosulfite etc.), a surfactant (e.g., polysorbate 80, Macrogol etc.), a solubilizer (e.g., glycerine, ethanol etc.), a buffering agent (e.g., phosphoric acid, alkali metal salt thereof, citric acid, alkali metal salt thereof etc.), an isotonicity agent (e.g., sodium chloride, potassium chloride etc.), a dispersing agent (e.g., hydroxypropylmethylcellulose, dextrin), a pH adjusting agent (hydrochloric acid, sodium hydroxide etc.), a preservative (ethyl p-hydroxybenzoate, benzoic acid etc.), a solubilizer (e.g., conc. glycerine, meglumine etc.), a solubilizing aid (e.g., propylene glycol, sucrose etc.), a soothing agent (e.g., glucose, benzyl alcohol etc.) and the like as appropriate. These additives are added in a proportion generally employed for injections.

The injection is preferably adjusted to pH 2–12, preferably 2.5–8.0, by the use of a pH adjusting agent.

The injection can be obtained by dissolving both the compound (aVa), (aVb), (bX), (bXI) or (cVII), or a combination drug and, where desired, benzoate and/or salicylate, and where necessary, the above-mentioned additives in water. These may be dissolved in any order in a suitable manner as in conventional production of injections.

The injectable aqueous solution is preferably heated and, in the same manner as with conventional injections, subjected to, for example, sterilization by filtration, high pressure sterilization by heating and the like to provide an injection.

The injectable aqueous solution is preferably subjected to high pressure sterilization by heating at, for example, 100° C.–121° C. for 5 min–30 min.

It may be prepared into an antibacterial solution, so that it can be used as a preparation for plural subdivided administrations.

[2] Sustained Release Preparation or Rapid Release Preparation and Preparation Thereof A sustained release preparation wherein a core containing the compound (aVa), (aVb), (bX), (bXI) or (cVII), or a combination drug is covered on demand with a film forming agent, such as a water-insoluble material, a swellable polymer and the like, is preferable. For example, a sustained release preparation for oral administration once a day is preferable.

The water-insoluble material to be used for the film forming agent is, for example, cellulose ethers such as ethylcellulose, butylcellulose and the like; cellulose esters such as cellulose acetate, cellulose propionate and the like; polyvinyl esters such as poly(vinyl acetate), poly(vinyl butyrate) and the like; acrylic polymers such as acrylic acid/methacrylic acid copolymer, methyl methacrylate copolymer, ethoxyethyl methacrylate/cinnamoethyl methacrylate/aminoalkyl methacrylate copolymer, polyacrylic acid, polymethacrylic acid, methacrylic acid alkylamide copolymer, poly(methyl methacrylate), polymethacrylate, polymethacryl amide, aminoalkyl methacrylate copolymer, poly(methacrylic anhydride) and glycidyl methacrylate copolymer, particularly Eudragits (Rohm Pharma) such as Eudragit RS-100, RL-100, RS-30D, RL-30D, RL-PO, RS-PO (ethyl acrylate-methyl methacrylate-trimethyl chloride methacrylate-ammonium ethyl copolymer), Eudragit NE-30D (methyl methacrylate-ethyl acrylate copolymer) and the like, and the like; hydrogenated oils such as hydrogenated castor oil (e.g., Lubri wax (Freund Inc.) and the like) and the like; waxes such as carnauba wax, fatty acid glycerine ester, paraffin and the like; polyglycerine fatty acid ester and the like.

As the swellable polymer, a polymer having an acidic dissociable group, which shows pH-dependent swelling, is preferable, and a polymer having an acidic dissociable group, which shows less swelling in an acidic range, such as in the stomach, but otherwise in a neutral range, such as in the small intestine and large intestine, is preferable.

Examples of the polymer having an acidic dissociable group, which shows pH-dependent swelling, include crosslinking type polyacrylic acid polymers such as Carbomer 934P, 940, 941, 974P, 980, 1342 and the like, polycarbophil, calcium polycarbophil (all mentioned above are the product of BF Goodrich), HI-BIS-WAKO 103,104, 105, 304 (all being products of Waco Pure Chemicals Industries, Ltd.) and the like.

The film forming agent to be used for the sustained release preparation may further contain a hydrophilic material.

Examples of the hydrophilic material include polysaccharides optionally having a sulfuric acid group such as pullulan, dextrin, alkali metal salt of alginic acid and the like; polysaccharides having a hydroxy alkyl group or a carboxy alkyl group such as hydroxypropylcellulose, hydroxypropylmethylcellulose, sodium carboxymethylcellulose and the like; methylcellulose, polyvinylpyrrolidone, polyvinyl alcohol, polyethylene glycol and the like.

The content of the water-insoluble material of the film forming agent for a sustained release preparation is about 30–about 90% (w/w), preferably about 35–about 80% (w/w), more preferably about 40–75% (w/w), and the content of the swellable polymer is about 3–about 30% (w/w), preferably about 3–about 15% (w/w). The film forming agent may further contain a hydrophilic material, in which case the content of the hydrophilic material for film forming agent is not more than about 50% (w/w), preferably about 5–about 40% (w/w), more preferably about 5–about 35% (w/w). As used herein, the above-mentioned % (w/w) is a percentage relative to the film forming agent composition wherein the solvent (e.g., water, lower alcohol such as methanol, ethanol and the like) has been removed from the film forming liquid agent.

A sustained release preparation is produced by preparing a core containing a drug as exemplarily mentioned below, and coating the resulting core with a film forming liquid agent prepared by dissolving by heating or dissolving or dispersing in a solvent a water-insoluble material, a swellable polymer and the like.

I. Preparation of Core Containing a Drug

The form of the core containing a drug (hereinafter sometimes simply referred to as a core) to be coated with a film forming agent is not particularly limited, but it is preferably formed into particles such as granules, fine granules and the like.

When the core is made of granules or fine granules, the average particle size thereof is preferably about 150–2,000 $\mu$m, more preferably about 500–about 1,400 $\mu$m.

The core can be prepared by a typical production method. For example, a drug is mixed with suitable excipients, binders, disintegrators, lubricants, stabilizers and the like, and subjected to wet extrusion granulation, fluidized bed granulation and the like.

The drug content of the core is about 0.5–about 95% (w/w), preferably about 5.0–about 80% (w/w), more preferably about 30–about 70% (w/w).

Examples of the excipient to be contained in the core include saccharides such as sucrose, lactose, mannitol, glucose and the like, starch, crystalline cellulose, calcium phosphate, cornstarch and the like. Of these, crystalline cellulose and corn starch are preferable.

Examples of the binder include polyvinyl alcohol, hydroxypropylcellulose, polyethylene glycol, polyvinylpyrrolidone, Pluronic F68, gum arabic, gelatin, starch and the like. Examples of the disintegrator include carboxymethylcellulose calcium (ECG505), crosscarmellose sodium (Ac-Di-Sol), crosslinked polyvinylpyrrolidone (Crospovidone), low substituted hydroxypropylcellulose (L-HPC) and the like. Of these, hydroxypropylcellulose, polyvinylpyrrolidone and low substituted hydroxypropylcellulose are preferable. Examples of the lubricant and coagulation preventive include talc, magnesium stearate and inorganic salts thereof, and examples of the lubricant include polyethylene glycol and the like. Examples of the stabilizer include acids such as tartaric acid, citric acid, succinic acid, fumaric acid, maleic acid and the like.

The core can be also prepared by, besides the abovementioned production methods, for example, rolling granulation wherein a drug or a mixture of a drug and an excipient, a lubricant and the like is added by small portions while spraying a binder dissolved in a suitable solvent such as water, lower alcohol (e.g., methanol, ethanol and the like) and the like on an inert carrier particles to be the center of the core, a pan coating method, a fluidized bed coating method or a melt granulating method. Examples of the inert carrier particle include those prepared from sucrose, lactose, starch, crystalline cellulose and waxes, which preferably have an average particle size of about 100 $\mu$m–about 1,500 $\mu$m.

To separate the drug contained in the core from the film forming agent, the surface of the core may be coated with a protective agent. Examples of the protective agent include the aforementioned hydrophilic material, water-insoluble material and the like. As the protective agent, preferably polyethylene glycol, polysaccharides having a hydroxy alkyl group or a carboxy alkyl group, more preferably hydroxypropylmethylcellulose and hydroxypropylcellulose are used. The protective agent may contain, as a stabilizer, an acid such as tartaric acid, citric acid, succinic acid, fumaric acid, maleic acid and the like, and a lubricant such as talc and the like. When the protective agent is used, the amount to be coated is about 1–about 15% (w/w), preferably about 1–about 10% (w/w), more preferably about 2–about 8% (w/w), relative to the core.

The protective agent can be coated by a typical coating method. Specifically, the protective agent is, for example, spray-coated to the core by a fluidized bed coating method, a pan coating method, and the like.

II. Coating of Core with a Film Forming Agent

The core obtained in the aforementioned I is coated with a film forming liquid agent prepared by dissolving by heating or dissolving or dispersing in a solvent the aforementioned water-insoluble material, a pH-dependent swellable polymer, and a hydrophilic material to provide a sustained release preparation.

For coating a core with a film forming liquid agent, for example, a spray coating method and the like can be employed.

The composition ratio of the water-insoluble material, swellable polymer or hydrophilic material in the film forming liquid agent is suitably determined such that each component of the coating film meets the aforementioned content.

The coating amount of the film forming agent is about 1–about 90% (w/w), preferably about 5–about 50% (w/w), more preferably about 5–35% (w/w), relative to the core (exclusive of the coating amount of protective agent).

As the solvent for the film forming liquid agent, water or organic solvents can be used alone or in a mixture of the both. The mixing ratio (water/organic solvent: weight ratio) of water and the organic solvent in the mixture can vary within the range of 1–100%, which is preferably 1–about 30%. The organic solvent is not subject to any particular limitation as long as it dissolves the water-insoluble material. For example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Of these, lower alcohol is preferable, and ethyl alcohol and isopropyl alcohol are particularly preferable. Water and a mixture of water and an organic solvent are preferably used as a solvent of the film forming agent. Where necessary, the film forming liquid agent may contain an acid such as tartaric acid, citric acid, succinic acid, fumaric acid, maleic acid and the like for the stabilization of the film forming liquid agent.

When spray coating is employed, the method follows a conventional coating method, which specifically includes spray coating the core with a film forming liquid agent by, for example, a fluidized bed coating method, a pan coating method and the like. Where necessary, talc, titanium oxide, magnesium stearate, calcium stearate, light anhydrous silicic acid and the like may be added as a lubricants and glycerine fatty acid ester, hydrogenated castor oil, triethyl citrate, cetyl alcohol, stearyl alcohol and the like may be added as a plasticizer.

After coating with a film forming agent, an antistatic agent such as talc and the like may be added as necessary.

A rapid release preparation may be a liquid (solution, suspension, emulsion and the like) or a solid (particle, pill, tablet and the like). An agent for oral administration, and an agent for parenteral administration, such as injection and the like, are used, with preference given to an agent for oral administration.

A rapid release preparation may generally contain, in addition to the drug, which is an active ingredient, carriers, additives and excipients (hereinafter sometimes simply referred to as excipient) conventionally used in the field of preparation. The excipient for a preparation is not subject to any particular limitation as long as it is conventionally employed as an excipient for a preparation. For example, the excipient for the oral solid preparation includes lactose, starch, corn starch, crystalline cellulose (Asahi Kasei Corporation, Avicel PH101 and the like), powder sugar, granulated sugar, mannitol, light anhydrous silicic acid, magnesium carbonate, calcium carbonate, L-cysteine and the like, preferably corn starch and mannitol and the like. These excipients may be used alone or in combination. The content of the excipient is, for example, about 4.5–about 99.4 w/w%, preferably about 20–about 98.5 w/w%, more preferably about 30–about 97 w/w%, of the total amount of the rapid release preparation.

The drug content of the rapid release preparation is appropriately determined from the range of about 0.5–about 95%, preferably about 1–about 60%, of the total amount of the rapid release preparation.

When the rapid release preparation is an oral solid preparation, it generally contains a disintegrator in addition to the above-mentioned components. Examples of the disintegrator include calcium carboxymethylcellulose (Gotoku Pharmaceutical Co., Ltd., ECG-505), crosscarmellose sodium (e.g., Asahi Kasei Corporation, acjizol), Crospovidone (e.g., colidone CL, BASF), low substituted hydroxypropylcellulose (Shin-Etsu Chemical Co., Ltd.), carboxymethyl starch (Matsutani Chemical Industry Co., Ltd., sodium carboxymethyl starch (Kimura Sangyo, exprotab), partially α starch (PCS, Asahi Kasei Corporation) and the like. For example, one capable of disintegrating granules by water absorption, swelling, forming a channel between the active ingredient constituting the core and an excipient upon contact with water and the like can be used. These disintegrators can be used alone or in combination. The amount of the disintegrator is appropriately determined depending on the kind of the combination drug to be used and amount thereof, design of the release preparation and the like. It is generally about 0.05–about 30 w/w %, preferably about 0.5–about 15 w/w %, relative to the total amount of the rapid release preparation.

When the rapid release preparation is an oral preparation, the oral solid preparation may further contain, in addition to the above-mentioned composition, typical additives used for solid preparation on demand. Examples of the additive include a binder (e.g., sucrose, gelatin, gum arabic powder, methylcellulose, hydroxypropylcellulose, hydroxypropylmethylcellulose, carboxymethylcellulose, polyvinylpyrrolidone, Pullulan, dextrin etc.), a lubricant (e.g., polyethylene glycol, magnesium stearate, talc, light anhydrous silicic acid (e.g., Aerosil (Nippon Aerosil)), a surfactant (e.g., anionic surfactant such as sodium alkylsulfate etc., non-ionic surfactant such as polyoxyethylene fatty acid ester and polyoxyethylenesorbitan fatty acid ester, polyoxyethylene castor oil derivative etc., and the like), a coloring agent (e.g., tar color, caramel, iron oxide red, titanium oxide, riboflavins), where necessary, a corrigent (e.g., a sweetener, flavor etc.), an absorbent, an antiseptic, a moistening agent, an antistatic agent and the like. As the stabilizer, an organic acid such as tartaric acid, citric acid, succinic acid, fumaric acid and the like may be added.

Examples of the above-mentioned binder preferably include hydroxypropylcellulose, polyethylene glycol, polyvinylpyrrolidone and the like.

The rapid release preparation can be prepared based on the conventional preparation method, by mixing each of the aforementioned components, and where necessary, further kneading and forming. The above-mentioned mixing can be performed by a conventional method, such as mixing, kneading and the like. Specifically, for example, when a rapid release preparation is formed into particles, a vertical granulator, a universal kneader (HATA Tekkohjo), a fluidized bed granulator FD-5S (Powrex Corporation) and the like are used for mixing, which is followed by granulating by wet extrusion granulation, fluidized bed granulation and the like, to give the preparation, as in the preparation of the core of the aforementioned sustained release preparation.

The rapid release preparation and the sustained release preparation thus obtained may be used as they are. Alternatively, after suitable separate preparation along with an excipient for a preparation and the like according to a conventional method, they may be administered simultaneously or at optional administration intervals. Alternatively, they may be each prepared into a single preparation for oral administration (e.g., granule, fine granule, tablet, capsule and the like) as they are or together with excipient for preparation and the like as appropriate. The both preparations are converted to granules or fine granules and filled in a single capsule and the like to give a preparation for oral administration.

[3] A Sublingual Tablet, Buccal or Oral Cavity Rapid Disintegrator and Preparation Thereof The sublingual tablet, buccal preparation and oral cavity rapid disintegrator may be a solid preparation such as tablet and the like or an oral cavity mucous membrane adhesion tablet (film).

As the sublingual tablet, buccal or oral cavity rapid disintegrator, a preparation containing the compound (aVa), (aVb), (bX), (bXI) or (cVII), or a combination drug and an excipient is preferable. It may contain auxiliaries such as a lubricant, an isotonic agent, a hydrophilic carrier, a water dispersible polymer, a stabilizer and the like. For easy absorption and enhanced bioavailability, β-cyclodextrin or β-cyclodextrin derivative (e.g., hydroxypropyl-β-cyclodextrin and the like) and the like may be contained.

Examples of the above-mentioned excipient include lactose, sucrose, D-mannitol, starch, crystalline cellulose, light anhydrous silicic acid and the like. Examples of the lubricant include magnesium stearate, calcium stearate, talc, colloidal silica and the like, particularly magnesium stearate and colloidal silica are preferable. Examples of the isotonicity agent include sodium chloride, glucose, fructose, mannitol, sorbitol, lactose, saccharose, glycerine, urea and the like, particularly mannitol is preferable. Examples of the hydrophilic carrier include swellable hydrophilic carriers such as crystalline cellulose, ethylcellulose, crosslinked polyvinylpyrrolidone, light anhydrous silicic acid, silicic acid, dicalcium phosphate, calcium carbonate and the like, particularly crystalline cellulose (e.g., microcrystalline cellulose and the like) is preferable. Examples of the water dispersible polymer include gum (e.g., gum tragacanth, acacia gum, guar gum), alginate (e.g., sodium alginate), cellulose derivative (e.g., methylcellulose, carboxymethylcellulose, hydroxymethylcellulose, hydroxypropylcellulose, hydroxypropylmethylcellulose), gelatin, soluble starch, polyacrylic acid (e.g., carbomer), polymethacrylic acid, polyvinyl alcohol, polyethylene glycol, polyvinylpyrrolidone, polycarbofil, ascorbic palmitate and the like, with preference given to hydroxypropylmethylcellulose, polyacrylic acid, alginate, gelatin, carboxymethylcellulose, polyvinylpyrrolidone, polyethylene glycol and the like. Particularly, hydroxypropylmethylcellulose is preferable. Examples of the stabilizer include cysteine, thiosorbitol, tartaric acid, citric acid, sodium carbonate, ascorbic acid, glycine, sodium sulfite and the like, particularly, citric acid and ascorbic acid are preferable.

The sublingual tablet, buccal and oral cavity rapid disintegrator can be produced by mixing the compound (aVa), (aVb), (bX), (bXI) or (cVII), or a combination drug and an excipient by a method know per se. Where desired, the above-mentioned auxiliaries such as a lubricant, an isotonic agent, a hydrophilic carrier, a water dispersible polymer, a stabilizer, a coloring agent, a sweetener, an antiseptic and the like may be contained. After mixing the above-mentioned components simultaneously or with time staggering, the mixture is compression formed under pressure to give sublingual tablet, buccal or oral cavity rapid disintegrator. To achieve a suitable hardness, a solvent such as water, alcohol and the like is used to moisten or wet as necessary before and after the compression forming. After the forming, the tablets may be dried.

When a mucous membrane adhesion tablet (film) is produced, the compound (aVa), (aVb), (bX), (bXI) or (cVII), or a combination drug and the above-mentioned water dispersible polymer (preferably, hydroxypropylcellulose, hydroxypropylmethylcellulose), an excipient and the like are dissolved in a solvent such as water and the like, and the obtained solution is cast to give a film. In addition, an additive such as a plasticizer, a stabilizer, an antioxidant, a preservative, a coloring agent, a buffer, a sweetener and the like may be added. To impart suitable elasticity to the film, glycols such as polyethylene glycol, propylene glycol and the like may be added, and to increase adhesion of the film to the oral cavity mucous membrane lining, bioadhesive polymer (e.g., polycarbofil, carbopol) may be added. The casting includes pouring the solution on a non-adhesive surface, spreading the solution in a uniform thickness (preferably about 10–1000 $\mu$) with a coating tool such as doctor blade and the like and drying the solution to give a film. The film thus formed may be dried at room temperature or under heating and cut into a desired surface area.

Examples of preferable oral cavity rapid disintegrator are a solid rapid diffusing administration agent having a net structure of the compound (aVa), (aVb), (bX), (bXI) or (cVII), or a combination drug and water soluble or water diffusable carrier which are inert to the compound (aVa), (aVb), (bX), (bXI) or (cVII), or a combination drug. The net structure can be obtained by sublimation of a solvent from the solid composition consisting of a solution obtained by dissolving the compound (aVa), (aVb), (bX), (bXI) or (cVII), or a combination drug in a suitable solvent.

The oral cavity rapid disintegrator preferably contains, in addition to the compound (aVa), (aVb), (bX), (bXI) or (cVII), or a combination drug, a matrix forming agent and a secondary component.

Examples of the matrix forming agent include animal proteins or vegetable proteins such as gelatins, dextrins, soybeans, wheat, psyllium seed protein and the like; rubber substances such as gum arabic, guar gum, agar, xanthan and the like; polysaccharides; alginic acids; carboxymethylcelluloses; carrageenans; dextrans; pectins; synthetic polymers such as polyvinylpyrrolidone and the like; a material derived from a gelatin-gum arabic complex and the like. In addition, saccharides such as mannitol, dextrose, lactose, galactose, trehalose and the like; cyclic saccharides such as cyclodextrin and the like; inorganic salts such as sodium phosphate, sodium chloride, aluminum silicate and the like; amino acid having 2 to 12 carbon atoms such as glycine, L-alanine, L-aspartic acid, L-glutamine acid, L-hydroxyproline, L-isoleucine, L-leucine, L-phenylalanine and the like are exemplified.

It is possible to introduce one or more matrix forming agents into a solution or suspension before preparation into a solid. Such matrix forming agent may exist with a surfactant or without a surfactant. The matrix forming agent can form a matrix, and also can help maintain the diffusion of the compound (aVa), (aVb), (bX), (bXI) or (cVII), or a combination drug in the solution or suspension.

The composition may contain a secondary component such as a preservative, an antioxidant, a surfactant, a thickener, a coloring agent, a pH adjusting agent, a flavor, a sweetener, a taste masking reagent and the like. Examples of a suitable coloring agent include red, black and yellow ferric oxides and FD&C dyes of Ellis & Everard, such as FD&C blue NO. 2, FD&C red No. 40 and the like. A suitable flavor contains mint, rasberry, licorice, orange, lemon, grapefruit, caramel, vanilla, cherry, grape flavor and a combination of these. Suitable pH adjusting agent includes citric acid, tartaric acid, phosphoric acid, hydrochloric acid and maleic acid. Suitable sweetener includes aspartame, acesulfame K, thaumatin and the like. Suitable taste masking agent includes sodium bicarbonate, ion exchange resin, cyclodextrin inclusion compound, adsorbent substance and microcapsuled apomorphine.

As the preparation, one containing the compound (aVa), (aVb), (bX), (bXI) or (cVII), or a combination drug generally in a proportion of about 0.1–about 50 wt %, preferably about 0.1–about 30 wt %, which is capable of dissolving 90% or more of the compound (aVa), (aVb), (bX), (bXI) or (cVII), or a combination drug in water for about 1 min––about 60 min, preferably about 1 min–about 15 min, more preferably about 2 min–about 5 min, such as the above-mentioned sublingual tablet, buccal and the like, and an oral cavity rapid disintegrator that disintegrates within 1–60 sec, preferably 1–30 sec, more preferably 1–10 sec, after being placed in an oral cavity, are preferable.

The content of the above-mentioned excipient in the whole preparation is about 10–about 99 wt %, preferably about 30–about 90 wt %. The content of the $\beta$-cyclodextrin or $\beta$-cyclodextrin derivative relative to the whole preparation is 0–about 30 wt %. The content of the lubricant relative to the whole preparation is about 0.01–about 10 wt %, preferably about 1–about 5 wt %. The content of the isotonicity agent relative to the whole preparation is about 0.1–about 90 wt %, preferably about 10–about 70 wt %. The content of the hydrophilic carrier relative to the whole preparation is about 0.1–about 50 wt %, preferably about 10–about 30 wt %. The content of the water dispersible polymer relative to the whole preparation is about 0.1–about 30 wt %, preferably about 10–about 25 wt %. The content of the stabilizer relative to the whole preparation is about 0.1–about 10 wt %, preferably about 1–about 5 wt %. The above-mentioned preparation may contain additives such as a coloring agent, a sweetener, an antiseptic and the like as necessary.

While the dose of the combination agent of the present invention varies depending on the kind of the compound (aVa), (aVb), (bX), (bXI) or (cVII), the patient's age, body weight and condition, the dosage form, the mode and the period of the treatment, the respective amounts of the compound (aVa), (aVb) (bX), (bXI) or (cVII) and combination drug may be, for example, about 0.01 to about 1000 mg/kg, preferably about 0.01 to about 100 mg/kg, more preferably about 0.1 to about 100 mg/kg, most preferably about 0.1 to about 50 mg/kg, and particularly about 1.5 to about 30 mg/kg per day, for a patient (adult weighing about 60 kg) with, for example, breast cancer, said daily dose being given intravenously once or in several portions during a day. It is a matter of course that a lower daily dose may be sufficient or an excessive dose may be required since the dose may vary depending on various factors as discussed above.

The combination drug may be contained in any amount as long as a side effect does not pose a problem. While the daily dose of the combination drug may vary depending on the disease state, age, sex, body weight and difference in sensitivity of the administration object, timing and interval of administration, characteristics, dispensing and kind of the pharmaceutical preparation, the kind of the active ingredient and the like, and is not particularly limited, the amount of the drug is generally about 0.001–2000 mg, preferably about 0.01–500 mg, more preferably about 0.1–100 mg, per 1 kg body weight of mammal by oral administration, which is generally administered once or in 2 to 4 portions during a day.

When the combination agent of the present invention is administered, it may be administered at the same time. However, a combination drug may be administered first, and then the compound (aVa), (aVb), (bX), (bXI) or (cVII) may be administered. Alternatively, the compound (aVa), (aVb), (bX), (bXI) or (cVII) may be administered first, and then a combination drug may be administered. For time stagger administration, the time difference varies depending on the active ingredient to be administered, dosage form and administration route. For example, when the combination drug is to be administered first, the compound (aVa), (aVb), (bX), (bXI) or (cVII) is administered within 1 min–3 days, preferably 10 min–1 day, more preferably 15 min–1 hour, after the administration of the combination drug. When the compound (aVa), (aVb), (bX), (bXI) or (cVII) is to be administered first, the combination drug is administered within 1 min–1 day, preferably 10 min–6 hours, more preferably 15 min–1 hour, after the administration of the compound (aVa), (aVb), (bX), (bXI) or (cVII).

A preferable administration method includes orally administering about 0.001–200 mg/kg of a combination drug prepared into a preparation for oral administration, and about 15 min later, orally administering about 0.005–100 mg/kg of the compound (aVa), (aVb), (bX), (bXI) or (cVII) prepared into a preparation for oral administration as an amount for the day.

In addition, the pharmaceutical composition of the present invention or the combination agent of the present invention may be combined with a therapy without medicine, such as (1) operation, (2) vasopressor chemotherapy using angiotensin II, (3) gene therapy, (4) thermotherapy, (5) cryotherapy, (6) laser cauterization therapy, (7) radiation therapy and the like.

For example, the use of the pharmaceutical composition of the present invention or the combination agent of the present invention before or after operation, or before or after a combined treatment of two or three kinds thereof affords effects such as prevention of expression of resistance, prolonged Disease-Free Survival time, suppression of metastasis or recurrence, life prolonging and the like.

It is also possible to combine a therapy with the pharmaceutical composition of the present invention or the combination agent of the present invention, with a supportive therapy such as (i) administration of antibiotics against complication with various infectious diseases (e.g., β-lactam group such as pansporin, macrolide group such as clarithromycin etc.), (ii) administration of total parenteral nutrition, amino acid preparation, multivitamin preparation for improvement of malnutrition, (iii) administration of morphine for relieving pain, (iv) administration of medicine to improve side effects such as nausea, vomition, anorexia, diarrhea, hypoleukocytemia, thrombocytopenia, decreased hemoglobin concentration, alopecia, hepatopathy, nephropathy, DIC., onset of fever and the like, and (v) administration of medicine to suppress multiple drug resistance in cancer, and the like.

It is preferable that the pharmaceutical composition of the present invention or the combination agent of the present invention be administered before or after the aforementioned treatment by oral administration (inclusive of sustained release administration), intravenous administration (inclusive of bolus, infusion and inclusion compound), subcutaneous or intramuscular injection (inclusive of bolus, infusion, sustained release administration), transdermal, intra-tumor and proximal administrations.

When the pharmaceutical composition of the present invention or the combination agent of the present invention is administered before operation, for example, it may be administered once at about 30 min to 24 hours before the operation etc., or may be administered at about 3 to 6 months before the operation etc. in 1 to 3 cycles. The administration of the pharmaceutical composition of the present invention or the combination agent of the present invention before operation decreases size of, for example, cancer tissues, thereby facilitating the operation etc.

When the pharmaceutical composition of the present invention or the combination agent of the present invention is administered after operation, for example, it may be repeat administered at about 30 min to 24 hours after the operation etc. for several weeks to 3 months. The administration of the pharmaceutical composition of the present invention or the combination agent of the present invention after operation enhances the effect of the operation.

EXAMPLES

While the present invention is explained in detail in the following by referring to Reference Examples and Examples, the present invention is not limited by these Examples.

The abbreviations used in the description mean the following.

s: singlet d: doublet t: triplet m: multiplet

J: coupling constant

Hz: Hertz $CDCl_3$: Deuterated Chloroform

DMSO-$d_6$: Deuterated dimethyl sulfoxide $D_2O$: deuterium oxide $^1$H-NMR: protone nuclear magnetic resonance HPLC: high performance liquid chromatography Me: methyl Room Temperature: 15 to 30° C.

$^1$H-NMR spectrum was measured by Bruker DPX 300 (300 MHz) type Spectrometer using tetramethylsilane as an internal standard. All δ values are shown in ppm.

HPLC Conditions in Example 4 column: Inertsil (trademark) ODS-3 (4.6×150 mm I.D.) (GL Science Inc.)

mobile phase: 0.05M potassium dihydrogen phosphate /acetonitrile=45/55 wavelength: 254 nm temperature: 25° C.

flow: 1 ml/min

HPLC conditions in Reference Example 12, Example 21 and Example 22
- column: YMC-Pack ODS-A A-302(150×4.6 mm I.D.) (trademark, YMC Co., Ltd)
- mobile phase: 0.05M potassium dihydrogen phosphate/acetonitrile=45/55
- wavelength: 270 nm
- temperature: 25° C.
- Flow: 1 ml/min Powder X ray diffraction was measured using X-ray Diffractometer RINT Ultima+(Rigaku).

Reference Example 1

Production of 4-chloro-1-(4-methoxyphenyl)-1-butanone

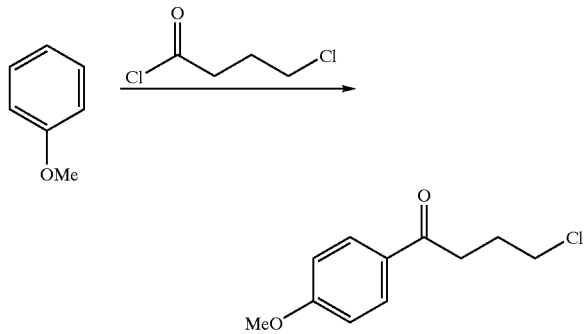

Anisole (6.75 g, 62.4 mmol) was dissolved in dichloromethane (80 ml). The mixture was cooled to −5° C. and aluminum chloride (8.32 g, 62.4 mmol) was added. 4-Chlorobutyryl chloride (8.8 g, 62.4 mmol) was added dropwise to the mixture at −10° C. and stirred at −10° C. for 1 hour. The reaction mixture was poured into iced water (100 ml). After separation, the organic layer was washed with 1N hydrochloric acid (50 ml), saturated aqueous sodium hydrogen carbonate (50 ml) and water (50 ml), and was concentrated under reduced pressure to give 4-chloro-1-(4-methoxyphenyl)-1-butanone (12.7 g).

yield 96%.

$^1$H-NMR (CDCl$_3$, δ, 300 MHz) 2.19–2.24(2H,m), 3.13 (2H,t,J=7.0 Hz), 3.67(2H,t,J=6.2 Hz), 3.87(3H,s), 6.92–6.96 (2H,m), 7.94–7.98(2H,m).

Reference Example 2

Production of 4-chloro-1-(4-methoxyphenyl)-1-butanone

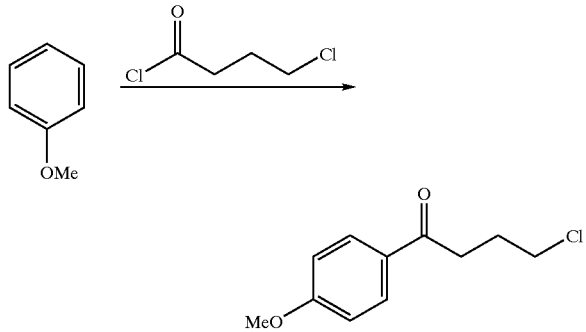

Anisole (2.16 g, 20 mmol) was dissolved in toluene (20 ml). The mixture was cooled to −10° C. and aluminum chloride (2.67 g, 20 mmol) was added. 4-Chlorobutyryl chloride (2.47 ml, 22 mmol) was added dropwise at −10° C. and stirred for 0.5 hour at −10° C. The reaction mixture was poured into iced water (40 ml). After separation, the organic layer was washed with 20%citric acid (10 ml) twice, 1N-sodium hydroxide (10 ml) and 20% brine (10 ml) twice, and was concentrated under reduced pressure to give 4-chloro-1-(4-methoxyphenyl)-1-butanone (4.21 g, yield 99%).

Reference Example 3

Production of 1-(4-chlorobutyl)-4-methoxybenzene

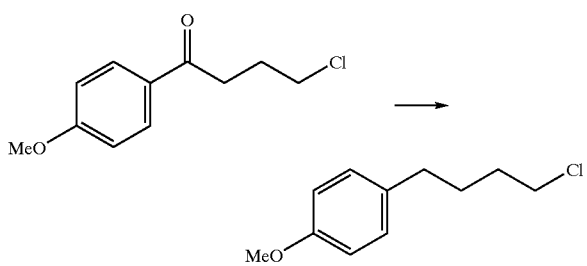

4-Chloro-1-(4-methoxyphenyl)-1-butanone (5 g, 23.5 mmol) was dissolved in tetrahydrofuran (50 ml). 10% Palladium carbon (water-containing product, 500 mg) was added and the mixture was subjected to catalytic reduction under hydrogen pressure (0.8 MPa, 50° C. for 3 h). The catalyst was filtered off and the filtrate was concentrated under reduced pressure to give 1-(4-chlorobutyl)-4-methoxybenzene (4.6 g, yield 99%).

$^1$H-NMR (CDCl$_3$, δ, 300 MHz) 1.69–1.83(4H,m), 2.59 (2H,t,J=7.4 Hz), 3.54(2H,t,J=6.2 Hz), 3.79(3H,s), 6.81–6.85 (2H,m), 7.08–7.11(2H,m).

EXAMPLE 1

Production of 1-[4-(4-methoxyphenyl)butan-1-yl]-1H-1,2,3-triazole methanesulfonate

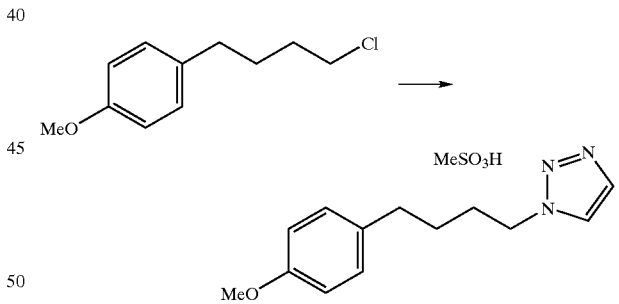

1-(4-Chlorobutyl)-4-methoxybenzene (950 mg, 4.78 mmol), 1H-1,2,3-triazole (660 mg, 9.55 mmol) and potassium iodide (793 mg, 4.78 mmol) were added to t-butanol (5 ml). Sodium hydroxide (382 mg, 9.55 mmol) was added and the mixture was refluxed under heating for 11 hours. After cooling to room temperature, toluene and water were added and the mixture was partitioned. The organic layer was washed successively with water, 20% citric acid, saturated aqueous sodium hydrogen carbonate and water, and was concentrated under reduced pressure. To the residue were added ethyl acetate (6 ml) and isopropyl ether (3 ml). Methanesulfonic acid (402 mg, 4.18 mmol) was added at room temperature. Ethyl acetate/isopropyl ether=2/1 (2 ml) was added and the mixture was stirred at room temperature for 30 min. The precipitated crystals were collected by filtration and dried under reduced pressure to give 1-[4-(4-methoxyphenyl)-butan-1-yl]-1H-1,2,3-triazole methanesulfonate (1.14 g, yield 73%).

$^1$H-NMR (DMSO-d$_6$, δ, 300 MHz) 1.40–1.51(2H,m), 1.74–1.84(2H,m) 2.39(3H,s), 2.51(2H,t,J=7.7 Hz), 3.69(3H, s), 4.38(2H,t,J=7.0 Hz), 6.79–6.84(2H,m), 7.04–7.09(2H, m), 7.71(1H,d,J=0.7 Hz), 8.11(1H,d,J=0.7 Hz).

EXAMPLE 2

Production of 1-[4-(4-methoxyphenyl)butan-1-yl]-1H-1, 2,3-triazole methanesulfonate

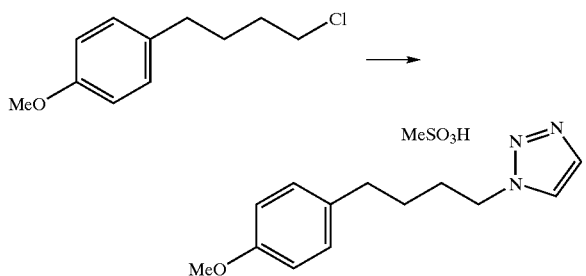

To 1-(4-Chlorobutyl)-4-methoxybenzene (2468 mg, 12.42 mmol) was added 2-methyl-2-butanol (5 ml), and then 1H-1,2,3-triazole (1286 mg, 18.62 mmol) and potassium iodide (2062 mg, 14.24 mmol) were added. Sodium hydroxide (745 mg, 18.62 mmol) was added and the mixture was refluxed under heating for 4 hours. After cooling to room temperature, toluene and water were added and the mixture was partitioned. The organic layer was washed with water, 20%citric acid (twice), saturated aqueous sodium hydrogen carbonate and water (twice). The organic layer was concentrated under reduced pressure. To the residue was added ethyl acetate and the mixture was concentrated under reduced pressure. Ethyl acetate (20 ml) and isopropyl ether (10 ml) were added and then seed crystal was added. Methanesulfonic acid (1021 mg, 10.62 mmol) was added dropwise while keeping the mixture at 20–30° C. The mixture was stirred at 20–30° C. for 1 hour. The precipitated crystals were collected by filtration and washed with ethyl acetate/isopropyl ether=1/1. The crystals were dried under reduced pressure to give 1-[4-(4-methoxyphenyl)butan-1-yl]-1H-1,2,3-triazole methanesulfonate (3.04 g) as white crystals (yield 75%).

$^1$H-NMR (DMSO-d$_6$, δ, 300 MHz) 1.40–1.51(2H,m), 1.74–1.84(2H,m) 2.39(3H,s), 2.51(2H,t,J=7.7 Hz), 3.69(3H, s), 4.38(2H,t,J=7.0 Hz), 6.79–6.84(2H,m), 7.04–7.09(2H, m), 7.71(1H,d,J=0.7 Hz), 8.11(1H,d,J=0.7 Hz)

EXAMPLE 3

Production of 1-[4-(4-methoxyphenyl)butan-1-yl]-1H-1, 2,3-triazole hydrochloride

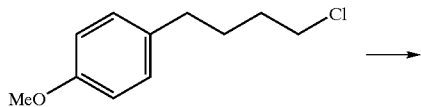

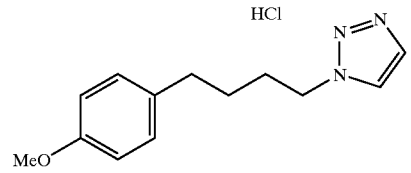

1-(4-Chlorobutyl)-4-methoxybenzene (993 mg, 5 mmol), 1H-1,2,3-triazole (691 mg, 10 mmol), potassium iodide (830 mg, 5 mmol) and lithium chloride (424 mg, 10 mmol) were added to t-butanol (5 ml), and t-butoxysodium (961 mg, 10 mmol) was added. The mixture was refluxed under heating for 17 hours. After cooling to room temperature, toluene and water were added and the mixture was partitioned. The organic layer was washed with water, 20% citric acid (three times), saturated aqueous sodium hydrogen carbonate and water, and concentrated under reduced pressure. To the residue was added ethanol (30 ml). Concentrated hydrochloric acid (2 ml) was added and the mixture was concentrated under reduced pressure. To the residue was added 2-propanol, and after concentration under reduced pressure, ethyl acetate was added. The mixture was concentrated under reduced pressure and ethyl acetate (3 ml) was added. The mixture was stirred at room temperature for 45 min. The precipitated crystals were collected by filtration and dried under reduced pressure to give 1-[4-(4-methoxyphenyl) butan-1-yl]-1H-1,2,3-triazole hydrochloride (772 mg, yield 58%).

$^1$H-NMR (DMSO-d$_6$, δ, 300 MHz) 1.39–1.50(2H,m), 1.73–1.83(2H,m) 2.49(2H,t,J=7.6 Hz), 3.68(3H,s), 4.37(2H, t,J=7.0 Hz), 6.77–6.83(2H,m), 7.02–7.07(2H,m), 7.73(1H, d,J=0.7 Hz), 8.13(1H,d,J=0.7 Hz).

EXAMPLE 4

Production of 1-[4-(4-methoxyphenyl)butan-1-yl]-1H-1, 2,3-triazole

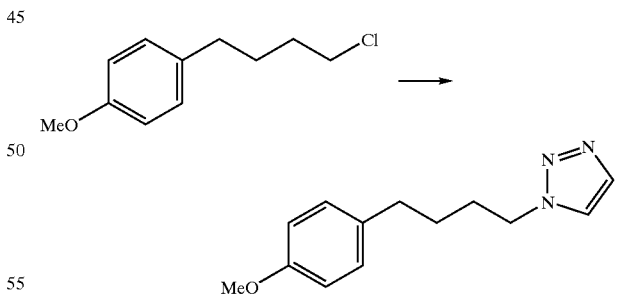

1-(4-Chlorobutyl)-4-methoxybenzene (993 mg, 5 mmol), 1H-1,2,3-triazole (691 mg, 10 mmol) and potassium iodide (830 mg, 5.0 mmol) were dissolved in dimethylformamide (5 ml) and the mixture was stirred at 100° C. for 2.5 hours. After cooling the reaction mixture to room temperature, ethyl acetate and water were added, and the mixture was partitioned. The organic layer was measured by HPLC. As a result, 1-[4-(4-methoxyphenyl)butan-1-yl]-1H-1,2,3-triazole (550 mg) was found to be present (yield 48%).

Reference Example 4

Production of 4-[4-(1H-1,2,3-triazol-1-yl)butyl]phenol

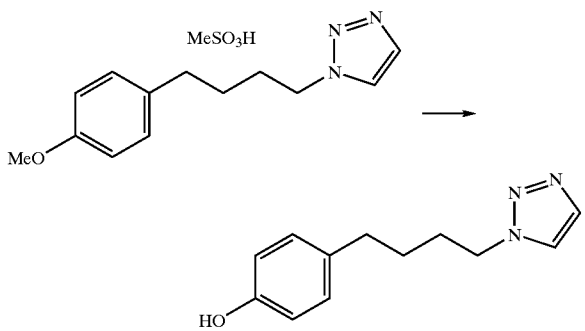

1-[4-(4-Methoxyphenyl)butan-1-yl]-1H-1,2,3-triazole methanesulfonate (4.0 g, 12.22 mmol) was added into 48% hydrobromic acid (8 ml) and the mixture was heated at 80–90° C. for 6 hours. The reaction mixture was ice-cooled and 4N-sodium hydroxide (32 ml) was added dropwise. The mixture was washed with toluene. 6N Hydrochloric acid was added to the aqueous layer to adjust pH to 6.3. The mixture was extracted with ethyl acetate (30 ml) and tetrahydrofuran (15 ml) and then washed with water. Activated carbon (200 mg) was added and the mixture was stirred at room temperature for 10 min. The mixture was filtrated and concentrated under reduced pressure. To the residue was added ethyl acetate (10 ml), and the mixture was refluxed. After allowing to cool and stirring for 30 min, hexane (10 ml) was added and the mixture was stirred at room temperature for 30 min. The precipitated crystals were collected by filtration and dried under reduced pressure to give 4-[4-(1H-1,2,3-triazol-1-yl)butyl]phenol (2.25 g, yield 85%).

$^1$H-NMR (CDCl$_3$-DMSO-d$_6$, δ, 300 MHz) 1.48–1.59(2H, m), 1.80–1.91(2H,m), 2.49(2H,t,J=7.5 Hz), 4.31(2H,t,J=7.2 Hz), 6.68–6.73(2H,m), 6.87–6.91(2H,m), 7.45(1H,d,J=0.7 Hz), 7.61(1H,d,J=0.7 Hz), 8.12(1H,s).

Reference Example 5

Production of 4-(trifluoromethyl)cinnamamide

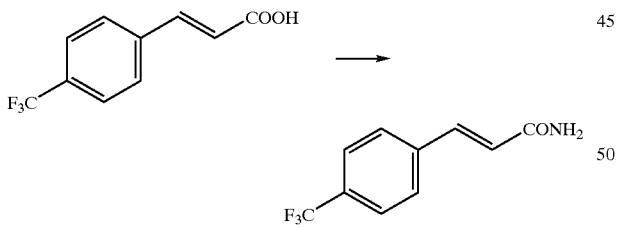

4-(Trifluoromethyl)cinnamic acid (64.85 g, 300 mmol) was added to toluene (325 ml) and dimethylformamide (2.2 ml). Thionyl chloride (26.3 ml, 361 mmol) was added dropwise at room temperature. The mixture was heated at 45° C. for 2 hours. The obtained reaction mixture was added dropwise to 25% aqueous ammonia (325 ml) while keeping the mixture at 5–20° C. The mixture was stirred at room temperature for 1 hour. The crystals were filtered, washed with water and isopropyl ether and dried under reduced pressure to give 4-(trifluoromethyl)-cinnamamide (60.76 g, yield 94%). H-NMR (CDCl$_3$-DMSO-d$_6$, δ, 300 MHz) 5.93 (1H,s), 6.53(1H,d,J=15.8 Hz), 6.75(1H,s), 7.48–7.53(5H, m).

Reference Example 6

Production of 4-(chloromethyl)-2-[(E)-2-[4-(trifluoromethyl)-phenyl]ethenyl]-1,3-oxazole

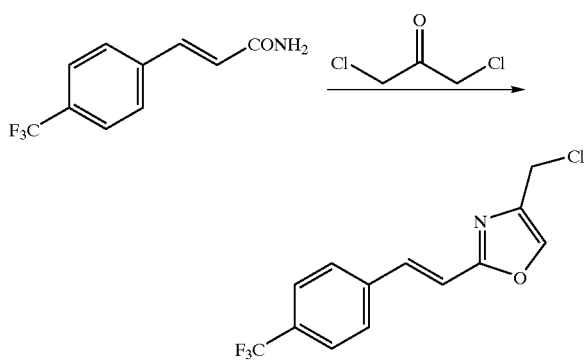

4-(Trifluoromethyl)cinnamamide (1 g, 4.65 mmol) and 1,3-dichloroacetone (1.1 g, 8.66 mmol) were added to toluene (5 ml) and the mixture was refluxed under heating for 8 hours. Ethyl acetate (20 ml) was added and the mixture was washed with water (20 ml) twice, and then concentrated under reduced pressure. To the residue was added methanol (4 ml) and the mixture was stirred at room temperature. The crystals were filtrated and dried under reduced pressure to give 4-(chloromethyl)-2-[(E)-2-[4-(trifluoromethyl)phenyl] ethenyl]-1,3-oxazole (733 mg, yield 55%).

$^1$H-NMR (CDCl$_3$, δ, 300 MHz) 4.56(2H,s), 7.01(1H,d,J= 16.4 Hz), 7.54–7.68(6H,m).

Reference Example 7

Production of 1-[4-[4-[[2-[(E)-2-[4-(trifluoromethyl) phenyl]ethenyl]-1,3-oxazol-4-yl]methoxy]phenyl]butyl]-1H-1,2,3-triazole

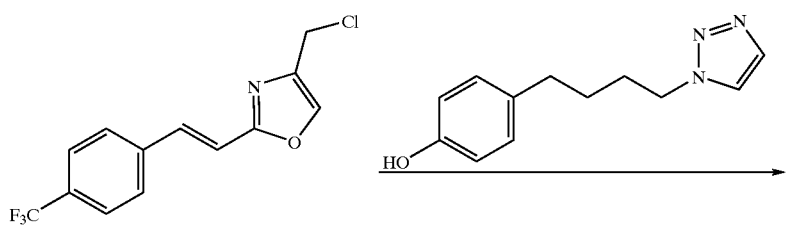

-continued

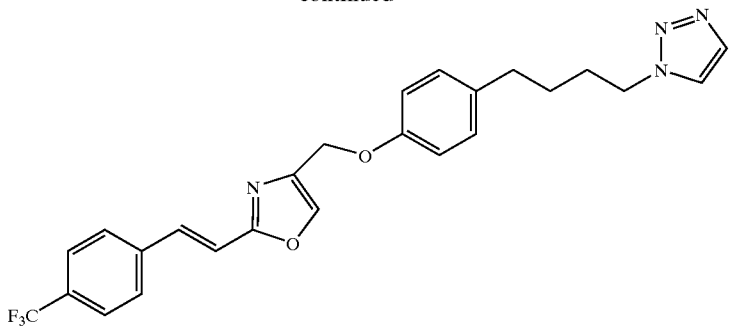

4-[4-(1H-1,2,3-Triazol-1-yl)butyl]phenol (400 mg, 1.84 mmol) and 4-(chloromethyl)-2-[(E)-2-[4-(trifluoromethyl)phenyl]ethenyl]-1,3-oxazole (529 mg, 1.84 mmol) were dissolved in dimethylformamide (3 ml) and potassium carbonate (279 mg, 2.02 mmol) was added. The mixture was stirred at 65–75° C. for 4 hours. 4-[4-(1H-1,2,3-Triazol-1-yl)butyl]phenol (40 mg, 0.184 mmol) was added and the mixture was stirred at 65–75° C. for further 3 hours. The mixture was cooled to room temperature and water (5 ml) was added, then methanol (3 ml) was added. The mixture was stirred at room temperature for 40 min, and the precipitated crystals were collected by filtration and washed with water. The crystals were dried under reduced pressure to give 1-[4-[4-[[2-[(E)-2-[4-(trifluoromethyl)phenyl]ethenyl]-1,3-oxazol-4-yl]methoxy]phenyl]butyl]-1H-1,2,3-triazole (799 mg, yield 93%).

$^1$H-NMR (CDCl$_3$, δ, 300 MHz) 1.57–1.68(2H,m), 1.88–1.99(2H,m), 2.60(2H,t,J=7.5 Hz), 4.39(2H,t,J=7.–1 Hz), 5.01(2H,s), 6.89–7.08(5H,m), 7.49–7.70(8H,m).

EXAMPLE 5

Production of 4-[4-(tert-butoxy)phenyl]butyl methanesulfonate

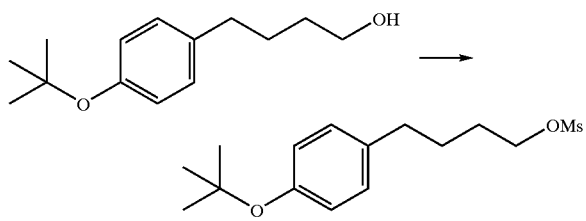

To the kolben were added 4-[4-(tert-butoxy)phenyl]butyl methanesulfonate (33.66 g), sodium iodide (22.49 g) and acetone (337 ml), and the mixture was reacted for 1 hour by reflux under heating. To the reaction mixture were added water (500 ml) and diisopropyl ether (500 ml). After stirring, the mixture was left standing and partitioned to separate the organic layer. The organic layer was washed successively with saturated aqueous sodium hydrogen carbonate (250 ml), 10% solution of Na$_2$S$_2$O$_3$ (250 ml) twice and water (250 ml). The organic layer was concentrated under reduced pressure to give the objective compound (35.8 g) as a concentrated residue.

$^1$H-NMR (CDCl$_3$, 300 MHz) ppm: 1.33(9H,s), 1.6–1,8 (4H,m), 2.62(2H, t, J=7.1), 2.99(3H,s), 4.24(2H,t,J=6.1), 6.91(2H,d,J=8.5 Hz), 7.05(2H,d,J=8.5 Hz)

Reference Example 8

Production of 1-tert-butoxy-4-(4-iodobutyl)benzene

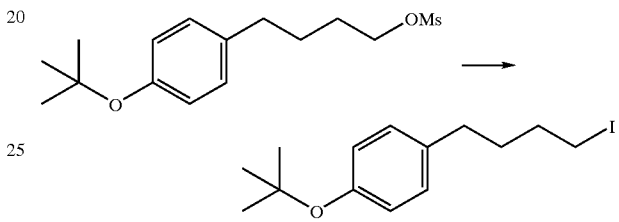

To the kolben were added 4-[4-(tert-butoxy)phenyl]butyl methanesulfonate (33.66 g), sodium iodide (22.49 g) and acetone (337 ml), and the mixture was reacted for 1 hour by reflux under heating. To the reaction mixture were added water (500 ml) and diisopropyl ether (500 ml). After stirring, the mixture was left standing and partitioned to separate the organic layer. The organic layer was washed successively with saturated aqueous sodium hydrogen carbonate (250 ml), 10% hypo (250 ml) twice and water (250 ml). The organic layer was concentrated under reduced pressure to give the objective compound (35.8 g) as a concentrated residue.

$^1$H-NMR (CDCl$_3$, 300 MHz) ppm: 1.33(9H,s), 1.6–1.7 (2H,m), 1,8–1.9(2H,m), 2.59(2H,t,J=7.5 Hz), 3.20(2H,t,J=6.9 Hz), 6.90(2H,d,J=8.4 Hz), 7.04(2H,d,J=8.4 Hz)

EXAMPLE 6

Production of 4-[4-(tert-butoxy)phenyl]butyl (4-methylbenzene)-sulfonate

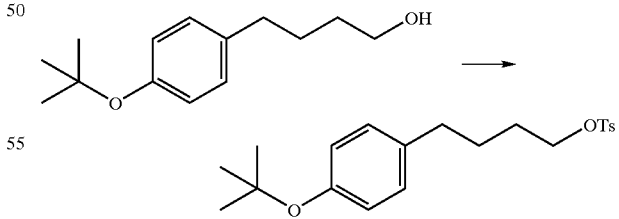

To the kolben were added 4-[4-(tert-butoxy)phenylbutan-1-ol (5.28 g) and pyridine (9 ml), and the mixture was stirred. Toluenesulfonyl chloride (5.70 g, 1.5 eq) was added at an inner temperature of 5° C. and the mixture was allowed to react at room temperature for 2 hours. Water (20 ml) was added at not higher than 10° C. and the mixture was stirred for 5 min. Ethyl acetate (40 ml) was added and the aqueous layer was separated. The organic layer was washed with 10% aqueous boric acid (20 ml) three times and with water (20 ml) once. The organic layer was concentrated under reduced pressure to give a concentrated residue (8.80 g) of the objective compound.

This was applied to silica gel chromatography and the effective fraction was concentrated to give the objective compound (6.40 g).

$^1$H-NMR (CDCl$_3$, 300 MHz) ppm: 1.32(9H,s), 1.5–1.7 (4H,m), 2.45(3H,s), 2.52(2H,t,J=7.–1 Hz), 4.04(2H,t,J=6.0 Hz), 6.87(2H,d,J=8.5 Hz), 6.98(2H,d,J=8.5 Hz), 7.33(2H,d, J=8.1 Hz), 7.78(2H,d,J=8.1 Hz)

EXAMPLE 7

Production of 1-tert-butoxy-4-(4-chlorobutyl)benzene

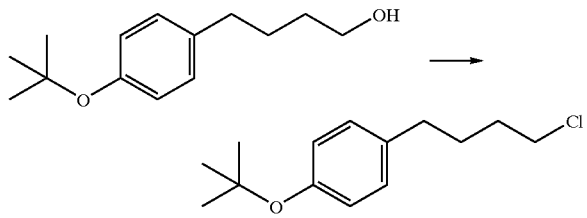

To a solution of 4-[4-(tert-butoxy)phenyl-butan-1-ol (44.7 g), toluene (220 ml) and triethylamine (30.4 g) was added dropwise thionyl chloride (28.6 g) at an inner temperature 60° C. over about 2 hours, and the mixture was reacted for 4 hours. Water (90 ml) was added to separate the organic layer. The organic layer was washed with 5% sodium hydrogen carbonate (90 ml) and water (90 ml), and dried over anhydrous magnesium sulfate. The organic layer was concentrated and evaporated under reduced pressure (128–130° C./0.2 mmHg) to give the objective compound (34.3 g).

1H-NMR (CDCl$_3$, 300 MHz) ppm: 1.32(9H,s), 1.7–1.8 (4H,m), 2.60(2H,t,J=7.2 Hz), 3.55(2H,t,J=6.2), 6.90(2H,d, J=8.4 Hz), 7.06(2H,d,J=8.4 Hz)

EXAMPLE 8

Production of 1-tert-butoxy-4-(4-chlorobutyl)benzene

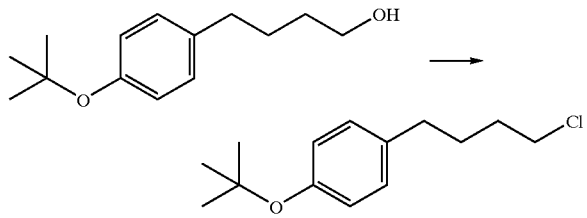

To the kolben were added 4-[4-(tert-butoxy)phenyl-butan-1-ol (5.0 g) and pyridine (15 ml), and the mixture was stirred. To the mixture was added dropwise methanesulfonyl chloride (3.84 g) under ice-cooling. The mixture was heated to about 60° C. and reacted for 2 hours. To the reaction mixture were added toluene (25 ml) and water (25 ml), and the mixture was stirred, left standing and partitioned. The organic layer was washed with water (25 ml) twice. The organic layer was concentrated to give the objective compound (4.27 g) as a concentrated residue.

EXAMPLE 9

Production of 1-[4-(4-tert-butoxyphenyl)butan-1-yl]-1H-1,2,3-triazole

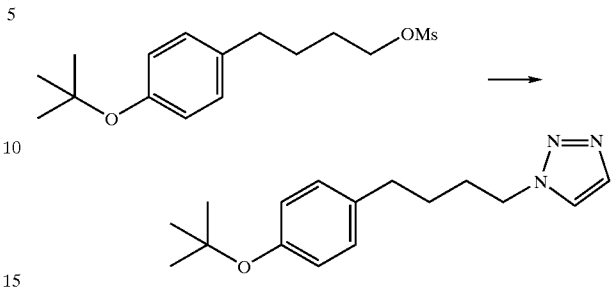

To the kolben were added 1H-1,2,3-triazole (5.18 g), sodium iodide (7.49 g), sodium hydroxide (3.0 g) and 2-methyl-2-butanol (20 ml), and the mixture was refluxed under heating for 1 hour (inner temperature then was 100–102° C.). A solution of 4-[4-(tert-butoxy)phenyl]butyl methanesulfonate (15.09 g)/2-methyl-2-butanol (20 ml) was added dropwise over about 1 hour 40 min. The mixture was reacted at the same temperature for 3 hours. After cooling, the mixture was concentrated. To the residue were added water (20 ml) and toluene (20 ml), and the mixture was stirred. After standing and partitioning, the organic layer was washed with 5% aqueous sodium hydrogen carbonate (20 ml) and then with water (20 ml). The organic layer was concentrated to give objective compound (12.72 g) as a concentrated residue.

$^1$H-NMR (CDCl$_3$, 300 MHz) ppm :1.35(9H,s), 1.6–1.7 (2H,m), 1.9–2.0(2H,m), 2.63(2H,t,J=7.6 Hz), 4.41(2H,t,J= 7.–1 Hz), 6.91(2H,d,J=8.5 Hz), 7.04(2H,d,J=8.5),7.51(1H, d,J=0.8), 7.71(1H,d,J=0.8)

EXAMPLE 10

Production of 1-[4-(4-tert-butoxyphenyl)butan-1-yl]-1H-1,2,3-triazole

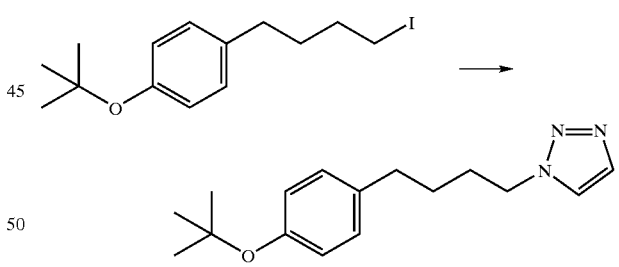

To the kolben were added sodium hydroxide (3.0 g), 1H-1,2,3-triazole (5.18 g) and 2-methyl-2-butanol (20 ml), and the mixture was refluxed under heating for 1 hour (inner temperature then was 100–102° C.). A solution of 1-tert-butoxy-4-(4-iodobutyl)benzene (17.9 g)/2-methyl-2-butanol (20 ml) was added dropwise over about 1 hour 50 min. The mixture was reacted at the same temperature for 3 hours. After cooling, the mixture was concentrated. To the residue were added water (20 ml) and toluene (20 ml), and the mixture was stirred. After standing and partitioning, the organic layer was washed with 5% aqueous sodium hydrogen carbonate (20 ml) and then with water (20 ml). The organic layer was concentrated to give objective compound (15.6 g) as a concentrated residue.

EXAMPLE 11

Production of 1-[4-(4-tert-butoxyphenyl)butan-1-yl]-1H-1,2,3-triazole

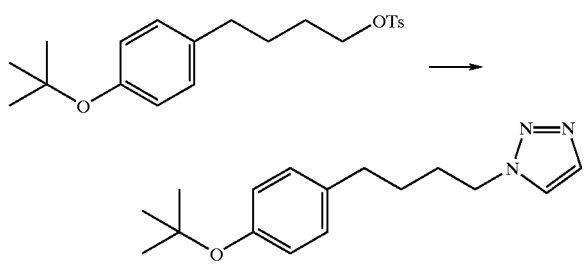

To the kolben were added 1H-1,2,3-triazole (1.65 g), sodium iodide (3.58 g), sodium hydroxide (0.96 g) and 2-methyl-2-butanol (7 ml), and the mixture was refluxed under heating for 1 hour (inner temperature then was 100–102°C.). A solution of 4-[4-(tert-butoxy)phenyl]butyl (4-methylbenzene)sulfonate (6.00 g)/2-methyt-2-butanol (7 ml) was added dropwise over about 1 hour. The mixture was reacted at the same temperature for 3 hours. After cooling, the mixture was concentrated. To the residue were added water (10 ml) and toluene (20 ml), and the mixture was stirred. After standing and partitioning, the organic layer was washed with 5% aqueous sodium hydrogen carbonate (10 ml) and then with water (10 ml). The organic layer was concentrated to give objective compound (4.10 g) as concentrated residue.

EXAMPLE 12

Production of 1-[4-(4-tert-butoxyphenyl)butan-1-yl]-1H-1,2,3-triazole

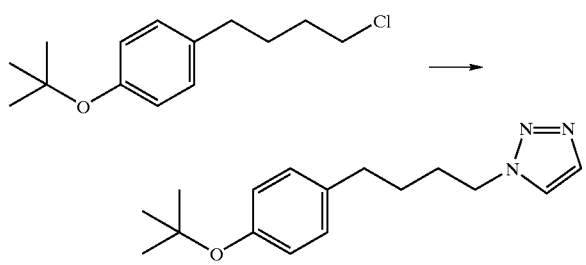

To the kolben were added 1H-1,2,3-triazole (5,18 g), sodium iodide (7.48 g), sodium hydroxide (3.0 g) and 2-methyl-2-butanol (20 ml), and the mixture was refluxed under heating for 1 hour. A solution of 1-tert-butoxy-4-(4-chlorobutyl)benzene (12.04 g)/2-methyl-2-butanol (20 ml) was added dropwise over about 2 hours, and the mixture was reacted at inner temperature 100–102° C. for 2 hours. Water (20 ml) and toluene (20 ml) was added and the mixture was stirred, left standing and partitioned to separate the aqueous layer. The organic layer was washed successively with 5% aqueous sodium hydrogen carbonate (20 ml) and water (20 ml). The organic layer was concentrated to give the objective compound (13.55 g) as a concentrated residue.

Reference Example 9

Production of 4-[4-(1H-1,2,3-triazol-1-yl)butyl]phenol

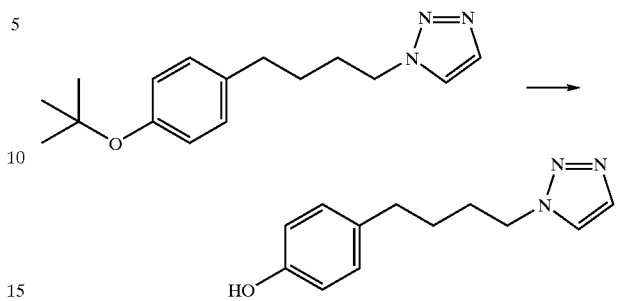

To the kolben were added 1-[4-(4-tert-butoxyphenyl)butan-1-yl]-1H-1,2,3-triazole (10.0 g) and 4N-hydrochloric acid (40 ml), and the mixture was reacted at 49–52° C. for 1 hour. After completion of the reaction, 30% sodium hydroxide (18 ml) was added and the mixture was extracted with ethyl acetate (100 ml). The organic layer was washed with 5% aqueous sodium hydrogen carbonate (50 ml) and water (50 ml), and the organic layer was concentrated to dryness. To the concentrated residue was added ethyl acetate (15 ml) and the mixture was refluxed under heating for about 30 min. The mixture was allowed to cool with stirring for 1 hour, and stirred at 5–10° C. for 1 hour. The precipitated crystals were collected by filtration and washed with cold-ethyl acetate (2.5 ml).

Wet crystals were dried under reduced pressure at an outer temperature of 40° C. to give 4-[4-(1H-1,2,3-triazol-1-yl)butyl]phenol (5.51 g).

Reference Example 10

Production of 4-[4-(1H-1,2,3-triazol-1-yl)butyl]phenol

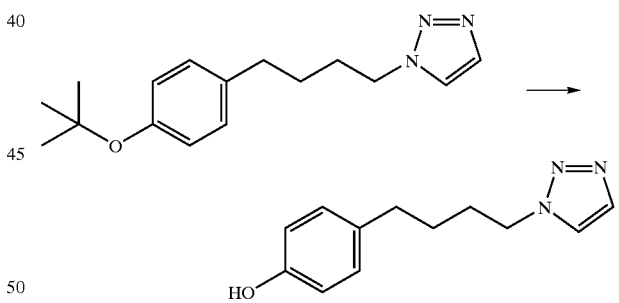

To the kolben were added 1-[4-(4-tert-butoxyphenyl)butan-1-yl]-1H-1,2,3-triazole (10.0 g) and 4N-hydrochloric acid (40 ml), and the mixture was heated to about 50° C. and reacted for 1 hour. The reaction mixture was adjusted to pH 2.5 with 30% aqueous sodium hydroxide, and extracted with ethyl acetate (140 ml). The organic layer was washed successively with saturated sodium hydrogen carbonate (50 ml) and water (50 ml), and the organic layer was concentrated. To the residue was added ethyl acetate (20 ml) and the mixture was heated under reflux to dissolve the residue, which was then allowed to cool to allow crystallization. The mixture was cooled to about 5° C. and stirred for 1 hour. The precipitated crystals were collected by filtration and washed with cold-ethyl acetate (25 ml). Wet crystals were dried to give the objective compound (6.14 g).

EXAMPLE 13

Production of 1-(4-phenylbutyl)-1H-1,2,3-triazole

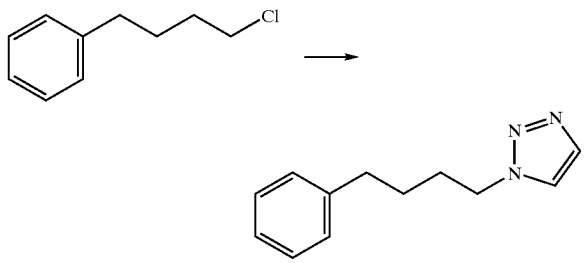

1,2,3-Triazole (1623 mg, 23.5 mmol), sodium iodide (2353 mg, 15.7 mmol) and sodium hydroxide (940 mg, 23.5 mmol) were added to t-amyl alcohol (6.2 ml), and the mixture was refluxed under stirring for 1 hour. 1-Chloro-4-phenylbutane (2648 mg, 15.7 mmol) was dissolved in t-amyl alcohol (6.2 ml) and added dropwise under reflux over 1 hour. The mixture was refluxed under stirring for 2 hours and cooled to room temperature, and toluene (50 ml) was added. The mixture was washed with water (50 ml×2), dried over anhydrous sodium sulfate and concentrated under reduced pressure. The residue was purified by silica gel column chromatography (hexane/ethyl acetate=4/1→1/3) to give 1-(4-phenylbutyl)-1H-1,2,3-triazole (2.56 g) as colorless oil. yield 81%. 2-(4-Phenylbutyl)-2H-1,2,3-triazole (360 mg) was obtained as a colorless oil (yield 11%). 1-(4-phenylbutyl)-1H-1,2,3-triazole $^1$H-NMR (CDCl$_3$, δ, 300 MHz) 1.59–1.70(2H,m), 1.87–2.00(2H,m), 2.65(2H,t,J=7.54 Hz), 4.39(2H,t,J=7.12 Hz), 7.12–7.30(5H,m), 7.50(1H,s), 7.69(1H,s) 2-(4-phenylbutyl)-2H-1,2,3-triazole $^1$H-NMR (CDCl$_3$, δ, 300 MHz) 1.58–1.67(2H,m), 1.96–2.07(2H,m) 2.65(2H,t,J=7.63 Hz), 4.47(2H,t,J=7.04 Hz), 7.13–7.30(5H,m), 7.59(2H,s).

EXAMPLE 14

Production of 1-(2-phenylethyl)-1H-1,2,3-triazole

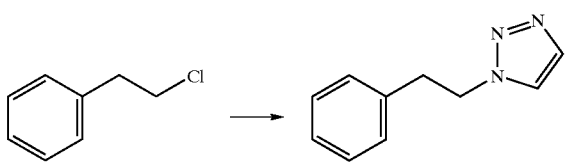

1,2,3-Triazole (1634 mg, 23.7 mmol), sodium iodide (2364 mg, 15.8 mmol), sodium hydroxide (946 mg, 23.7 mmol) were added to t-amyl alcohol (6.2 ml), and the mixture was refluxed under stirring for 1 hour. 1-Chloro-2-phenylethane (2217 mg, 15.8 mmol) was dissolved in t-amyl alcohol (6.2 ml) and added dropwise under reflux over 1 hour. The mixture was refluxed under stirring for 3.5 hours. The mixture was cooled to room temperature and toluene (50 ml) was added. The mixture was washed with water (50×2), dried over anhydrous sodium sulfate and concentrated under reduced pressure. The residue was purified by silica gel column chromatography (hexane/ethyl acetate=3/1→1/3) to give 1-(2-phenylethyl)-1H-1,2,3-triazole as a colorless oil (2.0 g, yield 73%). 2-(2-Phenylethyl)-2H-1,2,3-triazole (315 mg) was obtained as a colorless oil (yield 12%). 1-(4-phenylethyl)-1H-1,2,3-triazole $^1$H-NMR (CDCl$_3$, δ, 300 MHz) 3.32(2H,t,J=7.20 Hz), 4.62(2H,t,J=7.17 Hz), 7.07–7.11(2H,m), 7.21–7.32(4H,m), 7.61(1H,s). 2-(4-phenylethyl)-2H-1,2,3-triazole $^1$H-NMR (CDCl$_3$, δ, 300 MHz) 3.28(2H,t,J=7.79 Hz) 4.68(2H,t,J=7.60 Hz), 7.15–7.32(5H,m), 7.59(2H,s).

EXAMPLE 15

Production of 1-phenyl-2-(1H-1,2,3-triazol-1-yl)ethanone

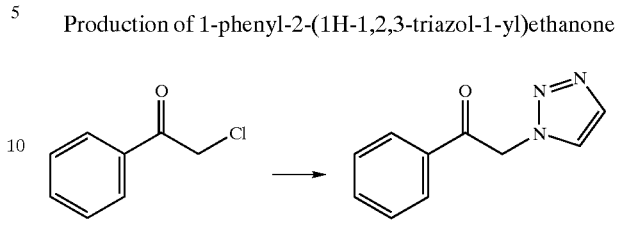

1,2,3-Triazole (1689 mg, 24.45 mmol), sodium iodide (2443 mg, 16.3 mmol) and sodium hydroxide (978 mg, 24.45 mmol) were added to t-amyl alcohol (6.5 ml), and the mixture was refluxed under stirring for 1 hour. 2-Chloro-1-phenylethanone (2520 mg, 16.3 mmol) was dissolved in t-amyl alcohol (13 ml) and added dropwise over 1 hour. The mixture was refluxed under stirring for 1 hour. The mixture was cooled to room temperature, toluene (50 ml) was added. The mixture was washed with water (50 ml×2), dried over anhydrous sodium sulfate and concentrated under reduced pressure. The residue was purified by silica gel column chromatography (hexane/ethyl acetate=3/2→1/4) to give 1-phenyl-2-(1H-1,2,3-triazol-1-yl)ethanone (1.38 g) as brown crystals (yield 45%). 1-Phenyl-2-(2H-1,2,3-triazol-2-yl)ethanone (550 mg) was obtained as yellow crystals (yield 18%). 1-phenyl-2-(1H-1,2,3-triazol-1-yl)ethanone $^1$H-NMR (CDCl$_3$, δ, 300 MHz) 5.91(2H,s), 7.52–7.58 (2H,m), 7.65–7.69(1H,m), 7.74(1H,d,J=0.95 Hz), 7.80(1H, d,J=0.95 Hz), 7.99–8.03(2H,m). 1-phenyl-2-(2H-1,2,3-triazol-2-yl)ethanone $^1$H-NMR (CDCl$_3$, δ, 300 MHz) 5.92(2H,s), 7.49–7.55 (2H,m), 7.62–7.66(1H,m), 7.74(2H,s), 7.95–7.99(2H,m).

EXAMPLE 16

Production of 1-benzyl-1H-1,2,3-triazole

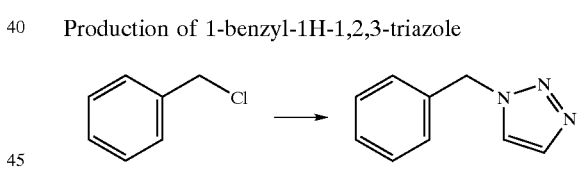

1,2,3-Triazole (1523 mg, 22.05 mmol), sodium iodide (2203 mg, 14.7 mmol) and sodium hydroxide (882 mg, 22.05 mmol) were added to t-amyl alcohol (5.8 ml), and the mixture was refluxed under stirring for 1 hour. Benzyl chloride (1861 mg, 14.7 mmol) was dissolved in t-amyl alcohol (5.8 ml) and added dropwise under reflux over 1 hour. The mixture was refluxed under stirring for 1 hour. The mixture was cooled to room temperature and toluene (50 ml) was added. The mixture was washed with water (50×2), dried over anhydrous sodium sulfate and concentrated under reduced pressure. The residue was purified by silica gel column chromatography (hexane/ethyl acetate=3/1→1/3) to give 1-benzyl-1H-1,2,3-triazole (2.10 g) as white crystals, yield 90%, and 2-benzyl-2H-1,2,3-triazole (140 mg) as white crystals (yield 6%). 1-benzyl-1H-1,2,3-triazole $^1$H-NMR (CDCl$_3$, δ, 300 MHz) 5.56(2H,s), 7.24–7.28 (2H, m), 7.33–7.40(3H,m), 7.47(1H,s),7.70(1H,s). 2-benzyl-2H-1,2,3-triazole $^1$H-NMR (CDCl$_3$, δ, 300 MHz) 5.61(2H,s), 7.26–7.35 (5H, m), 7.63(2H,s).

EXAMPLE 17

Production of 1-(1-naphthylmethyl)-1H-1,2,3-triazole

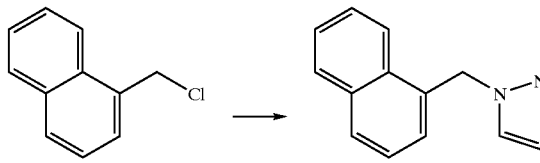

1,2,3-Triazole (1454 mg, 21.05 mmol), sodium iodide (2103 mg, 14.03 mmol) and sodium hydroxide (842 mg, 21.05 mmol) were added to t-amyl alcohol (5.5 ml), and the mixture was refluxed under stirring for 1 hour. 1-(Chloromethyl)naphthalene (2478 mg, 14.03 mmol) was dissolved in t-amyl alcohol (5.5 ml) and added dropwise under reflux over 1 hour. The mixture was refluxed under stirring for 1 hour. The mixture was cooled to room temperature and toluene (50 ml) was added. The mixture was washed with water (50 ml×2), dried over anhydrous sodium sulfate and concentrated under reduced pressure. The residue was purified by silica gel column chromatography (hexane/ethyl acetate=2/1→1/3) to give 1-(1-naphthylmethyl)-1H-1,2,3-triazole (2.47 g) as white crystals (yield 84%), and 2-(1-naphthylmethyl)-2H-1,2,3-triazole as a colorless oil (136 mg, yield 5%). 1-(1-naphthylmethyl)-1H-1,2,3-triazole $^1$H-NMR (CDCl$_3$, δ, 300 MHz) 6.02(2H,s), 7.33(1H,s), 7.41–7.55(4H,m), 7.64(1H,s), 7.89–7.97(3H,m). 2-(1-naphthylmethyl)-2H-1,2,3-triazole $^1$H-NMR (CDCl$_3$, δ, 300 MHz) 6.06(2H,s),7.41–7.57(4H, m), 7.62(2H,s), 7.84–7.89(2H,m), 8.15(1H,d,J=7.96 Hz).

Reference Example 11

Production of 2,2-dichloroacetaldehyde tosylhydrazone

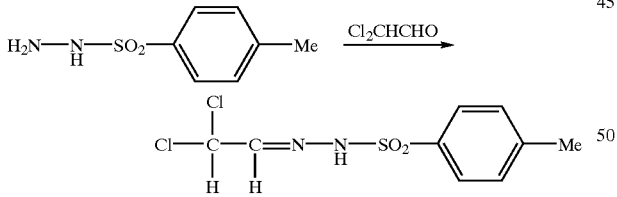

Tosylhydrazine (234 g, 1.26 mol) was suspended in propionic acid (2 L) and dichloroacetaldehyde (142 g, 1.26 mol) was added at 15–20° C. The mixture was stirred at room temperature for 2 hours and under ice-cooling for 3 hours. The precipitated crystals were collected by filtration and washed with toluene. The crystals were dried under reduced pressure to give 2,2-dichloroacetaldehyde tosylhydrazone (247 g, yield 70%).

$^1$H-NMR (CDCl$_3$, δ, 300 MHz) 2.47(3H,s), 6.12(1H,d,J= 7.4 Hz), 7.21(1H,d,J=7.4 Hz), 7.34–7.38(2H,m), 7.80–7.84 (2H,m), 8.06(1H,s).

Reference Example 12

Production of 1-[4-(4-methoxyphenyl)butan-1-yl]-1H-1,2,3-triazole

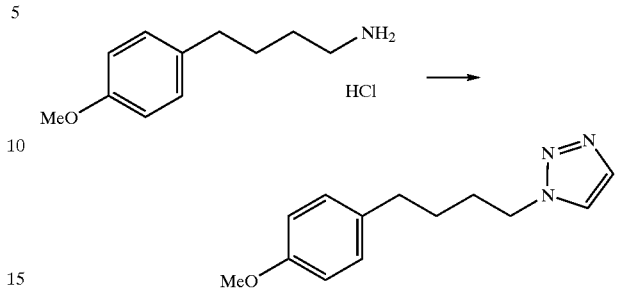

1-(4-Aminobutyl)-4-methoxybenzene hydrochloride (1.0 g, 4.64 mmol) was dissolved in water. Toluene and 2N-sodium hydroxide (10 ml) were added and the mixture was partitioned. The mixture was washed with 20% brine, dried over anhydrous sodium sulfate and concentrated under reduced pressure. The residue was dissolved in methanol (8 ml) and the suspension of 2,2-dichloroacetaldehyde tosylhydrazone (2.61 g, 9.28 mmol) in methanol (12 ml) was added dropwise at 15–20° C., and the mixture was stirred at room temperature for 2 hours. Methanol was added and, after making the mixture homogeneous, it was quantitatively measured by HPLC. As a result, 1-[4-(4-methoxyphenyl) butan-1-yl]-1H-1,2,3-triazole (270 mg) was found to be present.

yield (quantitatively measured) 25%.

EXAMPLE 18

Production of 4-amino-4'-methoxybutyrophenone trifluoromethanesulfonate

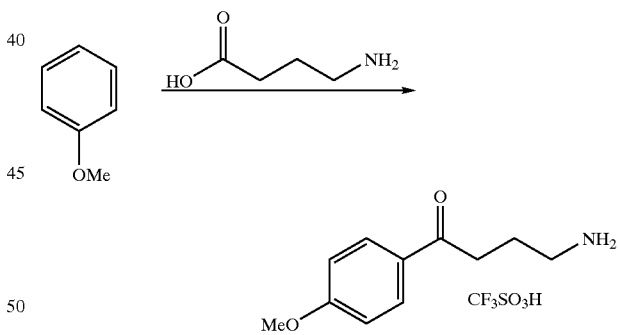

Trifluoromethanesulfonic acid (4 ml) was ice-cooled, and 4-aminobutyric acid (1093 mg, 10.6 mmol) was added. Then, anisole (1 ml, 9.25 mmol) was added. The mixture was heated and stirred at 80° C. for 50 min. The mixture was cooled to room temperature and added dropwise to water (17 ml) under ice-cooling. The mixture was stirred under ice-cooling for 20 min and then at −10° C. for 30 min. The crystals were filtrated, washed with ice-cooled saturated brine, and dried under reduced pressure to give 4-amino-4'-methoxybutyrophenone trifluoromethanesulfonate (2.47 g, yield 78%).

$^1$H-NMR (D$_2$O, δ, 300 MHz) 1.88–1.99(2H,m), 2.98(2H, t,J=7.5 Hz), 3.09(2H,t,J=7.1 Hz), 3.80(3H,s), 6.95–6.99(2H, m), 7.86–7.91(2H,m).

EXAMPLE 19

Production of 1-(4-aminobutyl)-4-methoxybenzene hydrochloride

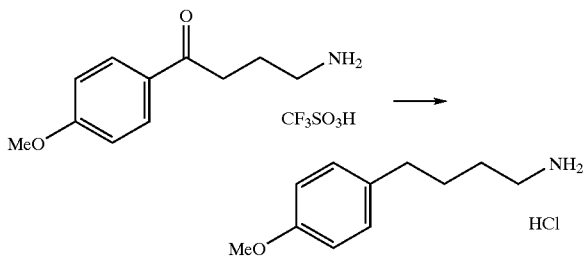

4-Amino-4'-methoxybutyrophenone trifluoromethanesulfonate (60 g, 174.8 mmol) was dissolved in tetrahydrofuran/water-1/1 (600 ml) and 10% palladium carbon (water-containing product, 6 g) was added. The mixture was subjected to catalytic reduction at 50° C. for 7 hours under hydrogen pressure (0.8 Mpa). The catalyst was filtered off and toluene (360 ml) and 2N-potassium hydroxide (180 ml) were added. The mixture was partitioned and the aqueous layer was extracted with toluene (360 ml). The organic layers were combined and washed with 20% brine (3 times). To the residue obtained by concentration under reduced pressure was added 2-propanol (300 ml) and con. hydrochloric acid (34 ml) was added dropwise under ice-cooling. To the residue obtained by concentration under reduced pressure was added 2-propanol (300 ml) and the mixture was concentrated under reduced pressure. 2-Propanol (300 ml) was added and the mixture was concentrated under reduced pressure. To the obtained residue was added isopropyl ether (200 ml) and the mixture was stirred at room temperature for 10 min. The precipitated crystals were collected by filtration and dried under reduced pressure to give 1-(4-aminobutyl)-4-methoxybenzene hydrochloride (32.1 g, yield 85%).

$^1$H-NMR (D$_2$O, δ, 300 MHz) 1.54–1.57(4H,m), 2.52(2H, t,J=6.5 Hz), 2.89(2H,t,J=6.8 Hz), 3.71(3H,s), 6.85–6.88(2H, m), 7.12–7.15(2H,m).

EXAMPLE 20

Production of 1-[4-(4-methoxyphenyl)butan-1-yl]-1H-1,2,3-triazole

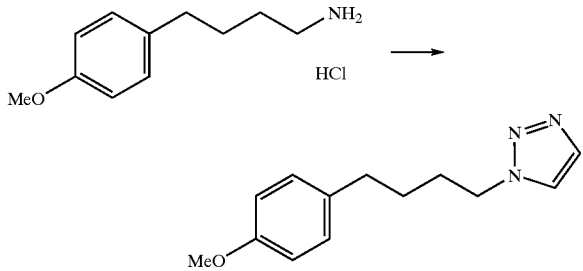

1-(4-Aminobutyl)-4-methoxybenzene hydrochloride (1.0 g, 4.64 mmol) was dissolved in water. Toluene (10 ml) and 2N-sodium hydroxide (10 ml) were added and the mixture was partitioned. The organic layer was washed with 20% brine, dried over anhydrous sodium sulfate and concentrated under reduced pressure. The residue was dissolved in methanol (8 ml), and a suspension of 2,2-dichloroacetaldehyde tosylhydrazone (2.61 g, 9.28 mmol) in methanol (12 ml) was added dropwise at 15–20° C. The mixture was stirred at room temperature for 2 hours and concentrated under reduced pressure. To the residue was added ethyl acetate (50 ml) and then was added saturated aqueous sodium hydrogen carbonate (50 ml). The mixture was stirred for 10 min and partitioned, which was followed by washing with saturated brine and concentration under reduced pressure. Purification by silica gel column gave 1-[4-(4-methoxyphenyl)butan-1-yl]-1H-1,2,3-triazole (1.1 g, yield 100%).

$^1$H-NMR (CDCl$_3$, δ, 300 MHz) 1.57–1.66(2H,m), 1.86–1.97(2H,m) 2.58(2H,t,J=7.5 Hz), 3.79(3H,s), 4.37(2H, t,J=7.1 Hz), 6.78–6.83(2H,m), 7.01–7.06(2H,m), 7.48(1H, d,J=0.8 Hz), 7.67(1H,d,J=0.8 Hz).

EXAMPLE 21

Production of 1-[4-(4-methoxyphenyl)butan-1-yl]-1H-1,2,3-triazole

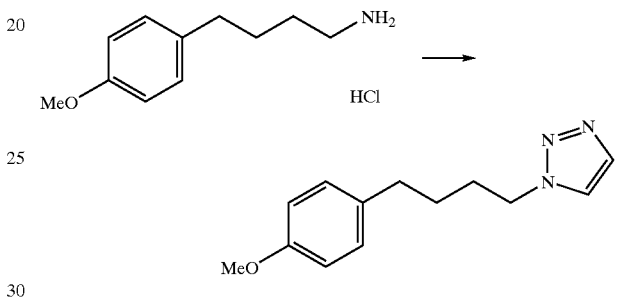

1-(4-Aminobutyl)-4-methoxybenzene hydrochloride (1.0 g, 4.64 mmol) was dissolved in water. Toluene (10 ml) and 2N-sodium hydroxide (10 ml) were added and the mixture was partitioned. The organic layer was washed with 20% brine, dried over anhydrous sodium sulfate and concentrated under reduced pressure. The residue was dissolved in methanol (8 ml) and a suspension of 2,2-dichloroacetaldehyde tosylhydrazone (2.61 g, 9.28 mmol) in methanol (12 ml) was added dropwise at 15–20° C. The mixture was stirred at room temperature for 2 hours and concentrated under reduced pressure. To the residue was added toluene (50 ml) and 2N-sodium hydroxide (50 ml) was added with stirring. The mixture was partitioned 10 min later and quantitatively measured by HPLC. As a result, 1-[4-(4-methoxyphenyl)butan-1-yl]-1H-1,2,3-triazole (417 mg) was found to be present. yield (quantitatively measured) 39%.

EXAMPLE 22

Production of 1-[4-(4-methoxyphenyl)butan-1-yl]-1H-1,2,3-triazole

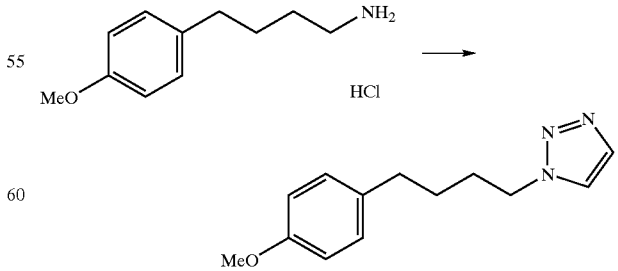

1-(4-Aminobutyl)-4-methoxybenzene hydrochloride (1.0 g, 4.64 mmol) was dissolved in water. Toluene (10 ml) and 2N-sodium hydroxide (10 ml) were added and the mixture was partitioned. The organic layer was washed with 20% brine, dried over anhydrous sodium sulfate and concentrated under reduced pressure. The residue was dissolved in methanol (8 ml), and a suspension of 2,2-dichloroacetaldehyde tosylhydrazone (2.61 g, 9.28 mmol) in methanol (12 ml) was added dropwise at 15–20° C. After stirring at room temperature for 2 hours, the mixture was concentrated under reduced pressure. To the residue was added toluene (50 ml), and 25% aqueous ammonia (50 ml) was added while stirring the mixture. The mixture was partitioned 10 min later and quantitatively measured by HPLC. As a result, 1-[4-(4-methoxyphenyl)butan-1-yl]-1H-1,2,3-triazole (829 mg) was found to be present. yield (quantitatively measured) 77%.

EXAMPLE 23

1-[4-(4-Methoxyphenyl)butan-1-yl]-1H-1,2,3-triazole methanesulfonate

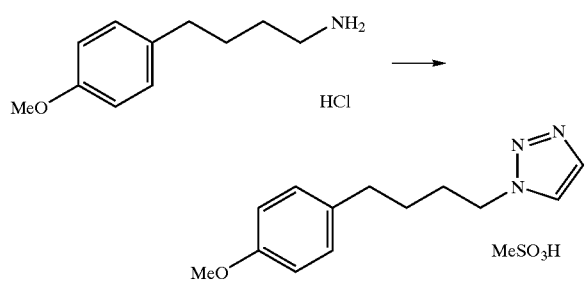

1-(4-Aminobutyl)-4-methoxybenzene hydrochloride (2.0 g, 9.27 mmol) was dissolved in water (10 ml). Toluene (20 ml) and 2N-sodium hydroxide (10 ml) were added and the mixture was partitioned. The organic layer was washed with 20% brine (10 ml) twice, dried over anhydrous sodium sulfate and concentrated under reduced pressure. To the residue was added methanol (5 ml) and the mixture was concentrated under reduced pressure. The residue was dissolved in methanol (10 ml). This methanol solution was added dropwise to a suspension of 2,2-dichloroacetaldehyde tosylhydrazone (5213 mg, 18.54 mmol) in methanol (30 ml) at 20–25° C. The mixture was stirred at room temperature for 1 hour 20 min. To the mixture of toluene (20 ml) and saturated aqueous sodium hydrogen carbonate (60 ml) was added this reaction mixture, and the mixture was stirred at room temperature for 50 min. The organic solvent was evaporated under reduced pressure and the residue was extracted with toluene (40 ml). 4N-Sodium hydroxide (30 ml) was added, and the mixture was heated to 50–60° C. and partitioned. Water (30 ml) was added, and the mixture was heated to 50–60° C. and partitioned. Water (30 ml) was added, and the mixture was heated to 50–60° C. and partitioned. The organic layer was washed with a mixture of 20% citric acid (15 ml) and saturated brine (15 ml). After washing with saturated aqueous sodium hydrogen carbonate (30 ml), it was washed with water (30 ml) and concentrated under reduced pressure. The residue was dissolved in ethyl acetate (10 ml) and methanesulfonic acid (0.49 ml, 7.55 mmol) was added under ice-cooling. Ethyl acetate (2 ml) was added and the mixture was stirred under ice-cooling for 50 min. The precipitated crystals were collected by filtration, washed with ice-cooled ethyl acetate (8 ml) and dried under reduced pressure to give 1-[4-(4-methoxyphenyl)butan-1-yl]-1H-1,2,3-triazole methanesulfonate (2.19 g, yield 72%).

$^1$H-NMR (DMSO-$d_6$, δ, 300 MHz) 1.40–1.51(2H,m), 1.74–1.84(2H,m) 2.39(3H,s), 2.51(2H,t,J=7.7 Hz), 3.69(3H, s), 4.38(2H,t,J=7.0 Hz), 6.79–6.84(2H,m), 7.04–7.09(2H, m), 7.71(1H,d,J=0.7 Hz), 8.11(1H,d,J=0.7 Hz).

EXAMPLE 24

1-[4-(4-Methoxyphenyl)butan-1-yl]-1H-1,2,3-triazole hydrochloride

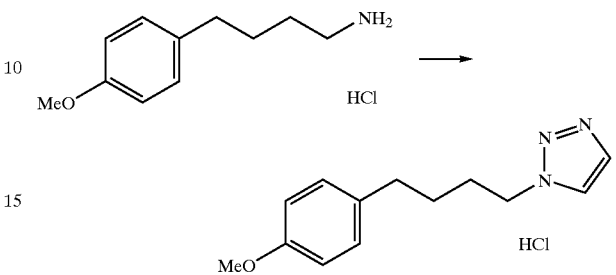

1-(4-Aminobutyl)-4-methoxybenzene hydrochloride (2.0 g, 9.27 mmol) was dissolved in water (10 ml). Toluene (20 ml) and 2N-sodium hydroxide (10 ml) were added and the mixture was partitioned. The mixture was washed 20% brine (10 ml) twice, dried over anhydrous sodium sulfate and concentrated under reduced pressure. Methanol (5 ml) was added and the mixture was concentrated under reduced pressure. The residue was dissolved in methanol (10 ml). This methanol solution was added dropwise to a slurry of 2,2-dichloroacetaldehyde tosylhydrazone (5213 mg, 18.54 mmol) in methanol (30 ml) at 20–25° C. and the mixture was stirred at room temperature for 3 hours. The reaction mixture was poured into a mixture of toluene (19 ml) and saturated aqueous sodium hydrogen carbonate (57 ml) and the mixture was stirred at room temperature for 50 min. The organic solvent was evaporated by concentration under reduced pressure and the residue was extracted with toluene (40 ml). 4N-Sodium hydroxide (30 ml) was added, and the mixture was heated to 50–60° C. and partitioned. Water (30 ml) was added, and the mixture was heated to 50–60° C. and partitioned. Water (30 ml) was added, and the mixture was heated to 50–60° C. and partitioned. The organic layer was washed with 20% citric acid (15 ml), and then 3 times with water (20 ml), with saturated aqueous sodium hydrogen carbonate (30 ml) and with water (30 ml), and concentrated under reduced pressure. The residue was dissolved in ethanol (10 ml) and concentrated hydrochloric acid (2.5 ml) was added. The mixture was concentrated under reduced pressure and 2-propanol was added, and the mixture was concentrated under reduced pressure. Ethyl acetate was added, and the mixture was concentrated under reduced pressure. Ethyl acetate (10 ml) was added and triturated. The mixture was stirred at room temperature for 40 min. The precipitated crystals were collected by filtration and dried under reduced pressure to give 1-[4-(4-methoxyphenyl)butan-1-yl]-1H-1,2,3-triazole hydrochloride (1.61 g, yield 68%).

$^1$H-NMR (DMSO-$d_6$, δ, 300 MHz) 1.39–1.50(2H,m), 1.73–1.83(2H,m), 2.49(2H,t,J=7.6 Hz), 3.68(3H,s), 4.37 (2H,t,J=7.0 Hz), 6.77–6.83(2H,m), 7.02–7.07(2H,m), 7.73 (1H,d,J=0.7 Hz), 8.13(1H,d,J=0.7 Hz).

Reference Example 13

Production of 4-[4-(1H-1,2,3-triazol-1-yl)butyl]phenol

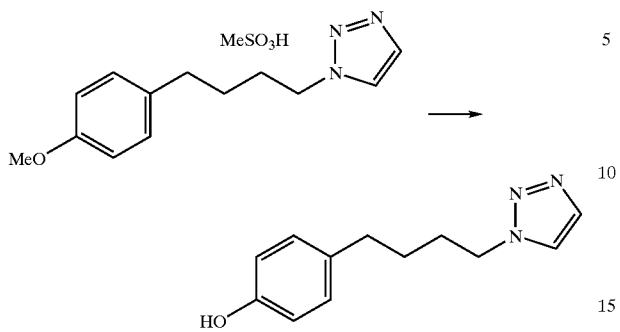

1-[4-(4-Methoxyphenyl)butan-1-yl]-1H-1,2,3-triazole methanesulfonate (4.0 g, 12.22 mmol) was added to 48% hydrobromic acid (8 ml) and the mixture was heated at 80–90° C. for 6 hours. The mixture was ice-cooled, and after dropwise addition of 4N-sodium hydroxide (32 ml), washed with toluene. 6N Hydrochloric acid was added to the aqueous layer to make pH 6.3. The mixture was extracted with ethyl acetate (30 ml) and tetrahydrofuran (15 ml) and washed with water. Active charcoal (200 mg) was added, and the mixture was stirred at room temperature for 10 min. The mixture was filtrated and concentrated under reduced pressure. Ethyl acetate (10 ml) was added to the residue, and the mixture was refluxed. The mixture was allowed to cool and stirred for 30 min, and hexane (10 ml) was added. The mixture was stirred at room temperature for 30 min. The precipitated crystals were collected by filtration and dried under reduced pressure to give $^4$-[4-(1H-1,2,3-triazol-1-yl)butyl]phenol (2.25 g, yield 85%).

1H-NMR (CDCl$_3$-DMSO-d$_6$, δ, 300 MHz) 1.48–1.59 (2H,m), 1.80–1.91(2H,m), 2.49(2H,t,J=7.5 Hz), 4.31(2H,t, J=7.2 Hz), 6.68–6.73(2H,m), 6.87–6.91(2H,m), 7.45(1H,d, J=0.7 Hz), 7.61(1H,d,J=0.7 Hz), 8.12(1H,s).

Reference Example 14

Production of 4-(trifluoromethyl)cinnamamide

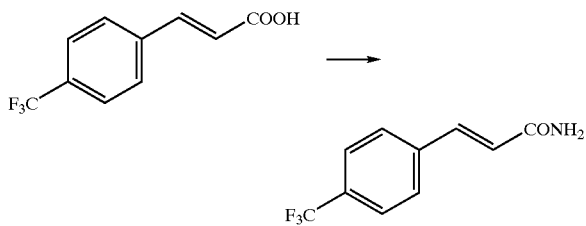

4-(Trifluoromethyl)cinnamic acid (64.85 g, 300 mmol) was added in toluene (325 ml) and dimethylformamide (2.2 ml). Thionyl chloride (26.3 ml, 361 mmol) was added dropwise at room temperature, and the mixture was heated at 45° C. for 2 hours. The obtained reaction mixture was added dropwise to 25% aqueous ammonia (325 ml) while keeping the mixture at 5–20° C. The mixture was stirred at room temperature for 1 hour. The precipitated crystals were collected by filtration, washed with 20 water and isopropyl ether and dried under reduced pressure to give 4-(trifluoromethyl)cinnamamide (60.76 g, yield 94%).

$^1$H-NMR (CDCl$_3$-DMSO-d$_6$, δ, 300 MHz) 5.93(1H,s), 6.53(1H,d,J=15.8 Hz), 6.75(1H,s), 7.48–7.53(5H,m).

Reference Example 15

Production of 4-(chloromethyl)-2-[(E)-2-[4-(trifluoromethyl)-phenyl]ethenyl]-1,3-oxazole

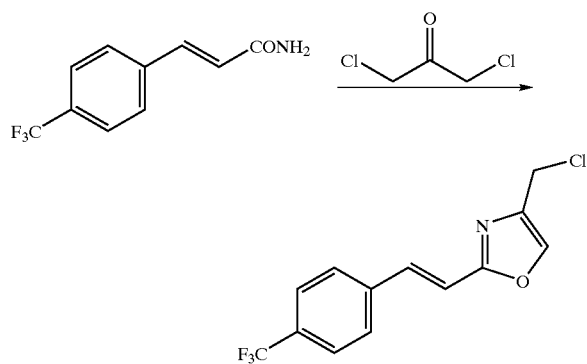

4-(Trifluoromethyl)cinnamamide (1 g, 4.65 mmol) and 1,3-dichloroacetone (1.1 g, 8.66 mmol) were added to toluene (5 ml) and the mixture was refluxed under heating for 8 hours. Ethyl acetate (20 ml) was added, and the mixture was washed with water (20 ml) twice and concentrated under reduced pressure. To the residue was added methanol (4 ml) and the mixture was stirred at room temperature. The crystals were filtrated and dried under reduced pressure to give 4-(chloromethyl)-2-[(E)-2-[4-(trifluoromethyl)phenyl] ethenyl]-1,3-oxazole (733 mg, yield 55%).

$^1$H-NMR (CDCl$_3$, δ, 300 MHz) 4.56(2H,s), 7.01(1H,d,J= 16.4 Hz), 7.54–7.68(6H,m).

Reference Example 16

Production of 1-[4-[4-[[2-[(E)-2-[4-(trifluoromethyl) phenyl]ethenyl]-1,3-oxazol-4-yl]methoxy]phenyl]butyl]-1H-1,2,3-triazole

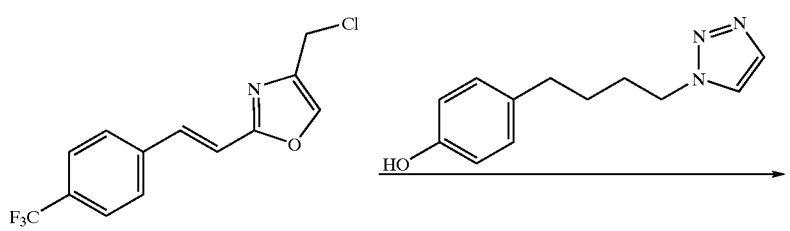

-continued

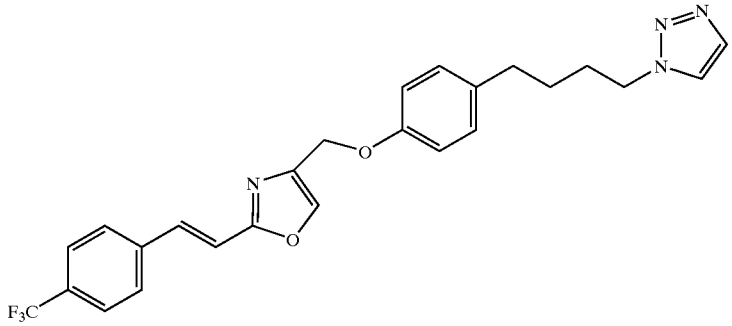

4-[4-(1H-1,2,3-Triazol-1-yl)butyl]phenol (400 mg, 1.84 mmol) and 4-(chloromethyl)-2-[(E)-2-[4-(trifluoromethyl) phenyl]ethenyl]-1,3-oxazole (529 mg, 1.84 mmol) were dissolved in dimethylformamide (3 ml), potassium carbonate (279 mg, 2.02 mmol) was added and the mixture was stirred at 65–75° C. for 4 hours. 4-[4-(1H-1,2,3-Triazol-1-yl)butyl]phenol (40 mg, 0.184 mmol) was added and the mixture was stirred at 65–75° C. for 3 more hours. After cooling to room temperature, water (5 ml) and methanol (3 ml) were added in this order, and the mixture was stirred at room temperature for 40 min. The precipitated crystals were collected by filtration, washed with water and dried under reduced pressure to give 1-[4-[4-[[2-[(E)-2-[-4-(trifiuoromethyl)phenyl]ethenyl]-1,3-oxazol-4-yl]methoxy]phenyl]butyl]-1H-1,2,3-triazole (799 mg, yield 93%).

$^1$H-NMR (CDCl$_3$, δ, 300 MHz) 1.57–1.68(2H,m), 1.88–1.99(2H,m), 2.60(2H,t,J=7.5 Hz), 4.39(2H,t,J=7.1 Hz), 5.01(2H,s), 6.89–7.08(5H,m), 7.49–7.70(8H,m).

Reference Example 17

(E)-3-(4-(Trifluoromethyl)phenyl)-2-propenamide

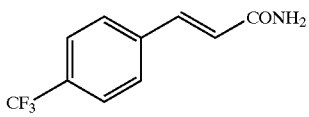

(E)-3-(4-(Trifluoromethyl)phenyl)-2-propenoic acid (2400 g, 11.1 mol) and DMF (N,N-dimethylformamide)(82 ml) were added to toluene (12 L). SOCl$_2$ (52.6 mL, 721 mmol) was added dropwise at room temperature and the mixture was stirred at 45–50° C. for 1 hour. The toluene solution cooled to room temperature was added dropwise to 25% aqueous ammonia (12L) at 5–25° C. The mixture was stirred at 45–55° C. for 1 hour. After allowing to cool to room temperature and stirring, the mixture was stirred at the same temperature for 1 hour. The precipitated crystals were collected by filtration, washed with water (12 L) and dried under reduced pressure to give (E)-3-(4-(trifluoromethyl) phenyl)-2-propenamide (2293 g, 10.7 mol, yield 96%).

$^1$H-NMR (DMSO-d$_6$, δ, 300 MHz) 6.72(1H,d,J=16.1 Hz), 7.20(1H,s), 7.46(1H,d,J=15.9 Hz), 7.62(1H,s), 7.67–7.83 (4H,m).

EXAMPLE 25

4-(Acetoxymethyl)-2-[(E)-2-[4-(trifluoromethyl)phenyl]-ethenyl]-1,3-oxazole

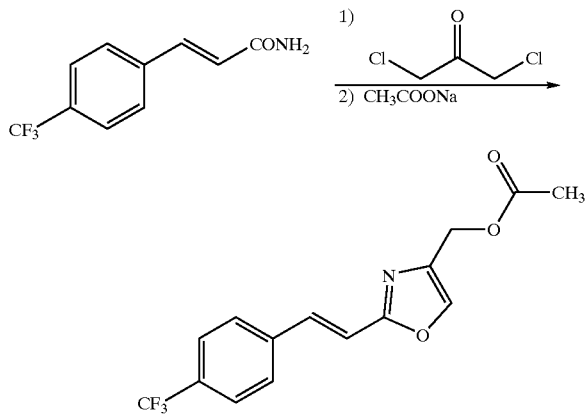

(E)-3-(4-(Trifluoromethyl)phenyl)-2-propenamide (10.0 g, 46.5 mmol) and 1,3-dichloroacetone (11.0 g, 86.6 mmol) were added to toluene (50 ml), and the mixture was subjected to refluxing azeotropic dehydration using a Dean-Stark tube for 8.5 hours. The reaction mixture was concentrated under reduced pressure. To the residue were added dimethyl sulfoxide (50 ml) and sodium acetate trihydrate (15.8 g, 116.1 mmol). The mixture was stirred at 70–75° C. for 4 hours. Methanol (50 ml) was added. After allowing-to cool to room temperature and stirring; the mixture was stirred under ice-cooling for 1 hour. The precipitated crystals were collected by filtration, washed with cold-methanol (30 ml) and dried under reduced pressure to give 4-(acetoxymethyl)-2-[(E)-2-[4-(trifluoromethyl)phenyl] ethenyl]-1,3-oxazole (13.1 g, yield 65%).

$^1$H-NMR (CDCl$_3$, δ, 300 MHz) 2.11(3H,s), 5.13(2H,s), 7.00(1H,d,J=16.4 Hz), 7.55(1H,d,J=16.4 Hz), 7.58–7.62 (5H,m).

EXAMPLE 26
4-(Acetoxymethyl)-2-[(E)-2-[4-(trifluoromethyl)phenyl]ethenyl]-1,3-oxazole

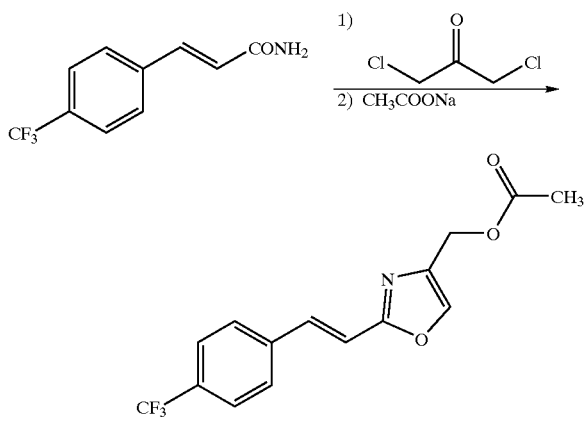

(E)-3-(4-(Trifluoromethyl)phenyl)-2-propenamide (950 g, 4.42 mol) and 1,3-dichloroacetone (1045 g, 8.23 mol) were added to toluene (4.75 L) and the mixture was subjected to refluxing azeotropic dehydration using a Dean-Stark tube for 8 hours. During the reaction, an azeotropic mixture (2.38 L) was removed. The reaction mixture was concentrated under reduced pressure, and dimethyl sulfoxide (4.75L) and sodium acetate (905 g, 11.0 mol) were added to the residue. The mixture was stirred at 70–80° C. for 3.5 hours. Methanol (4.75 L) was added. After allowing to cool to room temperature and stirring, the mixture was stirred for 1 hour under ice-cooling. The precipitated crystals were collected by filtration, washed with cold-methanol (1.9 L), and dried under reduced pressure to give 4-(acetoxymethyl)-2-[(E)-2-[4-(trifluoromethyl)phenyl]ethenyl]-1,3-oxazole (1560 g, yield 51%).

EXAMPLE 27
1-[4-[4-[[2-[(E)-2-[4-(trifluoromethyl)phenyl]ethenyl]-1,3-oxazol-4-yl]methoxy]phenyl]butyl]-1H-1,2,3-triazole

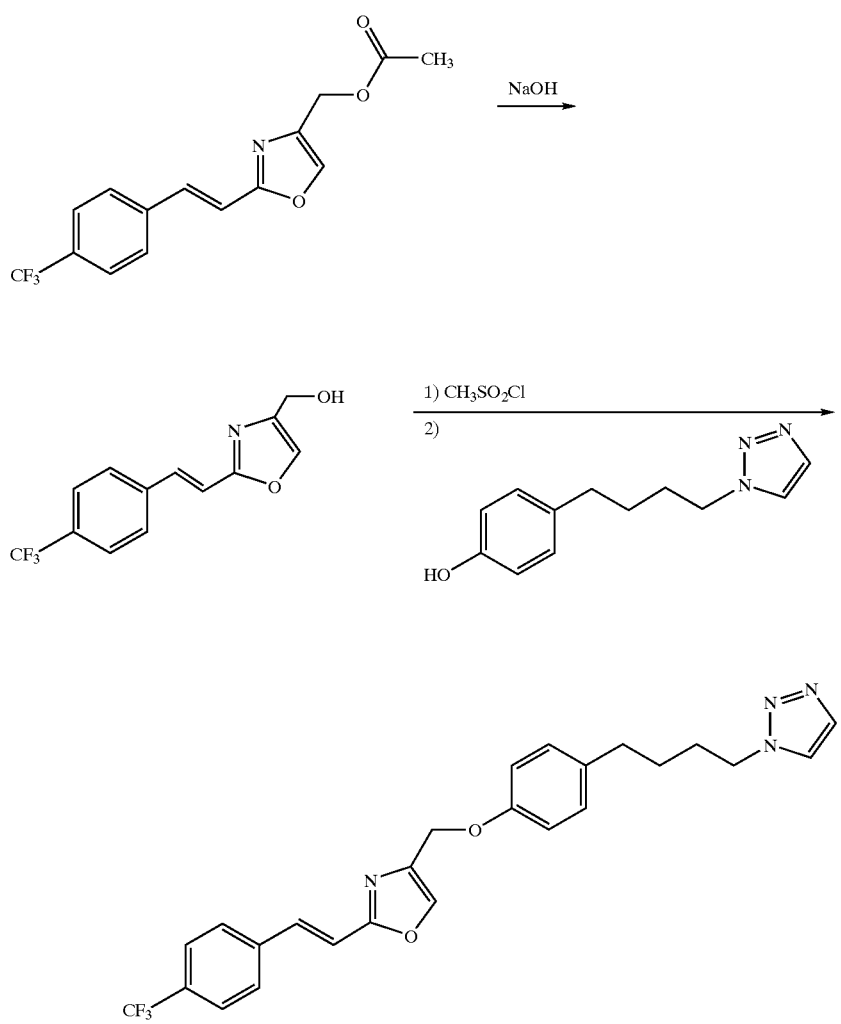

4-(Acetoxymethyl)-2-[(E)-2-[4-(trifluoromethyl)phenyl] ethenyl]-1,3-oxazole (20.0 g, 64.3 mmol) was dissolved in dimethyl sulfoxide (200 ml), and 2N-aqueous sodium hydroxide solution (35 mL 70.0 mmol) was added at 50° C. The mixture was stirred at about 40° C. for 15 min. Water (200 ml) was added at the same temperature. After allowing to cool to room temperature and stirring, the mixture was stirred at the same temperature for 1 hour. The precipitated crystals were collected by filtration, washed with water (60 ml) and dried under reduced pressure to give 4-(hydroxymethyl)-2-[(E)-2-[4-(trifluoromethyl)phenyl] ethenyl]-1,3-oxazole (16.4 g, 61.1 mmol, yield 95%).

1-[4-[4-[[2-[(E)-2-[4-(trifluoromethyl)phenyl]ethenyl]-1,3-oxazol-4-yl]methoxy]phenyl]butyl]-1H-1,2,3-triazole (1.61 g, 3.44 mmol, yield 88%).

$^{1}$H-NMR (CDCl$_{3}$, δ, 300 MHz) 1.57–1.68(2H,m), 1.88–1.99(2H,m) 2.60(2H,t,J=7.5 Hz), 4.39(2H,t,J=7.1 Hz), 5.01(2H,s), 6.89–7.08(5H,m), 7.49–7.70(8H,m).

EXAMPLE 28

1-[4-[4-[[2-[(E)-2-[4-(trifluoromethyl)phenyl]ethenyl]-1,3-oxazol-4-yl]methoxy]phenyl]butyl]-1H-1,2,3-triazole

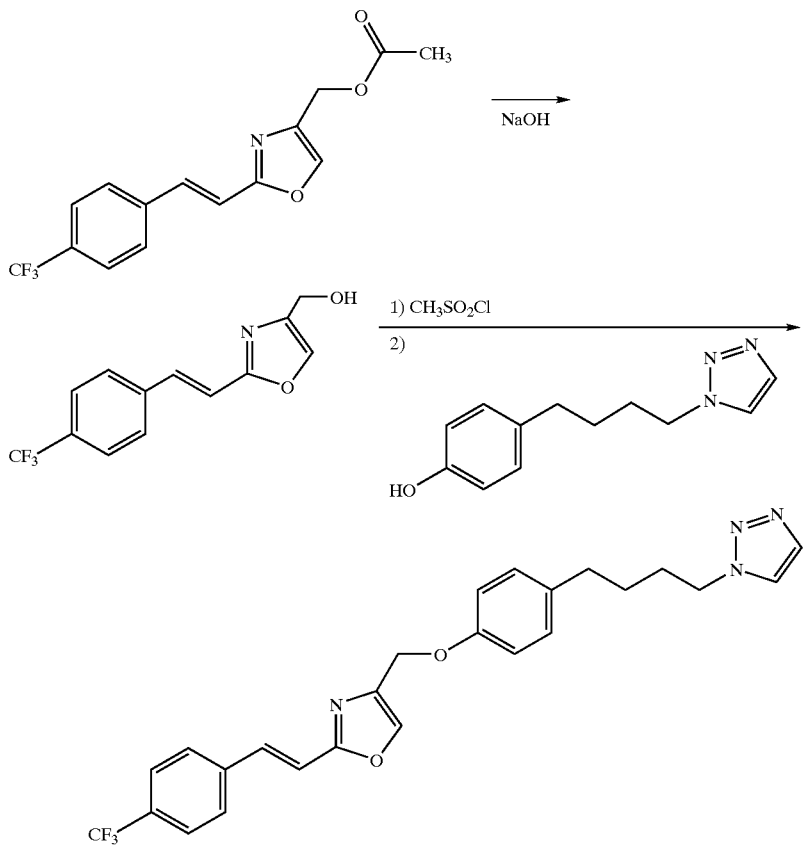

The obtained 4-(hydroxymethyl)-2-[(E)-2-[4-(trifluoromethyl)phenyl]ethenyl]-1,3-oxazole (1.00 g, 3.71 mmol) and diisopropylethylamine (0.95 mL, 5.44 mmol) were added to THF (tetrahydrofuran) (15 ml). Methanesulfonyl chloride (0.45 mL, 5.81 mmol) was added dropwise under ice-cooling. The mixture was stirred at the same temperature for 1 hour. 4-[4-(1H-1,2,3-Triazol-1-yl)butyl] phenol (900 mg, 4.14 mmol) and tetra(n-butyl)ammonium bromide (60 mg, 0.19 mmol) were added at the same temperature. A 2N aquous sodium hydroxide solution (7.5 mL, 15.0 mmol) was added dropwise at not more than 15° C. and the mixture was stirred with reflux for 1 hour. After allowing to cool to room temperature and stirring, the organic layer was concentrated under reduced pressure. Ethanol (20 ml) was added to the residue, and the mixture was stirred with reflux. Water (20 ml) was added dropwise at the same temperature. After allowing to cool to room temperature and stirring, the mixture was ice-cooled. The precipitated crystals were collected by filtration, washed with water (20 ml) and dried under reduced pressure to give 4-(Acetoxymethyl)-2-[(E)-2-[4-(trifluoromethyl)phenyl]-ethenyl]-1,3-oxazole (1556 g, 2.23 mol), 2N-aqueous sodium hydroxide solution (2.4 L, 4.8 mol) and activated carbon (47 g) were added to methanol (4.7 L), and the mixture was refluxed under stirring for 1 hour. The activated carbon and the insoluble material were removed by filtration under pressurization. The residue was washed with methanol/water (2:1) (470 ml). The washing solution was combined with the filtrate and the mixture was refluxed. Water (3.3 L) was added at the same temperature. After allowing to cool to room temperature and stirring, the mixture was stirred at the same temperature for 1 hour. The precipitated crystals were collected by filtration, washed with water (4.7 L) and dried under reduced pressure to give 4-(hydroxymethyl)-2-[(E)-2-[4-(trifluoromethyl)phenyl] ethenyl]-1,3-oxazole (568.5 g, 2.11 mol, yield 95%).

The obtained 4-(hydroxymethyl)-2-[(E)-2-[4-(trifluoromethyl)phenyl]ethenyl]-1,3-oxazole (567 g, 2.11 mol) and diisopropylethylamine (340 g, 2.63 mol) were added to THF (3.4 L). A solution of methanesulfonyl chloride (302 g, 2.63 mol) in THF (567 ml) was added dropwise under ice-cooling. The mixture was stirred at the same temperature for 1 hour and diisopropylethylamine (27.3 g, 0.21 mol), methanesulfonyl chloride (24.2 g, 0.21 mol) and THF (57 ml) solution were added. The mixture was stirred under reflux for 1.5 hours. After allowing to cool to room temperature, 15% aqueous sodium hydroxide (1.96 kg, 7.35 mol) was added dropwise. 4-[4-(1H-1,2,3-Triazol-1-yl)butyl]phenol (503 g, 2.32 mol) and tetra(n-butyl) ammonium bromide (68.0 g, 0.21 mol) were added at the same temperature, and the mixture was refluxed for 4 hours under stirring. Water (3.1 L) and methanol (7.4 L) were added dropwise at the same temperature. After allowing to cool to room temperature, the mixture was stirred at the same temperature for 1 hour. The precipitated crystals were collected by filtration, washed with THF/methanol/water (1:1:2) (2.8 L), water (2.8 L) and cold-methanol (2.8 L) and dried under reduced pressure to give 1-[4-[4-[[2-[(E)-2-[4-(trifluoromethyl)phenyl]ethenyl]-1,3-oxazol-4-yl]methoxy]phenyl]butyl]-1H-1,2,3-triazole (883 g, 1.88 mol, yield 85%).

Reference Example 18

4-(Hydroxymethyl)-2-[(E)-2-[4-(trifluoromethyl)phenyl]ethenyl]-1,3-oxazole

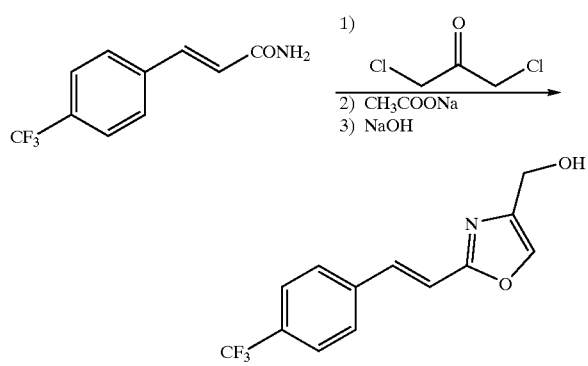

(E)-3-(4-(Trifluoromethyl)phenyl)-2-propenamide (20.0 g, 92.9 mmol) was added to toluene (75 ml), and 1,3-dichloroacetone (22.0 g, 173.3 mmol) and toluene (25 ml) were added. The mixture was subjected to refluxing azeotropic dehydration for 9 hours. The reaction mixture was divided into two equal portions and one of them was concentrated under reduced pressure. To the residue were added dimethyl sulfoxide (100 ml), sodium acetate trihydrate (15.9 g, 116.8 mmol) and water (20 ml). The mixture was stirred at 70–75° C. for 4.5 hours. 2N-Aqueous sodium hydroxide solution (60 ml) was added at the same temperature and the mixture was stirred for 1 hour. After allowing to cool to room temperature, toluene (400 ml) and water (400 ml) were added and the mixture was partitioned. After washing with 5% brine (200 ml), the organic layer was concentrated under reduced pressure. To the residue was added methanol (10 ml) and the mixture was heated to 60° C. to allow dissolution. After allowing to cool to room temperature and stirring, the mixture was stirred for 1 hour under ice-cooling. The precipitated crystals were collected by filtration, washed with cold-methanol (5 ml) and dried under reduced pressure to give 4-(hydroxymethyl)-2-[(E)-2-[4-(trifluoromethyl)phenyl]-ethenyl]-1,3-oxazole (5.96 g, 22.1 mmol, yield 48%).

$^1$H-NMR (CDCl$_3$, δ, 300 MHz) 2.83(1H,s), 4.69(2H,d,J= 5.2 Hz), 6.96(1H,d,J=13.1 Hz), 7.51(1H,d,J=12.7 Hz), 7.55–7.66(5H,m).

Reference Example 19

4-(Hydroxymethyl)-2-[(E)-2-[4-(trifluoromethyl)phenyl]-ethenyl]-1,3-oxazole

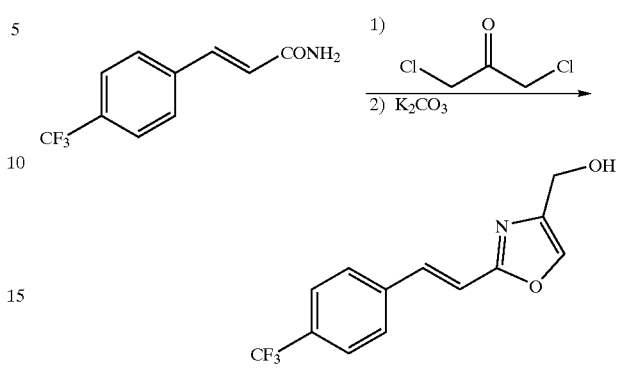

(E)-3-(4-(Trifluoromethyl)phenyl)-2-propenamide (4.30 g, 20.0 mmol) and 1,3-dichloroacetone (4.75 g, 37.4 mmol) were added to toluene (20 ml) and the mixture was subjected to refluxing azeotropic dehydration using a Dean-Stark tube for 6 hours. The reaction mixture was allowed to cool to room temperature, and DMF (50 ml), water (30 ml) and potassium carbonate (13.7 g, 99.1 mmol) were added. The mixture was stirred at 100° C. for 1.5 hours. After allowing to cool to room temperature, ethyl acetate (200 ml) and water (150 ml) were added and the mixture was partitioned. The organic layer was washed with water/saturated brine (1:1, 100 ml). To the organic layer was added ethyl acetate (400 ml), and the mixture was washed with water (200 ml) twice and concentrated under reduced pressure. Ethanol (30 ml) was added to the residue. Water (38 ml) was added and the precipitated crystals were collected by filtration, washed with water (40 ml) and dried under reduced pressure to give 4-(hydroxymethyl)-2-[(E)-2-[4-(trifluoromethyl)phenyl]-ethenyl]-1,3-oxazole (3.3 g, 3.71 mmol, yield 62%).

Reference Example 20

[2-[(E)-2-[4-(Trifluoromethyl)phenyl]ethenyl]-1,3-oxazol-4-yl]methylmethanesulfonate

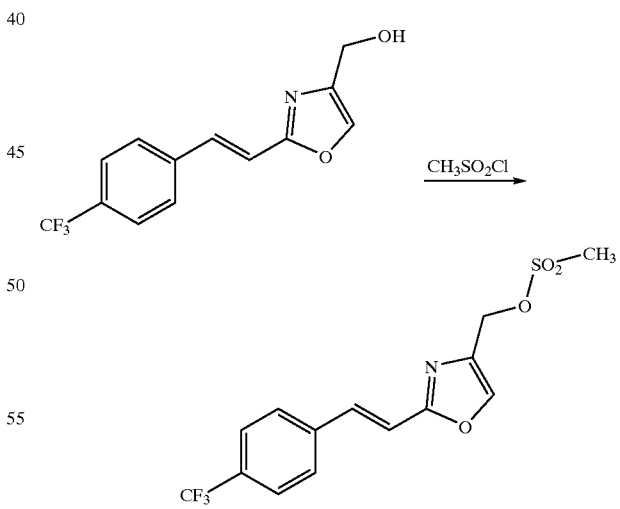

4-(Hydroxymethyl)-2-[(E)-2-[4-(trifluoromethyl)phenyl]-ethenyl]-1,3-oxazole (5.0 g, 18.6 mmol) and triethylamine (3.1 mL, 22.4 mmol) were added to THF solution (25 ml), and methanesulfonyl chloride (1.8 mL, 23.3 mmol) was added dropwise under ice-cooling. THF (25 ml) was added at the same temperature and the mixture was stirred for 40 min. The mixture was stirred at room temperature for 1 more hour. To the mixture was added water (25 ml) and the mixture was extracted with ethyl acetate (25 ml). The organic layer was washed with water (25 ml). The aqueous layers were combined and extracted with ethyl acetate (25 ml). The organic layers were combined and concentrated. Ethyl acetate (40 ml) and isopropyl ether (10 ml) were added to the→residue. The mixture was heated to 60° C. for dissolution. After allowing to cool to room temperature with stirring, isopropyl ether (10 ml) was added under ice-cooling and the precipitated crystals were collected by filtration. The crystals were washed with isopropyl ether (10 ml) and dried under reduced pressure to give [2-[(E)-2-[4-(trifluoromethyl)phenyl]ethenyl]-1,3-oxazol-4-yl]methylmethanesulfonate (5.1 g, 14.5 mmol, yield 78%).

$^{1}$H-NMR (CDCl$_{3}$, δ, 300 MHz) 3.09(3H,s), 5.22(1H,s), 7.00(1H,d,J=16.4 Hz), 7.57(1H,d,J=16.4 Hz), 7.60–7.69 (4H,m), 7.78(1H,s).

Reference Example 21

1-[4-[4-[[2-[(E)-2-[4-(trifluoromethyl)phenyl]ethenyl]-1,3-oxazol-4-yl]methoxy]phenyl]butyl]-1H-1,2,3-triazole mmol) and tetra(n-butyl) ammonium bromide (45 mg, 0.14 mmol) were added to THF (5 ml), and 1N-aqueous sodium hydroxide solution (3.0 mL, 3.00 mmol) was added. The mixture was stirred at room temperature for 5 hours. 10% Brine (10 ml) was added and the mixture was extracted with ethyl acetate (10 ml). The organic layer was washed with 10% brine (10 ml). The aqueous layers were combined and extracted with ethyl acetate (10 ml). The organic layers were combined and concentrated. Ethanol (15 ml) was added to the residue and the mixture was refluxed under heating for dissolution. After allowing to cool to room temperature and stirring, the mixture was stirred for 1 hour under ice-cooling. The precipitated crystals were collected by filtration, washed with cold-ethanol (2 ml) and dried under reduced pressure to give 1-[4-[4-[[2-[(E)-2-[4-(trifluoromethyl)phenyl]ethenyl]-1,3-oxazol-4-yl]methoxy]phenyl]butyl]-1H-1,2,3-triazole (556 mg, 1.19 mmol, yield 81%).

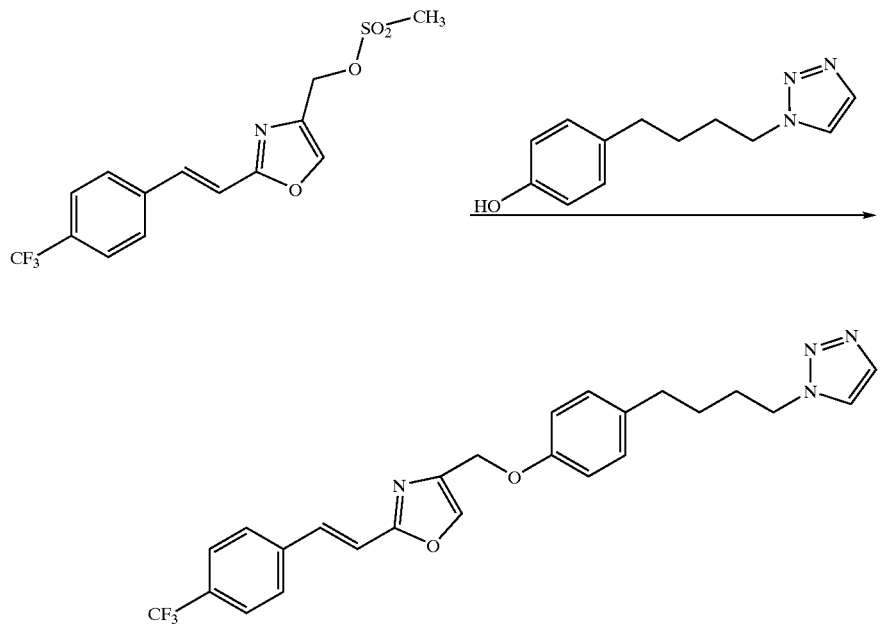

[2-[(E)-2-[4-(Trifluoromethyl)phenyl]ethenyl]-1,3-oxazol-4-yl]methylmethanesulfonate (500 mg, 1.44 mmol), 4-[4-(1H-1,2,3-triazol-1-yl)butyl]phenol (344 mg, 1.58

EXAMPLE 29

1-[4-[4-[[2-[(E)-2-[4-(trifluoromethyl)phenyl]ethenyl]-1,3-oxazol-4-yl]methoxy]phenyl]butyl]-1H-1,2,3-triazole

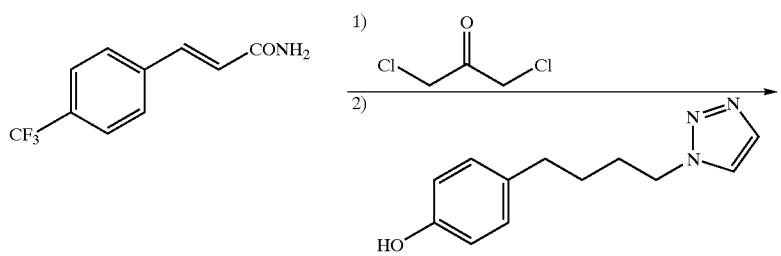

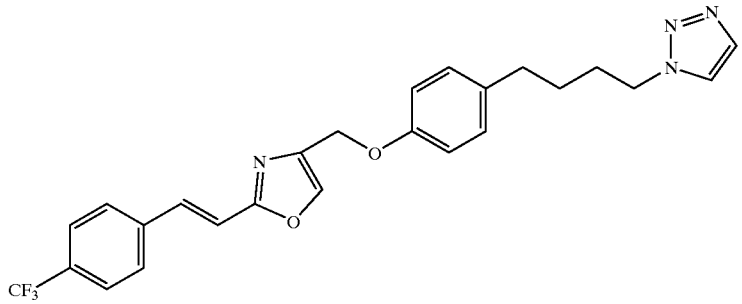

(E)-3-(4-(Trifluoromethyl)phenyl)-2-propenamide (4.00 g, 18.59 mmol) and 1,3-dichloroacetone (3.54 g, 27.89 mmol) were added to toluene (14 ml) and the mixture was subjected to refluxing azeotropic dehydration using a Dean-Stark tube for 3 hours. A solution of sulfuric acid (91 mg) in toluene (1 ml) was added at the same temperature and the mixture was further subjected to refluxing azeotropic dehydration for 3.5 hours. The reaction mixture was concentrated under reduced pressure, and THF (20 ml) and tetra(n-butyl) ammonium bromide (428 mg, 1.328 mmol) were added to the residue. 30% Aqueous potassium hydroxide solution (12.42 g, 66.4 mmol) was added dropwise at 20–30° C. and the mixture was stirred at the same temperature for 15 min. 4-[4-(1H-1,2,3-Triazol-1-yl)butyl]phenol (2.89 g, 13.28 mmol) was added and the mixture was refluxed under stirring for 2 hours. Water (13.4 ml) and methanol (20 ml) were added dropwise at the same temperature. After allowing to cool to room temperature and stirring, the mixture was stirred at the same temperature for 1 hour. The precipitated crystals were collected by filtration, washed with cold-methanol (40 ml) and dried under reduced pressure to give 1-[4-[4-[[2-[(E)-2-[4-(trifluoromethyl)phenyl]ethenyl]-1,3-oxazol-4-yl]methoxy]phenyl]butyl]-1H-1,2,3-triazole (5.35 g, 11.42 mmol, yield 86%).

Reference Example 22

Production of 1-[4-[4-[[2-[(E)-2-[4-(trifluoromethyl)-phenyl]ethenyl]-1,3-oxazol-4-yl]methoxy]phenyl]butyl]-1H-1,2,3-triazole 1-[4-[4-[[2-[(E)-2-[4-(Trifluoromethyl)phenyl]ethenyl]-1,3-oxazol-4-yl]methoxy]phenyl]butyl]-1H-1,2,3-triazole (5.0 g) was added to water/1-propanol=1/9 (65 ml), and active charcoal (100 mg) was added. After refluxing under heating, an insoluble material was filtered off while hot, and the residue was washed with water/1-propanol=1/9 (5 ml). The filtrate was refluxed again and was allowed to cool and stirred at 50° C. to 55° C. for 30 min. Water (56 ml) was added dropwise at the same temperature and the mixture was stirred at from 50° C. to 60° C. for 20 hours. The crystals were filtrated, washed with water (50° C.) and dried under reduced pressure at 40° C. to give 1-[4-[4-[[2-[(E)-2-[4-(trifluoromethyl)phenyl]ethenyl]-1,3-oxazol-4-yl]methoxy]-phenyl]butyl]-1H-1,2,3-triazole (4.29 g, yield 92%) as crystals (the same crystals as those obtained in Example 4 of Japanese Patent Application No. 2000-108204).

The crystals were analyzed by powder X ray diffraction, the results of which are shown in the following.

The crystals showed a powder X ray diffraction pattern showing characteristic peaks at diffraction angles (2θ) of powder X ray diffraction of 15.88, 21.22 and 21.82 degrees. The powder X ray diffraction chart is shown in FIG. 1.

EXAMPLE 30

Production of 1-[4-[4-[[2-[(E)-2-[4-(trifluoromethyl)-phenyl]ethenyl]-1,3-oxazol-4-yl]methoxy]phenyl]butyl]-1H-1,2,3-triazole 1-[4-[4-[[2-[(E)-2-[4-(Trifluoromethyl)phenyl]ethenyl]-1,3-oxazol-4-yl]methoxy]phenyl]butyl]-1H-1,2,3-triazole (150.0 g) was added to acetone (1.5 L). The mixture was refluxed under heating and the insoluble material was filtered off. The residue was washed with acetone (60 ml) and the filtrate and the washing solution were refluxed. Water (150 ml) was added dropwise under reflux. The mixture was allowed to cool and stirred at 30° C. Water (390 ml) was added dropwise and the mixture was stirred at room temperature for 2 hours and under ice-cooling for 5.5 hours. The reaction mixture was filtrated, washed with ice-cooled acetone/water=1/1 (300 ml×2) and dried under reduced pressure at 40° C. to give 1-[4-[4-[[2-[(E)-2-[4-(trifluoromethyl)phenyl]ethenyl ]-1,3-oxazol-4-yl]methoxy]-phenyl]butyl]-1H-1,2,3-triazole as crystals (141.4 g, yield 94%).

The crystals were analyzed by powder X ray diffraction, the results of which are shown in the following.

Figure 2:
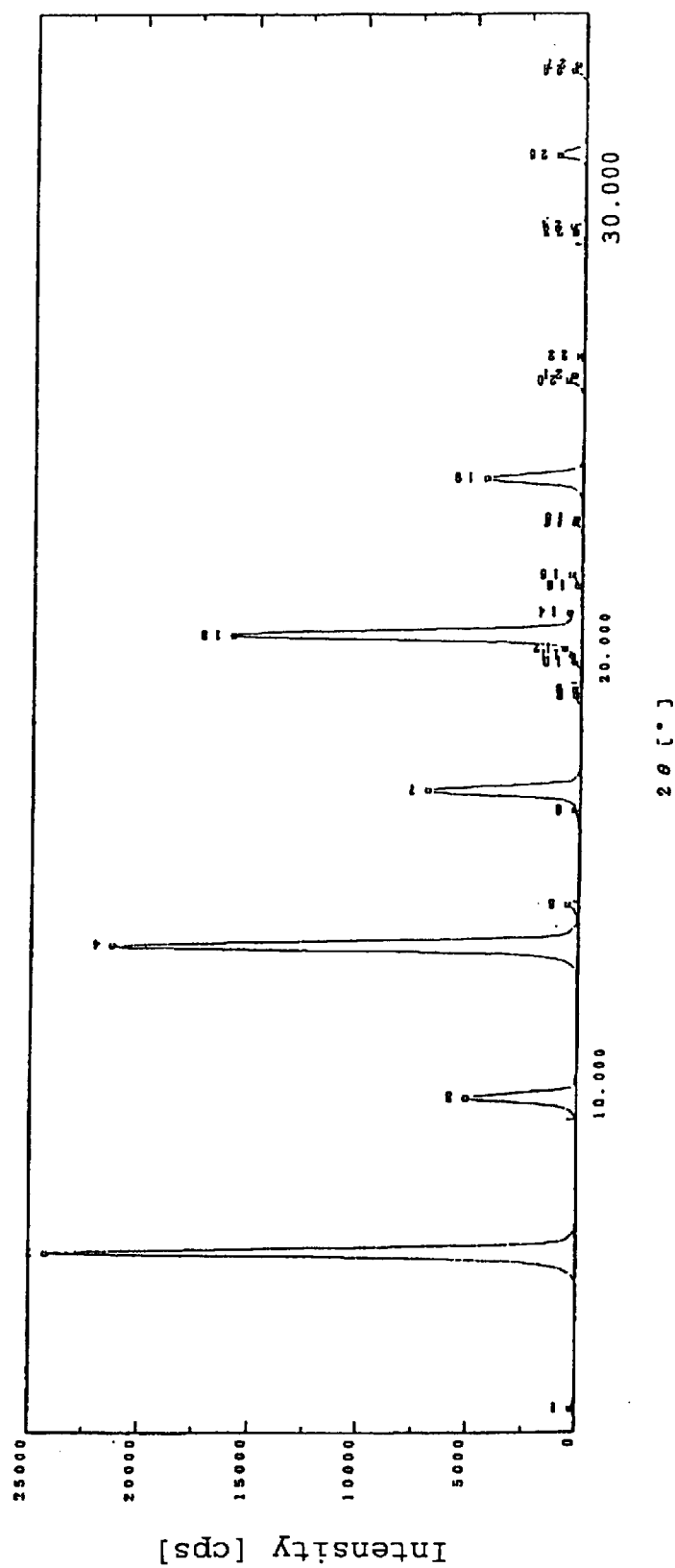
FIG. 2 is a powder X-ray diffraction chart of the compound obtained in Example 30.

The crystals showed a powder X ray diffraction pattern showing characteristic peaks at diffraction angles (2θ) of powder X ray diffraction of 6.98, 14.02, 17.56, 21.10 and 24.70 degrees. The powder X ray diffraction chart is shown in FIG. 2.

Reference Example 23

Production of 1-[4-[4-[[2-[(E)-2-[4-(trifluoromethyl) phenyl]-ethenyl]-1,3-oxazol-4-yl]methoxy]phenyl]butyl]-1H-1,2,3-triazole methanesulfonate 1-[4-[4-[[2-[(E)-2-[4-(Trifluoromethyl)phenyl]ethenyl]-1,3-oxazol-4-yl]methoxy]phenyl]butyl]-1H-1,2,3-triazole (1.0 g) was dissolved in ethyl acetate (50 ml) and tetrahydrofuran (5 ml). A solution of methanesulfonic acid (205 mg) in tetrahydrofuran (5 ml) was added dropwise. The crystals were precipitated. The mixture was stirred at room temperature for 20 min and under ice-cooling for 50 min. The reaction mixture was concentrated under reduced pressure until the liquid amount became about half. After stirring the mixture under ice-cooling for 30 min, the mixture was filtrated, washed with ethyl acetate/isopropyl ether=1/1 (3 ml) and dried under reduced pressure (40° C.) to give 1-[4-[4-[ [2-[ (E)-2-[4-(trifluoromethyl)-phenyl]ethenyl]-1,3-oxazol-4-yl]methoxy]phenyl]butyl]-1H-1,2,3-triazole methanesulfonate (1.18 g, yield 98%).

1H-NMR (300 MHz, CDCl$_3$, δ) 1.61–1.69(2H,m), 1.94–2.05(2H,m), 2.62(2H,t,J=7.35 Hz),2.90(3H,s),4.51 (2H,t,J=7.14 Hz)5.05(2H,s),6. 91–7.13(5H,m),7.60–7.74 (6H,m),7.97(1H,s),8.16(1H,s).

Reference Example 24

Production of 1-[4-[4-[[2-[(E)-2-[4-(trifluoromethyl) phenyl]-ethenyl]-1,3-oxazol-4-yl]methoxy]phenyl]butyl]-1H-1,2,3-triazole p-toluenesulfonate 1-[4-[4-[[2-[(E)-2-[4-(Trifluoromethyl)phenyl]ethenyl]-1,3-oxazol-4-yl]methoxy]phenyl]butyl]-1H-1,2,3-triazole (1.0 g) was dissolved in ethyl acetate (50 ml) and tetrahydrofuran (5 ml). A solution of p-toluenesulfonic acid monohydrate (406 mg) in tetrahydrofuran (5 ml) was added dropwise. The crystals were precipitated. The mixture was stirred at room temperature for 2 hours 20 min and filtrated. The mixture was washed with ethyl acetate/isopropyl ether=1/1 (3 ml) and dried under reduced pressure (40° C.) to give 1-[4-[4-[[2-[(E)-2-[4-(trifluoromethyl)phenyl]ethenyl]-1,3-oxazol-4-yl]methoxy]phenyl]butyl]-1H-1,2,3-triazole p-toluenesulfonate (1.1 g, yield 80%).

$^1$H-NMR (300 MHz, CDCl$_3$, δ) 1.58–1.66(2H,m), 1.90–2.01(2H,m),2.31(3H,s), 2.59(2H,t,J=7.28 Hz), 4.49 (2H,t,J=7.06 Hz), 5.05(2H, s),6.88–7.19(7H,m), 7.61–7.81 (8H,m), 8.02(1H,s), 8.16(1H,s).

Reference Example 25

Production of 1-[4-[4-[[2-[(E)-2-[4-(trifluoromethyl) phenyl]-ethenyl]-1,3-oxazol-4-yl]methoxy]phenyl]butyl]-1H-1,2,3-triazole benzenesulfonate 1-[4-[4-[[2-[(E)-2-[4-(Trifluoromethyl)phenyl]ethenyl]-1,3-oxazol-4-yl]methoxy]phenyl]butyl]-1H-1,2,3-triazole (1.0 g) was dissolved in ethyl acetate (50 ml) and tetrahydrofuran (5 ml). A solution of benzenesulfonic acid monohydrate (376 mg) in tetrahydrofuran (5 ml) was added dropwise. The crystals were precipitated. The mixture was stirred room temperature for 2 hours and filtrated. The mixture was washed with ethyl acetate/isopropyl ether=1/1 (3 ml) and dried under reduced pressure (40° C.) to give 1-[4-[4-[[2-[(E)-2-[4-(trifluoromethyl)-phenyl]ethenyl]-1,3-oxazol-4-yl]methoxy]phenyl]butyl]-1H-1,2,3-triazole benzenesulfonate (1.05 g, yield 78%).

$^1$H-HNR (300 MHz, CDCl$_3$+DMSO-d$_6$, δ) 1.54–1.66(2H, m), 1.88–1.99(2H,m), 2.58(2H,t,J=7.47 Hz), 4.44(2H,t,J= 7.17 Hz), 5.00(2H,s),6.87–7.06(5H,m), 7.39–7.44(3H,m), 7.53–7.70(6H,m), 7.80(1H,s), 7.87–7.91(2H,m),7.99(1H,s).

Reference Example 26

Production of 1-[4-[4-[[2-[(E)-2-[4-(trifluoromethyl) phenyl]-ethenyl]-1,3-oxazol-4-yl]methoxy]phenyl]butyl]-1H-1,2,3-triazole sulfate 1-[4-[4-[[2-[(E)-2-[4-(Trifluoromethyl)phenyl]ethenyl]-1,3-oxazol-4-yl]methoxy]phenyl]butyl]-1H-1,2,3-triazole (1.0 g) was dissolved in ethyl acetate (50 ml) and tetrahydrofuran (5 ml). A solution of sulfuric acid (209 mg) in tetrahydrofuran (5 ml) was added dropwise. The crystals were precipitated. The mixture was stirred at room temperature for 40 min and filtrated. The mixture was washed with ethyl acetate (3 ml) and dried under reduced pressure (40° C.) to give 1-[4-[4-[[2-[(E)-2-[4-(trifluoromethyl)phenyl] ethenyl]-1,3-oxazol-4-yl]methoxy-phenyl]butyl]-1H-1,2,3-triazole sulfate (1.13 g, yield 93%).

$^1$H-HNR (300 MHz, CDCl$_3$+DMSO-d$_6$, δ) 1.56–1.66(2H, m), 1.89–2.00(2H,m), 2.60(2H,t,J=7.50 Hz), 4.45(2H,t,J= 7.11 Hz),5.00(2H,s), 6.88–7.10(5H,m), 7.53–7.70(5H,m), 7.93(1H,s), 7.82(1H,s), 7.85(1H,s).

Reference Example 27

Production of 1-[4-[4-[[2-[(E)-2-[4-(trifluoromethyl) phenyl]-ethenyl]-1,3-oxazol-4-yl]methoxy]phenyl]butyl]-1H-1,2,3-triazole hydrochloride 1-[4-[4-[[2-[(E)-$^2$-[4-(Trifluoromethyl)phenyl]ethenyl]-1,3-oxazol-4-yl]methoxy]phenyl]butyl]-1H-1,2,3-triazole(1.5 g) was dissolved in tetrahydrofuran (75 ml). Concentrated hydrochloric acid (0.3 ml) was added dropwise. The crystals were precipitated. The mixture was stirred at room temperature for 40 min and filtrated. The mixture was washed with ethyl acetate (3 ml) and dried under reduced pressure (40° C.) to give 1-[4-[4-[[2-[(E)-2-[4-(trifluoromethyl)phenyl] ethenyl]-1,3-oxazol-4-yl]methoxy]phenyl]butyl]-1H-1,2,3-triazolehydrochloride (1.09 g, yield 67%).

$^1$H-HNR (300 MHz, CDCl$_3$+DMSO-d$_6$, δ) 1.60–1.66(2H, m), 1.93–1.98(2H,m), 2.61(2H,t,J=7.53 Hz), 4.43(2H,t,J= 7.08 Hz), 5.03(2H,s), 6.90–7.09(5H,m), 7.55–7.81(8H,m).

Industrial Applicability

According to the production methods of the present invention, 1-substituted-1,2,3-triazole compounds having a tyrosine kinase (especially HER2) inhibitory action can be produced efficiently in a high yield at an industrial large scale by a convenient method.

What is claimed is:

1. A method for producing a compound of the formula:

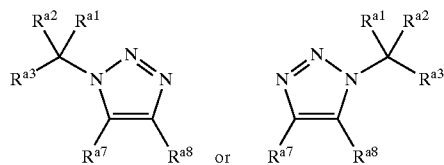

wherein $R^{a1}$ and $R^{a2}$ are each a hydrogen atom, a substituted hydroxy, a substituted thiol, a substituted amino, an optionally substituted hydrocarbon group, or an acyl;

$R^{a3}$ is a group of the formula:

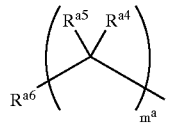

wherein $R^{a4}$ and $R^{a5}$ are each a hydrogen atom, an optionally substituted hydroxy, an optionally substituted thiol, an optionally substituted amino, an optionally substituted hydrocarbon group, or an acyl, or $R^{a4}$ and $R^{a5}$ in combination form oxo, $R^{a6}$ an optionally substituted aromatic group, and $m^a$ is an integer of 0 to 10; or two or three from $R^{a1}$, $R^{a2}$ and $R^{a3}$ form an optionally substituted ring, together with the adjacent carbon atom; and $R^{a7}$ and $R^{a8}$ are each a hydrogen atom, a halogen, an optionally substituted hydroxy, an optionally substituted thiol, an optionally substituted amino, an optionally substituted hydrocarbon, or an acyl, which method comprises reacting a compound of the formula:

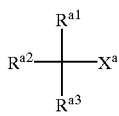

wherein $X^a$ is a leaving group and other symbols are as defined above, or a salt thereof, and compound of the formula:

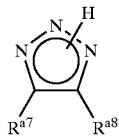

wherein each symbol is as defined above, or a salt thereof,
(1) in a secondary or tertiary alcohol in the presence of a base, or
(2) in the absence of a base.

2. The production method of claim 1, which comprises reaction in a secondary or tertiary alcohol in the presence of a base.

3. The production method of claim 1, which comprises reaction in a tertiary alcohol in the presence of a base.

4. The production method of claim 1, wherein $R^{a1}$ is a hydrogen atom.

5. The production method of claim 1, wherein $R^{a1}$ and $R^{a2}$ are each a hydrogen atom.

6. The production method of claim 1, wherein $R^{a3}$ is a group of the formula:

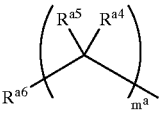

wherein each symbol is as defined in claim 1.

7. The production method of claim 6, wherein $R^{a4}$ and $R^{a5}$ are each a hydrogen atom.

8. The production method of claim 6, wherein $R^{a6}$ is an optionally substituted phenyl.

9. The production method of claim 6, wherein $m^a$ is 3.

10. The production method of claim 1, wherein $R^{a7}$ and $R^{a8}$ are each a hydrogen atom.

11. The production method of claim 1, wherein $R^{a1}$, $R^{a2}$, $R^{a7}$ and $R^{a8}$ are each a hydrogen atom and $R^{a3}$ is 3-[4-(t-butoxyphenyl)]propyl.

* * * * *